US008354532B2

(12) United States Patent
Girardet et al.

(10) Patent No.: US 8,354,532 B2
(45) Date of Patent: Jan. 15, 2013

(54) PYRROLO [2,3-D] PYRIMIDINES AS NON-NUCLEOSIDE REVERSE TRANSCRIPTASE INHIBITORS FOR TREATMENT OF HIV

(75) Inventors: Jean-Luc Girardet, San Diego, CA (US); Yung-hyo Koh, Irvine, CA (US); Stephanie Shaw, Rowland Heights, CA (US); Hong Woo Kim, San Diego, CA (US); Zhi Hong, Chapel Hill, NC (US)

(73) Assignee: Ardea Biosciences, Inc., San Diego, CA (US)

( * ) Notice: Subject to any disclaimer, the term of this patent is extended or adjusted under 35 U.S.C. 154(b) by 0 days.

(21) Appl. No.: 13/470,116

(22) Filed: May 11, 2012

(65) Prior Publication Data
US 2012/0226037 A1 Sep. 6, 2012

Related U.S. Application Data

(62) Division of application No. 11/919,786, filed as application No. PCT/US2006/017677 on May 5, 2006, now Pat. No. 8,227,601.

(60) Provisional application No. 60/678,667, filed on May 5, 2005.

(51) Int. Cl.
*C07D 487/00* (2006.01)
(52) U.S. Cl. ..................... 544/280
(58) Field of Classification Search ........ None
See application file for complete search history.

(56) References Cited

U.S. PATENT DOCUMENTS

| 6,271,370 B1 | 8/2001 | Scott |
| 6,414,147 B1 | 7/2002 | Currie et al. |

FOREIGN PATENT DOCUMENTS

| WO | WO-00-27850 A2 | 5/2000 |
| WO | WO-00-43394 A1 | 7/2000 |
| WO | WO-03-016306 A1 | 2/2003 |
| WO | WO-2004-069812 A1 | 8/2004 |
| WO | WO-2005-028479 A2 | 3/2005 |
| WO | WO-2006-045828 A1 | 5/2006 |
| WO | WO-2006-122003 A2 | 11/2006 |

OTHER PUBLICATIONS

Badger, G.M. and Rao, R.P., "Azaindoles. The Synthesis of Pyrazolo[3,4-b]Pyridines and Pyrazolo[3,4-d]Pyrimidines," Aust. J. Chem. 18:1267-1271 (1965).
Balzarni, J., "Current Status of the Non-nucleoside Reverse Transcriptase Inhibitors of Human Immunodeficiency Virus Type 1," Cur. Top, Med. Chem. 4:921-944 (2004).
Berge et al., "Pharmaceutical Salts," J. Pharm. Sci. 66:1-19 (1977).
Bitterli, "Uber einige Derivate des Triazolo-pyrimidins," Helvetica Chimica Acta 34:835-840 (1951).
Bontems, R.J. et al., "Guanosine Analogs. Synthesis of Nucleosides of Certain 3-Substituted 6-Aminopyrazolo[3,4-d]pyrimidin-4(5H)-ones as Potential Immunotherapeutic Agents," J. Med. Chem. 33:2174-2178 (1990).
Buckheit, "Non-nucleoside reverse transcriptase inhibitors: perspectives onnovel therapeutic compounds and strategies for the treatment of HIV infection," Exp. Op. Investig. Drugs 10(8):1423-1442 (2001).
Bundgaard, "Design and Application of Prodrugs," in Textbook of Drug Design and Development, Krosgaard-Larsen and Bundgaard, ed. 1991, Chapter 5, pp. 113-191 (1991).
Bundgaard, H., "Means to Enhance Penetration: (1) Prodrugs as a means to improve the delivery of peptide drugs," Advanced Drug Delivery Reviews 8:1-38 (1992).
Combellas et al., "Synthesis of 4-(3,5-dialkyl-4-hydroxyphenyl)pyridines," Tetrahedron Letters 33:4923-4926 (1992).
Connor, R.I. et al., "Characterization of the Functional Properties of env Genes from Long-Term Survivors of Human Immunodeficiency Virus Type I Infection," J. Virol. 70:5306-5311 (1996).
De Clercq et al., "Antiviral drug discovery and development: Where chemistry meets with biomedicind" Antiviral Research, Elsevier Science BV., Amsterdam, NL vol. 67, No. 2 Aug. 1, 2005 pp. 56-75.
European Search Report EP 06759292 Dated Sep. 19, 2008.
Fleisher et al., "Improved oral drug delivery: solubility limitations overcome by the use of prodrugs," Advanced Drug Delivery Reviews 19:115-130 (1996).
Furniss et al., eds., Vogel's Encyclopedia of Practical Organic Chemistry, 5th Supp., Longman Scientific and Technical Ltd., Essex, 1991, pp. 809-816.
Harrington, R. et al., "Direct detection of infectious HIV-1 in blood using a centrifugation-indicator cell assay," J. Virol. Methods 88:111-115 (2000).
Lewis, A.E. and Townsend, L.B., "Pyrazolopyrimidine Nucleosides. 13. Synthesis of a Novel C-Nucleoside 5-Amino-3-(β-D-ribofuranosyl)pyrazolo[4,3-d]pyrimidin-7-one, a Guanosine Analogue Related to the Nucleoside Antibiotic Formycin B," J. Am. Chem. Soc. 104:1073-1078 (1982).
Liu, M. et al., "An Improved Synthesis of 9-Deazaguanine," Synthetic Communications 32:3797-3802 (2002).
Liu, M, et al., "An Improved Synthesis of 9-Deazaguanine," Synthetic Conununications vol. 32(24):3797-3802 (2002).
Ludovici et al., "Evolution of anti-HIV drug candidates. Part 3: Diarylpyrimidine (DAPY) analogues" Bioorganic & Medicinal Chemistry Letters, Oxford, GB vol. 11, Jan. 1, 2001 p. 2235-2239.
Ludovici, D.W. et al., "Evolution of Anti-HIV Drug Candidates. Part 3. Diarylpyrimidine (DAPY) Analogues,"Bioorg. Med. Chem. Lett. 11:2235-2239 (2002).
Popik, W. et al., "Human Immunodeficiency Virus Type I Uses Lipid Raft-Colocalized CD4 and Chemokine Receptors for Productive Entry into CD+ T Cells," J. Virol. 76:4709-4722 (2002).
Roos, J.W. et al., "LuSIV Cells: A Receptor Cell Line for the Detection and Quantitation of a Single Cycle of HIV and SIV Replication," Virology 273:307-315 (2000).
Saulnier et al., "An Efficient Method for the Synthesis of Guandino Prodrugs," Bioorg, Med. Chem. Ltrs. 4(16):1985-1990 (1994).
Schang, L. M.: "Cyclin-dependent kinases as cellular targets for antiviral drugs" Journal of Antimicrobial Chemotherapy, Saunders Co., Ltd., London, GB vol. 50, No. 6 Dec. 1, 2002 pp. 779-792.

(Continued)

*Primary Examiner* — Jeffrey Murray
(74) *Attorney, Agent, or Firm* — Wilson, Sonsini, Goodrich & Rosati

(57) ABSTRACT

This application concerns certain 2-phenylamino-6-aryl amino-, 6-aryloxy-, and 6-arylthio-purines, -azapurines and -deazapurines. These compounds are non-nucleoside reverse transcriptase inhibitors and have potential as anti-HIV treatment.

14 Claims, No Drawings

OTHER PUBLICATIONS

Schow, et al., "Synthesis and activity of 2,6,9-trisubstituted purines" Bioorganic & Medicinal Chemistry Letters, Oxford, GB vol. 7, No. 21 Nov. 4, 1997 pp. 2697-2702.

Seela, F., "Synthesis of 2'-Deoxyribofuranosides of 8-Aza-7-deazaguanine and Related Pyrazolo[3,4-d]pyrimidines," Helv. Chim. Act. 69:1602-1613 (1986).

Seela, F., "The High-Anti Conformation of 7-Halogenated 8-Aza-7-deaza-2'-deoxy-guanosines: A Study of the Influence of Modified Bases on the Sugar Structure of Nucleosides," Helv. Chim. Act. 82:105-124 (1999).

Taylor, E.C. and Patel, H.H., "Synthesis of Pyrazolo[3,4-d]pyrimidine Analogues of the Potent Antitumor Agent N-{4-[2-(2-Amino -4(3H)-oxo-7H-pyrrolo [2,3-d]pyrimidin-5-yl)ethyl] benzoyl}-L-glutamic Acid (LY231514)," Tetrahedron 48:8089-8100 (1992).

Vittori, et al., "Sixth Internatnional Conference on Antiviral Research; Venice, Italy; Apr. 25-30, 1993; 1-Deazapurine derivatives: A new class of antiviral compounds" Antiviral Research, Elsevier, Amsterdam, vol. 20, No. Su.p 1, 1993.

Vogel, Textbook of Practical Organic Chemistry 5th ed., 1989: Ch. 5.19 Resolution of Racemates, pp. 809-823.

Youssif, S. et al., "A Facile One-pot Synthesis of Fused 2-Thiouracils: Dipyrimidinopyridine, Pyrazolopyrimidine and Pyridazinopyrmidines," Bull. Kor. Chem. Soc. 24:1429-1432 (2003).

PCT/EP03/50659 patent application filed Sep. 25, 2003.

PCT/US08/86703 Search Report dated Jun. 23, 2009.

PYRROLO [2,3-D] PYRIMIDINES AS NON-NUCLEOSIDE REVERSE TRANSCRIPTASE INHIBITORS FOR TREATMENT OF HIV

CROSS-REFERENCE TO RELATED APPLICATIONS

This application is a divisional patent application of U.S. application Ser. No. 11/919,786, filed Jan. 14, 2009, now U.S. Pat. No. 8,227,601 entitled "DIARYL-PURINES, -AZAPURINES AND -DEAZAPURINES AS NON-NUCLEOSIDE REVERSE TRANSCRIPTASE INHIBITORS FOR TREATMENT OF HIV", which is the national stage entry of PCT/US06/17677, filed May, 5, 2006, which claims priority to U.S. Provisional Application Ser. No. 60/678,667, filed May 5, 2005, all of which applications are incorporated herein by reference in their entirety.

FIELD OF THE INVENTION

This application concerns certain 2-phenylamino-6-aryl amino-, 6-aryloxy-, and 6-arylthio-purines, -azapurines and -deazapurines. These compounds are non-nucleoside reverse transcriptase inhibitors and have potential as anti-HIV treatment.

BACKGROUND OF THE INVENTION

Human Immunodeficiency Virus (HIV) presents a public-health and social catastrophe too well known to require documentation. One therapeutic approach to HIV has been inhibition of the viral RNA-dependent RNA polymerase; this enzyme is frequently referred to as "reverse transcriptase," abbreviated "RT." The first RT inhibitors were nucleoside analogs such as AZT and dd. Although such nucleoside RT inhibitors were frequently effective against the wild-type virus, any single-drug treatment has been hobbled by the virus's ability to readily produce drug-resistant mutants. This has led to an intense search for non-nucleoside RT inhibitors ("NNRTIs") which are both effective and capable of retaining their effectiveness despite drug-resistance mutations. A recent review of NNRTIs can be found Balzarni, J., 2004, *Cur. Top. Med. Chem.* 4, 921-44 (Erratum ibid. 4, 1825).

Four leading NNRTI are: 1) Efavirenz (4S)-6-chloro-4-(cyclopropylethynyl)-1,4-dihydro-4-(trifluoromethyl)-2H-3,1-benzoxazin-2-one; 2) Capravirine: 1H-Imidazole-2-methanol, 5-((3,5-dichlorophenyl)thio)-4-(1-methylethyl)-1-(4-pyridinylmethyl)-carbamate (ester); 3) Etravirine (TMC 125): 4-((6-amino-5-bromo-2-((4-cyanophenyl)amino)-4-pyrimidinyl)oxy)-3,5-dimethyl-benzonitrile; and 4) Rilpivirine (TMC-278): 4-([4-[(4-[(1E)-2-cyanoethenyl]-2,6-dimethylphenyl)amino]-2-pyrimidinyl)amino]benzonitrile. Rilpivirine and Etravirine belong to a subclass of NNRTIs called diarylpyrmidines ("DAPY"). For a review of these DAPY NNRTIs see Ludovici, D. W., et al., 2002, *Bioorg. Med. Chem. Lett.* 11, 2235-9. An extensive patent literature also exists for DAPY. U.S. Pat. No. 6,197,779; WO 00/27850; WO 2003/016306; and WO 2004/069812, all assigned to Janssen Pharmaceuticals.

Diaryl compounds similar to Etravirine and Rilpivirine where the pyrimidine moiety is replaced by a purine are described in WO 2005/028479, which also is assigned to Janssen.

BRIEF DESCRIPTION OF THE INVENTION

The invention provides a compound of formula I

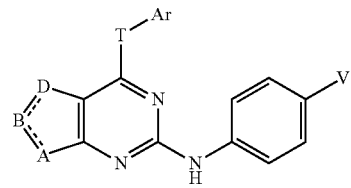

I where the dashed line represents a double bond that may be located either between A and B or between B and D, where A is —N=, N(Z) or C(Z);

B is CH or =N—;

D is CW or =N—, or N(W);

T is NH, O or S;

Z is H, F, Cl, Br, $CH_3$, $CH_2CH_3$, cyclopropyl, or benzyl, in which the phenyl moiety of the benzyl group is optionally substituted with methyl or methoxy, provided that Z is not F or Cl when A is NZ;

W is H, F, Cl, Br, methyl, ethyl, cyclopropyl, allyl, $CH_2CF_3$, cyanomethyl, cyanoethyl, CH=CHCN, or benzyl, in which the phenyl moiety of the benzyl group is optionally substituted with one or two groups selected independently from methoxy and methyl, provided that W is not F or Cl when D is NW;

V is F, Cl, CN, $SO_2CH_3$, $SO_2NH_2$, $SO_2NHCH_3$, C≡$CCH_3$, or CH=CHCN;

provided that when D is CW, A is not CZ and further provided that when neither A nor D is CZ or CW, then B is CH; and Ar is selected from (a), (b), (c), and (d) below:

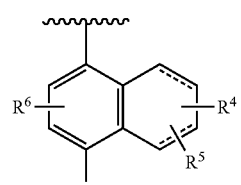

(a)

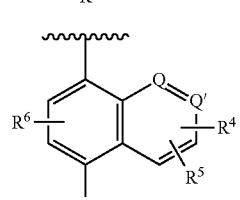

(b)

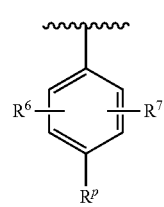

(c)

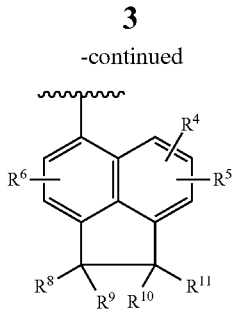
(d)

wherein each $R^p$ is selected from among methyl, ethyl, propyl, isopropyl, cyclopropylmethyl, or $C_3$-$C_6$ cycloalkyl, cyano, CH=CHCN, Cl, Br, I, acetyl and alkylamino; $R^4$, $R^5$, and each $R^6$ are independently selected from among H, F, Cl, Br, $CH_3$, $CF_3$, $CH_2F$, $CHF_2$, isopropyl, cyclopropyl, $OCH_3$, OH, $OCF_3$, $NH_2$ and $NHCH_3$, or $R^6$ and $R^p$ on adjacent ring atoms, together with the ring atoms to which they are attached, form an additional fused five-membered ring; Q and Q' are independently selected from N and CH; $R^7$ is Cl, Br, I, $CH_3$, $CF_3$, $OCH_3$, isopropyl, cyclopropyl, t-butyl, or cyclobutyl; and $R^8$-$R^{11}$ are, independently, H or $CH_3$.

Compounds of formula I have inhibitory activity against both wild-type and mutated forms of human immunodeficiency virus type 1 (HIV-1).

DETAILED DESCRIPTION OF THE INVENTION

In one embodiment this invention provides a compound of formula IA, in which the 6-linker T of formula I is T', which may be O or S.

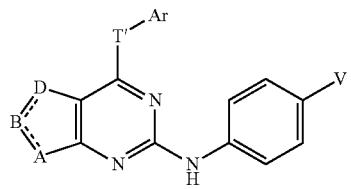
IA

When T of formula I or T' of formula IA is O, the invention excludes 1) compounds where both $R^p$ and V are CH=CHCN or cyano unless at least one of A or D is neither —N= nor —NH— and 2) compounds where a) R is CH=CHCN, cyano, or methyl; b) V is cyano or CH=CHCN; and c) A and D are both one of —N=; N-benzyl or N-(substituted benzyl).

In one subgeneric embodiment, the invention provides a compound of formula IA where Ar is selected from 4-cyclopropyl phenyl; 4-cyclopropylmethyl phenyl; 4-bromophenyl; 4-cyclopropyl-naphth-1-yl; 2,6-dimethyl-4-cyanophenyl; 2,6-dimethoxy-4-cyanophenyl; 2,6-dimethyl-4-(2-cyanoethenyl)phenyl; 2,6-dimethoxy-4-(2-cyanoethenyl)phenyl; 2-methyl-4-cyclopropyl phenyl; 2,6-dimethyl-4-cyclopropyl phenyl; 2,6-di-trifluoromethyl-4-cyclopropyl phenyl; 2,4,6-trimethyl phenyl; and 2,6-dimethyl-4-acetyl phenyl.

In another subgeneric embodiment, the invention contemplates a compound of formula IA where Ar is selected from the following: 5-cyclopropyl-8-quinolyl; 5-isopropyl-8-quinolyl; 5-cyano-8-quinolyl; 5-cyclopropyl-7-trifluoromethyl-8-quinolyl; 5-acetyl-8-quinolyl; 5-cyano-7-methoxy-8-quinolyl; 5-cyano-7-methyl-8-quinolyl; 5-cyclopropyl-7-trifluoromethoxy-8-isoquinolyl; 5-cyano-8-isoquinolyl; 5-cyano-7-methoxy-8-isoquinolyl; 5-cyano-7-methyl-8-isoquinolyl; 5-cyclobutyl-7-difluoromethyl-8-isoquinolyl; 5,7-dimethyl-8-cinnolyl; 5-cyclopropyl-7-methyl-8-cinnolyl; and 5-(2-cyanoethenyl)-7-methyl-8-cinnolyl.

In another subgeneric embodiment, the invention provides a compound of formula IA-1

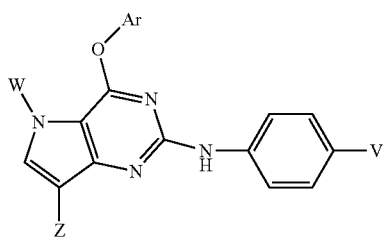
IA-1 where Ar, V, W, and Z are defined as for formula I.

In another subgeneric embodiment, the invention provides a compound of formula IA-2

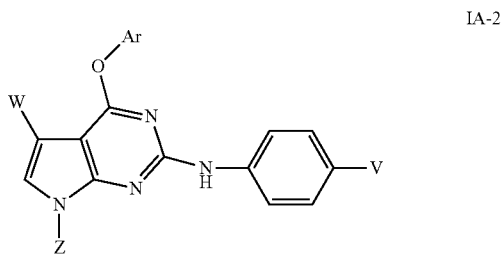
IA-2 where Ar, V, W, and Z are defined as for formula I.

In another subgeneric embodiment, the invention provides a compound of formula IA-3

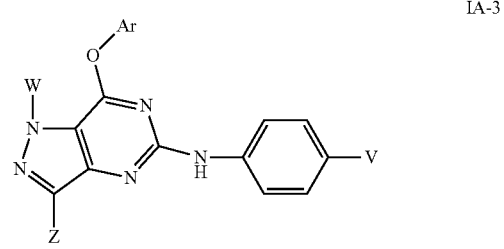
IA-3 where Ar, V, W, and Z are defined as for formula I.

In another subgeneric embodiment, this invention provides a compound of formula IA-4

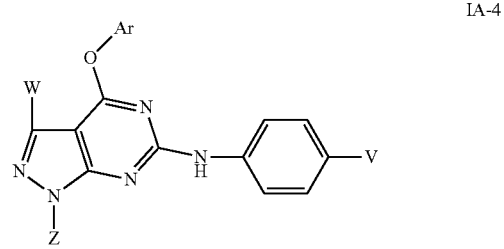
IA-4 where Ar, V, W, and Z are defined as for formula I.

In another subgeneric embodiment, this invention provides a compound of formula IA-5

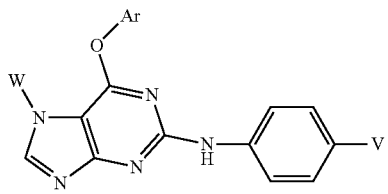

IA-5 where Ar, V, W, and Z are defined as for formula I.

In another subgeneric embodiment, this invention provides a compound of formula IA-6

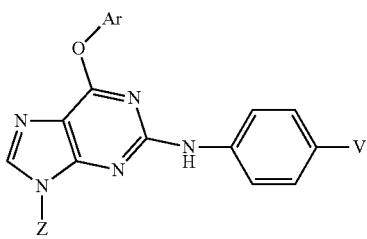

IA-6 where Ar, V, W, and Z are defined as for formula I.

In another subgeneric embodiment, this invention provides a compound of formula IA-7

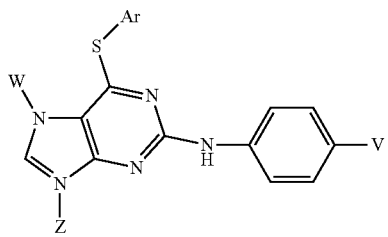

IA-7 where Ar, V, W, and Z are defined as for formula I.

In another subgeneric embodiment, this invention provides a compound of formula IA-8

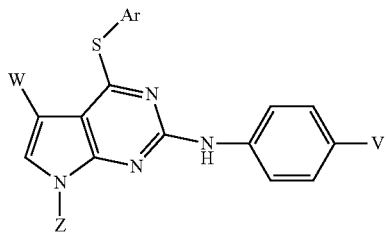

IA-8 where Ar, V, W, and Z are defined as for formula I.

In another subgeneric embodiment, this invention provides a compound of formula IA-9

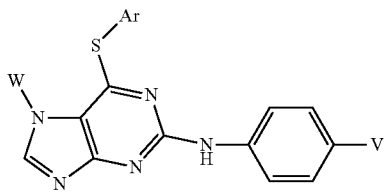

IA-9 where Ar, V, W, and Z are defined as for formula I.

In another subgeneric embodiment, this invention provides a compound of formula IA-10

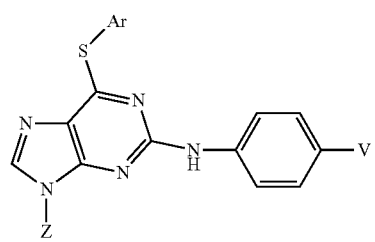

IA-10 where Ar, V, W, and Z are defined as for formula I.

In another embodiment, this invention provides a compound of formula IB

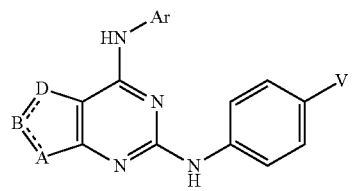

IB where all substituents are as described above, except that when Ar is (c), this invention excludes compounds in which V is either cyano or CH=CHCN, unless A or D is CZ or CW.

In one subgeneric embodiment, the invention provides a compound of formula IB where Ar is (c), subject to the exclusion in the immediately preceding paragraph.

In a more specific subgeneric embodiment, the invention provides a compound of formula IB where Ar is

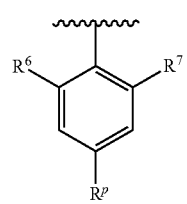

where $R^p$ is CN, CH=CHCN, or cyclopropyl; where $R^6$ and $R^7$ are either both methyl or both methoxy; and subject to the exclusion described above for formula IB.

In another subgeneric embodiment, this invention provides a compound of formula IB-1.

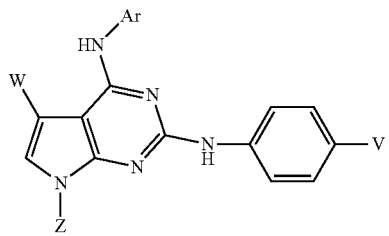

In another subgeneric embodiment, this invention provides a compound of formula IB-2.

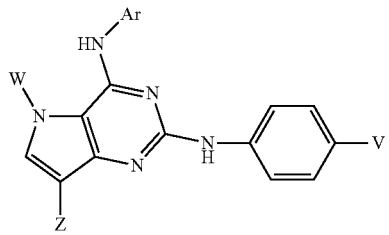

where Ar, V, W, and Z are as described above for formula IB.

In another subgeneric embodiment, the invention provides a compound of formula IB-3.

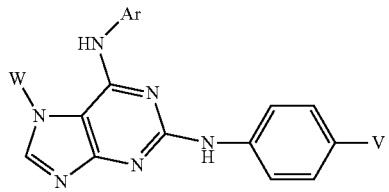

where Ar, W, and Z are as described above for formula IB.

In another subgeneric embodiment, the invention provides a compound of formula IB-4.

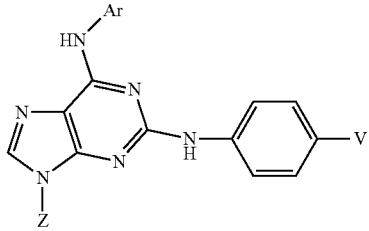

where Ar, V, and Z are as described above for formula IB.

In more specific embodiments, the invention provides compounds of any of IA-1, IA-2, IA-3, IA-4, IA-5, IA-6, IA-7, IA-8, IA-9, IA-10, IB-1, IB-2, IB-3, and IB-4, where Ar is (a).

In additional more specific embodiments, the invention provides compounds of any of IA-1, IA-2, IA-3, IA-4, IA-5, IA-6, IA-7, IA-8, IA-9, IA-10, IB-1, IB-2, IB-3, and IB-4, where Ar is (b).

In additional more specific embodiments, the invention provides compounds of any of IA-1, IA-2, IA-3, IA-4, IA-5, IA-6, IA-7, IA-8, IA-9, IA-10, IB-1, IB-2, IB-3, and IB-4, where Ar is (c).

In additional more specific embodiments, the invention provides compounds of any of IA-1, IA-2, IA-3, IA-4, IA-5, IA-6, IA-7, IA-8, IA-9, IA-10, IB-1, IB-2, IB-3, and IB-4, where Ar is (d).

In a more specific subgeneric embodiment, this invention provides or contemplates a compound of formula IA-7, IA-8, IA-9, or IA-10, where Ar is 4-cyclopropyl-, 4-acetyl-, 4-methyl-, 4-bromo-, or 4-cyano-2,6-di-substituted phenyl.

In another more specific subgeneric embodiment, this invention provides or contemplates a compound of formula IA-1, IA-2, IA-3, or IA-4, where Ar is 4-cyclopropyl-, 4-acetyl-, 4-methyl-, 4-bromo-, or 4-cyano-2,6-di-substituted phenyl.

In another more specific subgeneric embodiment, this invention provides or contemplates a compound of formula IA-5 or IA-6, where Ar is 4-cyclopropyl-, 4-acetyl-, 4-methyl-, 4-bromo- or 4-cyano-2,6-di-substituted phenyl.

Synthetic Procedures

Compounds of this invention which are of the 7-deaza-8-azapurine type can be prepared according to Scheme 1.

Scheme 1

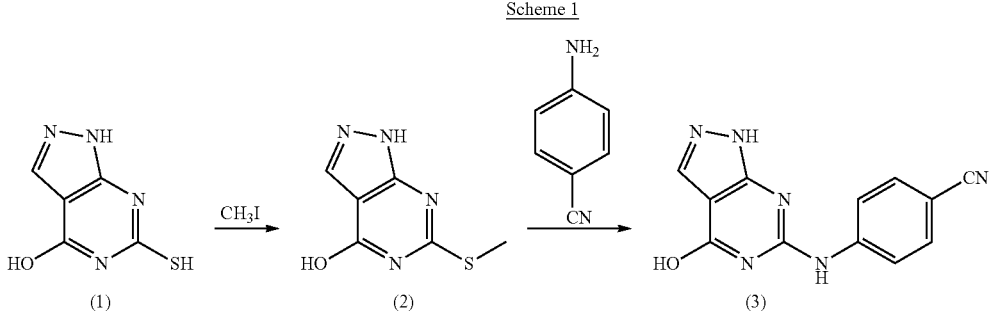

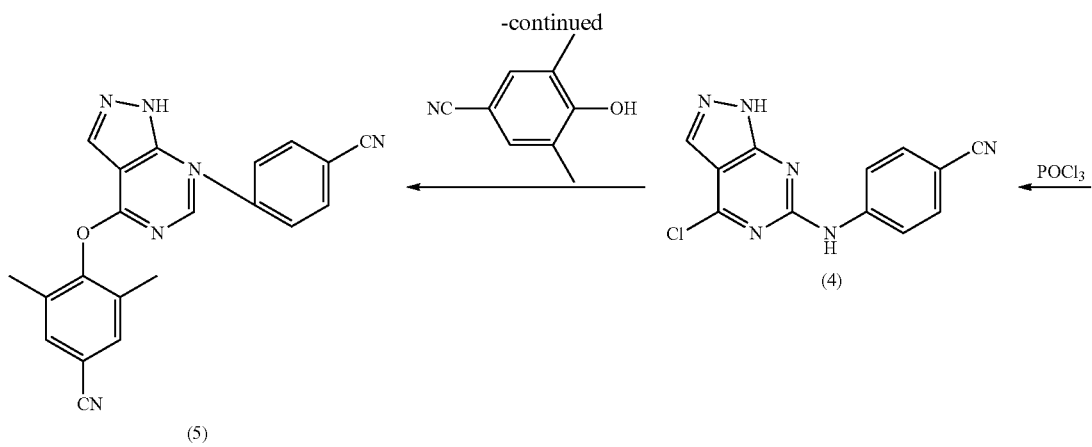

Compound (1), 2-mercapto-6-hydroxy-7-deaza-8-aza-purine, can be synthesized by published procedures known to those skilled in the art. Youssif, S., et al., 2003, *Bull. Kor. Chem. Soc.*, 24, 1429-32; Bontems, R. J., et al., 1990, *J. Med. Chem.* 33, 2174-8; Badger, G. M., & Rao, R. P., 1965, *Aust. J. Chem.* 18, 1267-71.

Alternatively, the 7-deaza-8-azapurines can be synthesized according to Scheme 2, where "PMBCl" is p-methoxy benzyl chloride. The starting material is prepared by published procedures known to those skilled in the art. Seela, F., 1999, *Helv. Chim. Act.* 82, 105-124; Taylor, E., 1992, *Tetrahedron* 48, 8089-100; Seela, F., 1986, *Helv. Chim. Act.* 69, 1602-1613.

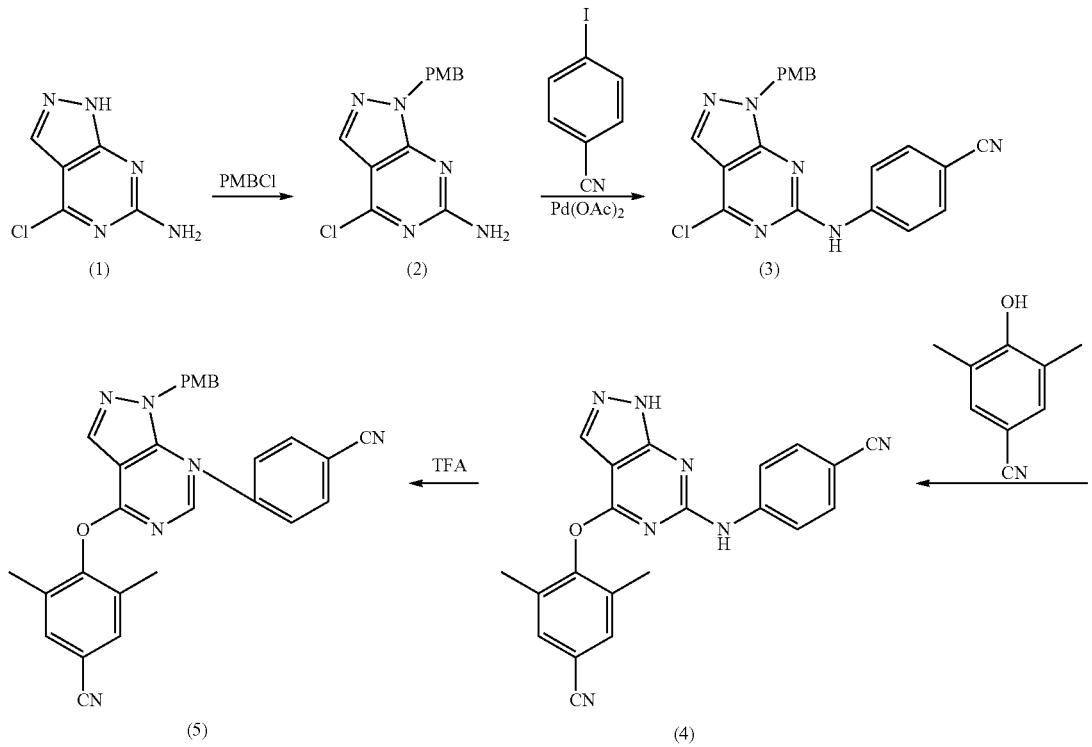

The 8-aza-9-deazapurines of this invention can be synthesized according to Scheme 3. The synthesis of the starting material was described by Lewis, A. F., & Townsend, L. B., 1982, *J. Am. Chem. Soc.* 104, 1073-78.

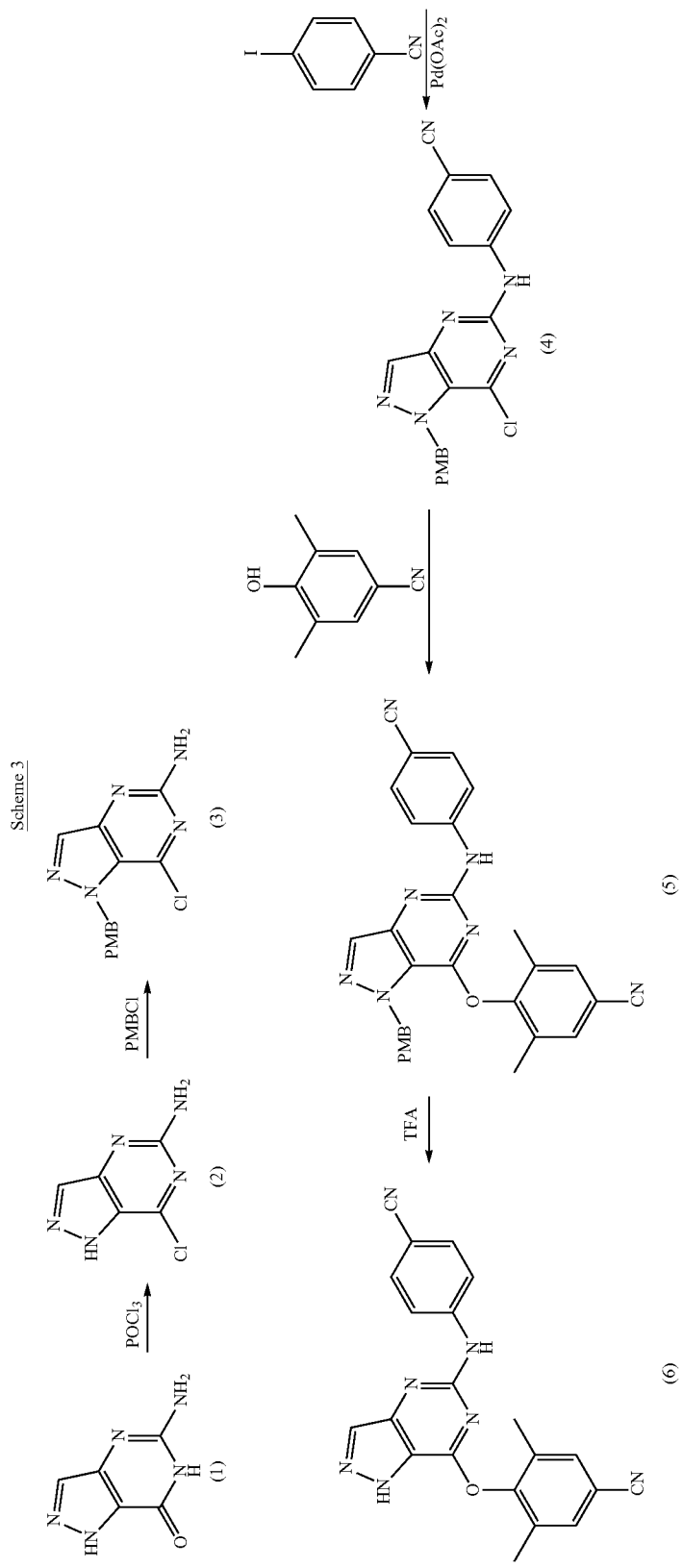

The 9-deazapurines of this invention can be synthesized by Scheme 4. The synthesis of the starting material is described by Kielich, Klaus, ed., "Synthetic Communications" 2002 vol. 32, pp-3797-3802.

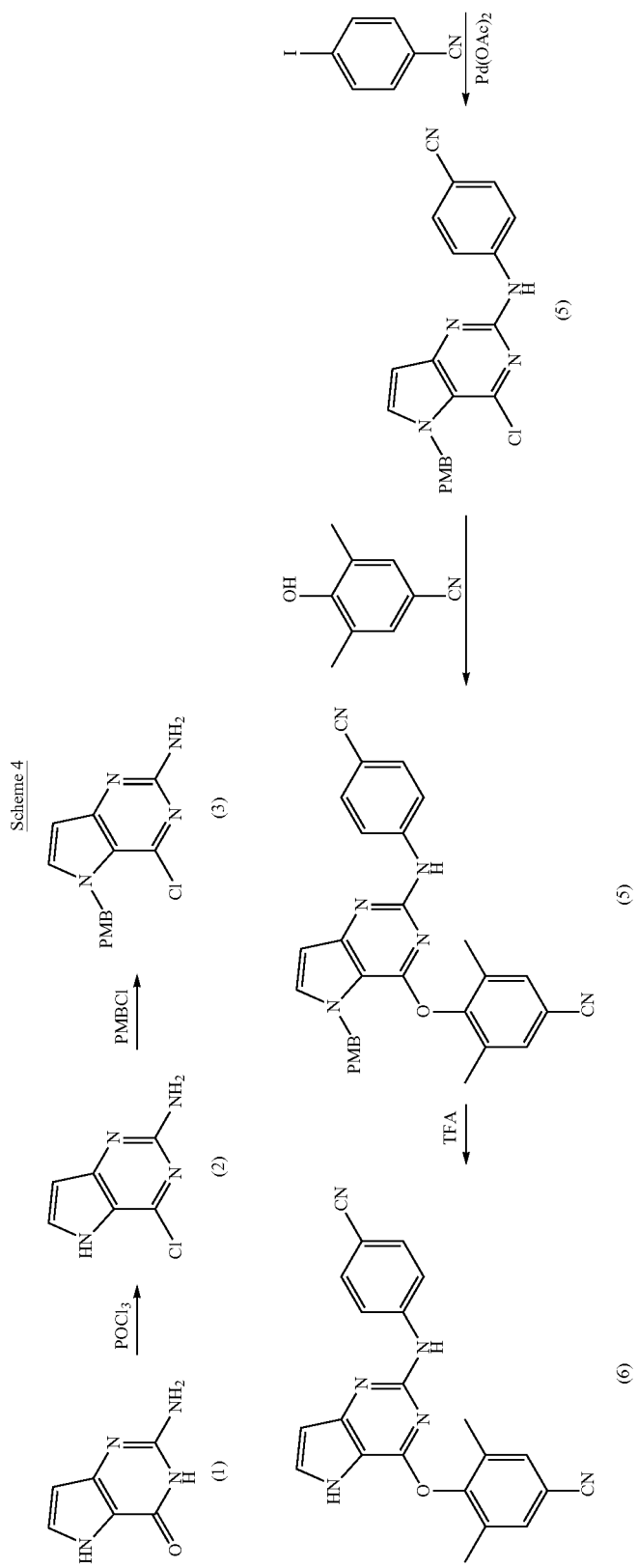

The 7-deazapurines of this invention are prepared by the procedure of Scheme 5. The starting material can be synthesized by the condensation of 2,6-diamino-1,2-dihydro[3H] pyrimidin-4-one with chloroacetaldehyde followed by treatment with phosphorus oxychloride, as indicated in Examples 1 and 3.

Scheme 5

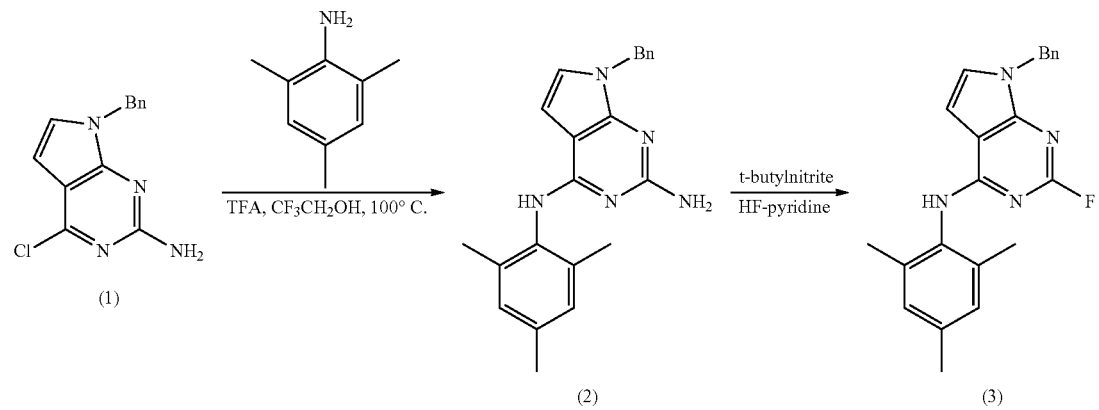

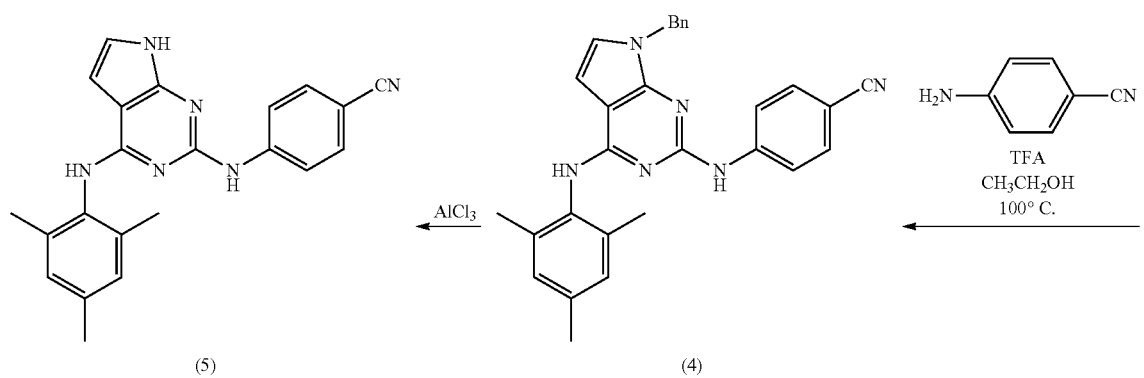

The purine compounds of this invention can be synthesized by strategies similar to those provided above, using $N^7$-benzyl-2,6-dichloropurine as the starting material. This procedure is illustrated in WO 2005/028479.

Example 1

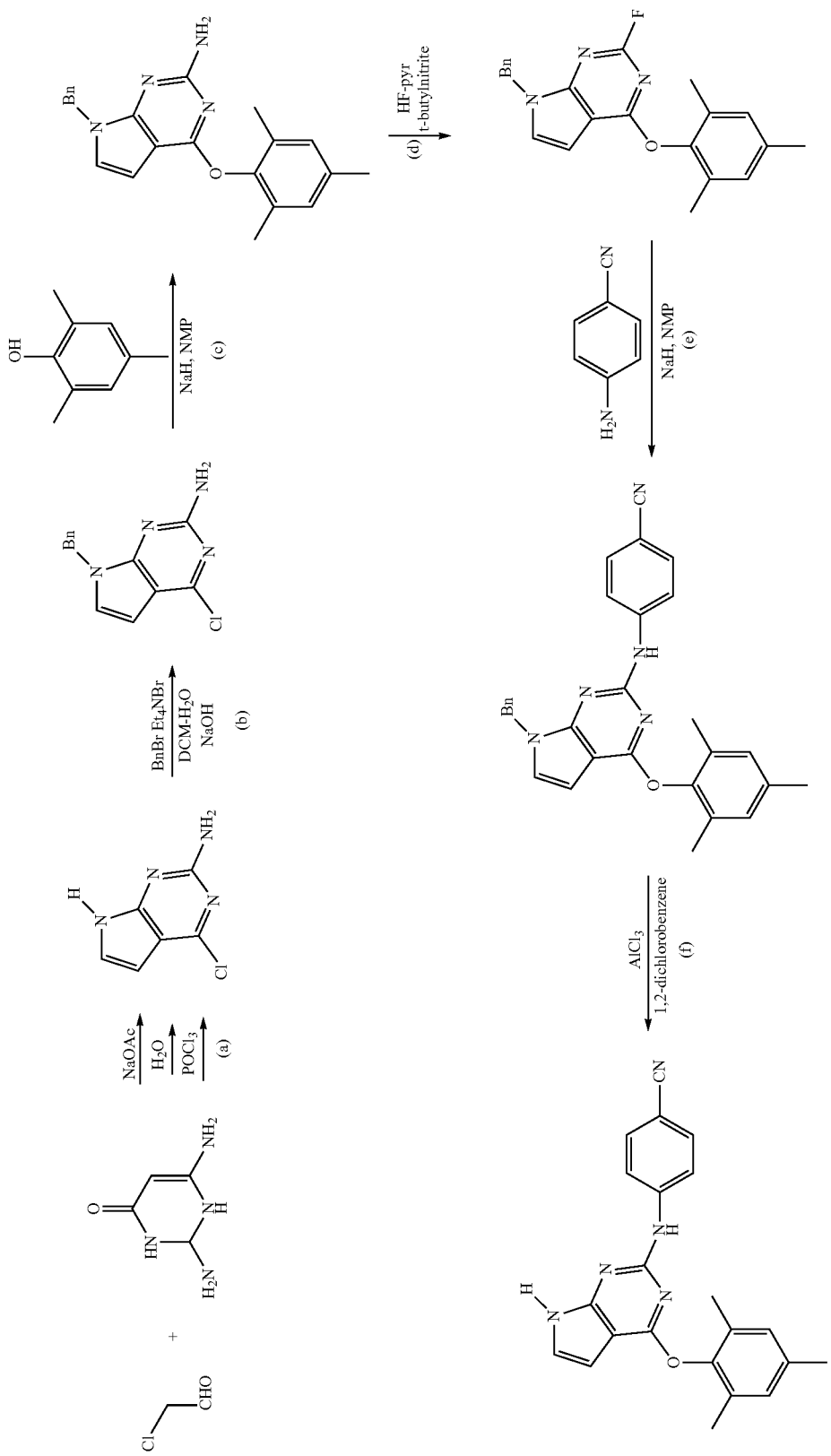

Step A1

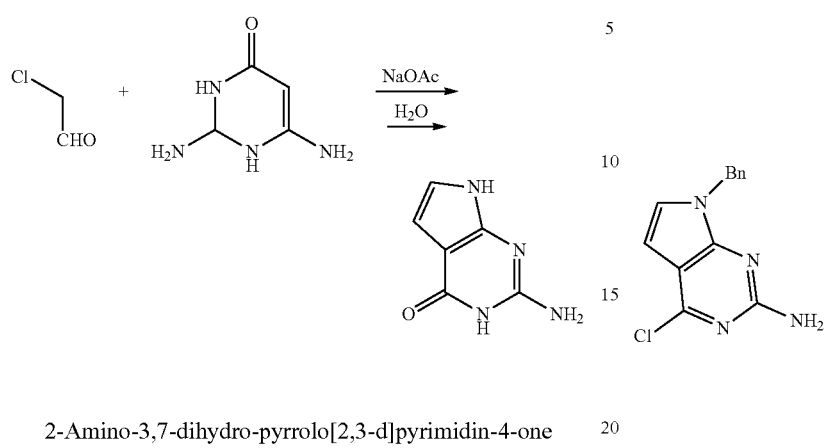

2-Amino-3,7-dihydro-pyrrolo[2,3-d]pyrimidin-4-one

To a mixture of 2,4-diamino-6-hydroxypyrimidine (20.0 g, 159 mmol) and NaOAc (26.0 g, 317 mmol) in $H_2O$ (300 mL) at 65° C. was added a solution of chloroacetaldehyde (22.0 mL, 50% in $H_2O$, 173 mmol) in $H_2O$ (22 mL) dropwise for 90 min. The mixture was stirred at 65° C. for an additional 2 h and cooled to room temperature. The reaction mixture was concentrated in vacuo to one third of its original volume and stored at 4° C. for 16 h. The light pink precipitates were filtered, washed with an ice cold $H_2O$ (5 mL), and dried under high vacuum for 16 h. The precipitates were placed in Soxhlet extractor and refluxed with methanol (200 mL) for 24 h. The methanol was concentrated to give 13.3 g (56%) of 2-amino-3,7-dihydro-pyrrolo[2,3-d]pyrimidin-4-one as a light pink solid.

Step A2

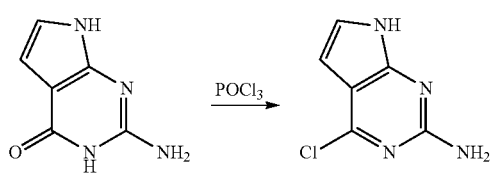 [SMILES: Nc1nc2[nH]ccc2c(=O)[nH]1 ; "POCl3" ; Nc1nc(Cl)c2cc[nH]c2n1]

4-Chloro-7H-pyrrolo[2,3-d]pyrimidin-2-ylamine

To a solution of 2-amino-3,7-dihydro-pyrrolo[2,3-d]pyrimidin-4-one (5.00 g, 33.3 mmol), dimethylaniline (4.22 mL, 41.0 mmol) and benzyltriethylammonium chloride (15.2 g, 66.6 mmol) in acetonitrile (25 mL) at room temperature under argon was added $POCl_3$ (18.6 mL, 200 mmol) dropwise for 30 min. The mixture was refluxed at 85° C. for 3 h and cooled to room temperature. The reaction was concentrated in vacuo to brown oil and to the oil was added an ice cold $H_2O$ (10 mL). The pH of the solution was adjusted to 5 by the addition of an aqueous $NH_4OH$ solution. Silica gel chromatography ($CH_2Cl_2$:MeOH=95:5) yielded 2.53 g (45%) of 4-chloro-7H-pyrrolo[2,3-d]pyrimidin-2-ylamine as a light yellow solid.

The product was then benzylated at $N^7$ using standard techniques.

Step C

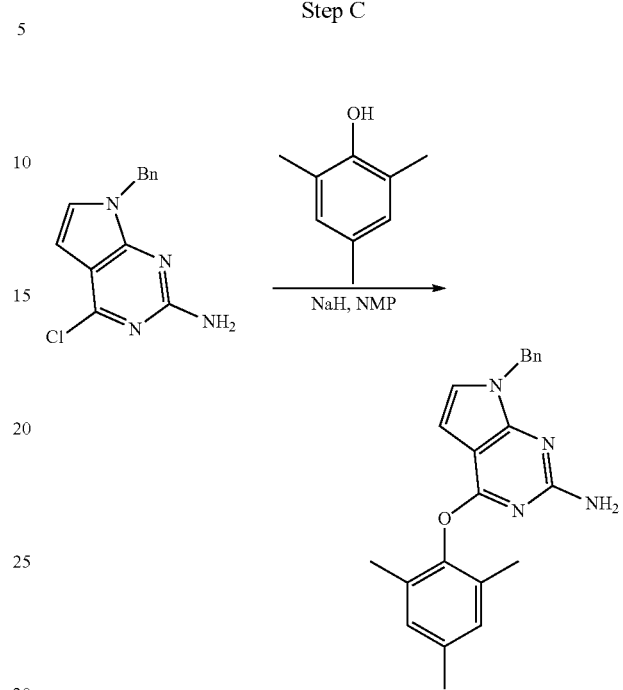

7-benzyl-4-(2,4,6-trimethyl-phenoxy)-7H-pyrrolo[2,3-d]pyrimidin-2-ylamine

To a solution of 2,4,6-trimethylphenol (161 mg, 1.16 mmol) in 1-methyl-2-pyrridone (2 mL) in a sealed tube was added NaH (46 mg, 1.16 mmol). The reaction mixture was stirred at room temperature for 15 min and a solution of 7-benzyl-4-chloro-7H-pyrrolo[2,3-d]pyrimidin-2-ylamine (100 mg, 0.39 mmol) in 1-methyl-2-pyrridone (1 mL) was added to the mixture. The mixture was heated at 150° C. for 16 h and cooled to room temperature. The reaction mixture was poured into ice water and extracted with EtOAc (2×20 mL). The combined organic solution was washed with $H_2O$ (20 mL) and brine (20 mL), dried with $Na_2SO_4$, and concentrated to dryness. Silica gel chromatography (Hexanes:EtOAc=75:25) yielded 107 mg (77%) of 7-benzyl-4-(2,4,6-trimethyl-phenoxy)-7H-pyrrolo[2,3-d]pyrimidin-2-ylamine.

Step D

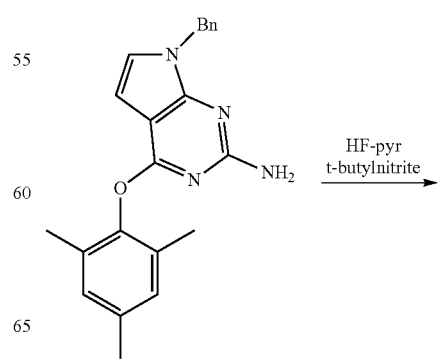

7-benzyl-2-fluoro-4-(2,4,6-trimethyl-phenoxy)-7H-pyrrolo[2,3-d]pyrimidine

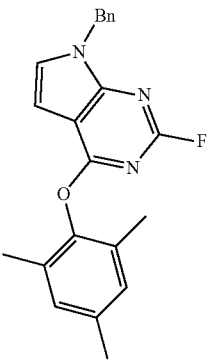

To 7-benzyl-4-(2,4,6-trimethyl-phenoxy)-7H-pyrrolo[2,3-d]pyrimidin-2-ylamine (105 mg, 0.29 mmol) in a polyethylene flask at −50° C. under argon was added 60% HF in pyridine (12 mL). To the resulting solution tert-butylnitrite (0.052 mL, 0.44 mmol) was added dropwise for 5 min. The reaction was warmed to −40° C. and stirred for 30 min at the temperature. The reaction mixture was diluted with CHCl$_3$ (100 mL) and poured into K$_2$CO$_3$ (3 g) in a beaker. Ice water (50 mL) was carefully added to the mixture. The CHCl$_3$ layer was separated, washed with aqueous NaHCO$_3$ solution (20 mL) and brine (20 mL), dried with Na$_2$SO$_4$, and concentrated to dryness. Silica gel chromatography (Hexanes:EtOAc=75:25) yielded 72 mg (68%) of 7-benzyl-2-fluoro-4-(2,4,6-trimethyl-phenoxy)-7H-pyrrolo[2,3-d]pyrimidine as a light yellow solid.

Step E

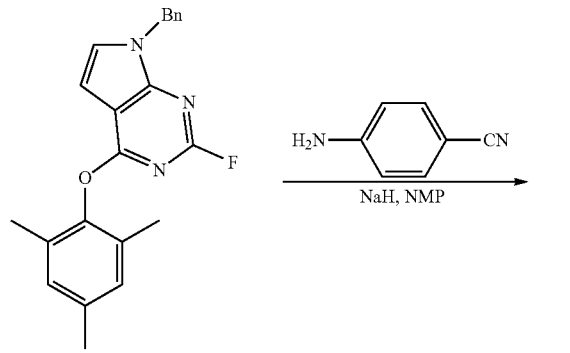

4-[7-benzyl-4-(2,4,6-trimethyl-phenoxy)-7H-pyrrolo[2,3-d]pyrimidin-2-ylamino]-benzonitrile To a solution of 4-aminobenzonitrile (101 mg, 0.86 mmol) in 1-methyl-2-pyrridone (1 mL) was added NaH (34 mg, 0.86 mmol). The reaction mixture was stirred at room temperature for 15 min and a solution of 7-benzyl-2-fluoro-4-(2,4,6-trimethyl-phenoxy)-7H-pyrrolo[2,3-d]pyrimidine (62 mg, 0.17 mmol) in 1-methyl-2-pyrridone (1 mL) was added to the mixture. The mixture was stirred at room temperature for 1 h, poured into ice water, and extracted with EtOAc (2×20 mL). The combined organic solution was washed with H$_2$O (20 mL) and brine (20 mL), dried with Na$_2$SO$_4$, and concentrated to dryness. Silica gel chromatography (Hexanes:EtOAc=75:25) yielded 64 mg (82%) of 4-[7-benzyl-4-(2,4,6-trimethyl-phenoxy)-7H-pyrrolo[2,3-d]pyrimidin-2-ylamino]-benzonitrile.

Step F

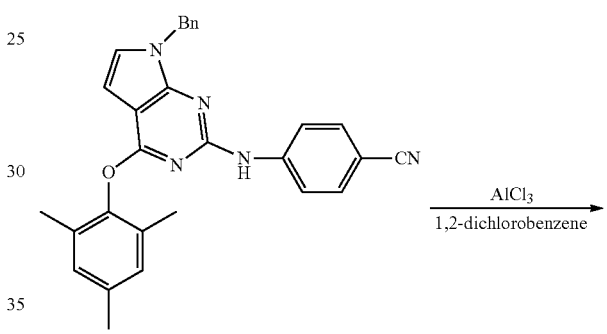

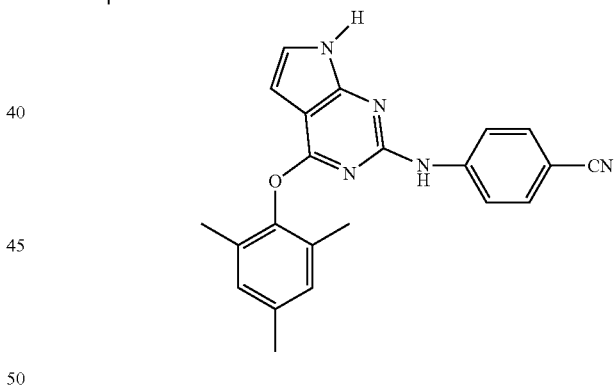

4-[4-(2,4,6-Trimethyl-phenoxy)-7H-pyrrolo[2,3-d]pyrimidin-2-ylamino]-benzonitrile To a solution of 4-[7-benzyl-4-(2,4,6-trimethyl-phenoxy)-7H-pyrrolo[2,3-d]pyrimidin-2-ylamino]-benzonitrile (38 mg, 0.083 mmol) in 1,2-dichlorobenzene (1 mL) was added aluminum chloride (55 mg, 0.42 mmol). The reaction mixture was stirred at 160° C. for 4 h and cooled to room temperature. The mixture was poured into ice water and extracted with CH$_2$Cl$_2$ (2×10 mL). The combined organic solution was washed with brine (10 mL), dried with Na$_2$SO$_4$, and concentrated to dryness. Silica gel chromatography (Hexanes:EtOAc=50:50) yielded 15 mg (49%) of 4-[4-(2,4,6-trimethyl-phenoxy)-7H-pyrrolo[2,3-d]pyrimidin-2-ylamino]-benzonitrile as a tan solid.

Example 2

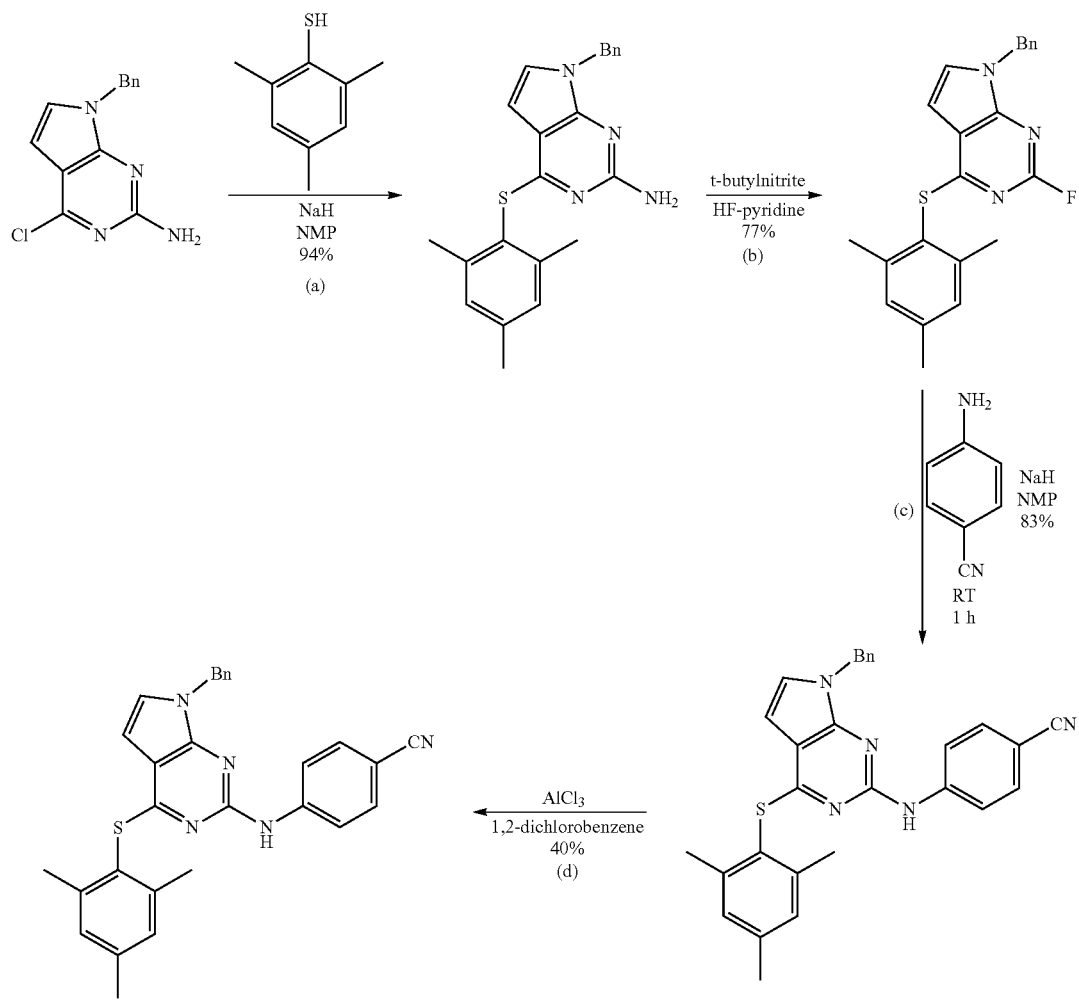

Step A

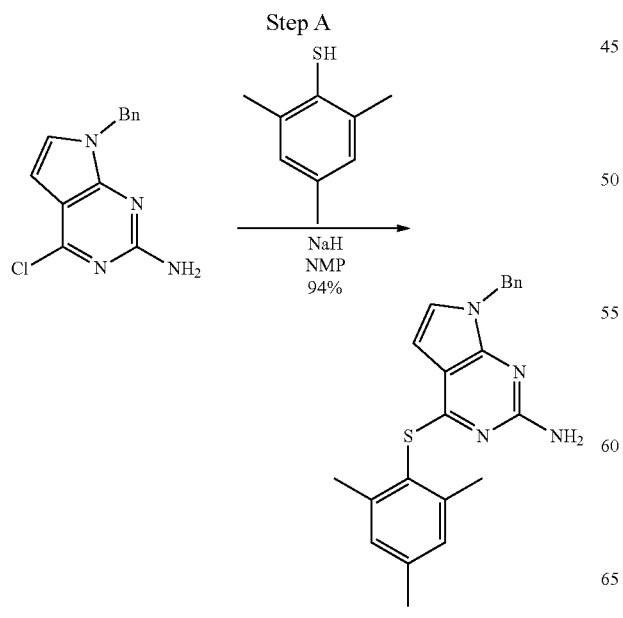

7-benzyl-4-(2,4,6-trimethyl-phenylsulfanyl)-7H-pyrrolo[2,3-d]pyrimidin-2-ylamine To a solution of 2,4,6-trimethylbenzene-1-thiol (231 mg, 1.52 mmol) in 1-methyl-2-pyrridone (2 mL) was added NaH (58 mg, 1.52 mmol). The reaction mixture was stirred at room temperature for 15 min and a solution of 7-benzyl-4-chloro-7H-pyrrolo[2,3-d]pyrimidin-2-ylamine (131 mg, 0.51 mmol) in 1-methyl-2-pyrridone (2 mL) was added to the mixture. The mixture was heated at 60° C. for 16 h and cooled to room temperature. The reaction was poured into ice water and extracted with EtOAc (2×20 mL). The combined organic solution was washed with $H_2O$ (20 mL) and brine (20 mL), dried with $Na_2SO_4$, and concentrated to dryness. Silica gel chromatography (Hexanes:EtOAc=75:25) yielded 180 mg (94%) of 7-benzyl-4-(2,4,6-trimethyl-phenylsulfanyl)-7H-pyrrolo[2,3-d]pyrimidin-2-ylamine.

Step B

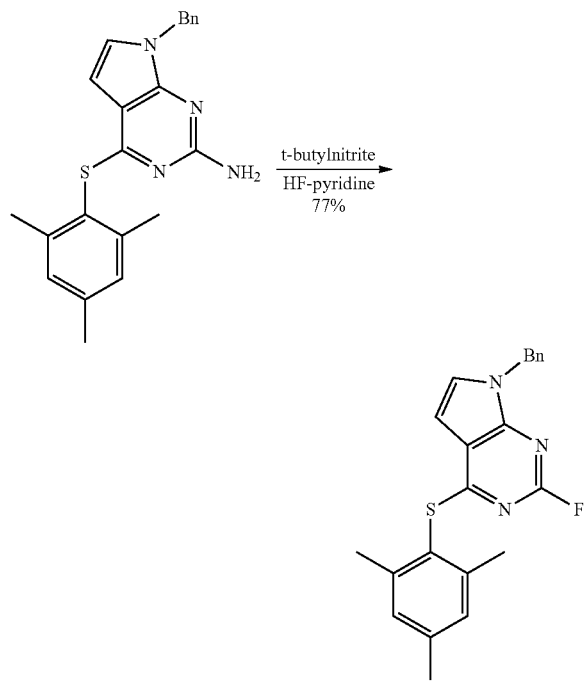

7-benzyl-2-fluoro-4-(2,4,6-trimethyl-phenylsulfanyl)-7H-pyrrolo[2,3-d]pyrimidine To 7-benzyl-4-(2,4,6-trimethyl-phenylsulfanyl)-7H-pyrrolo[2,3-d]pyrimidin-2-ylamine (155 mg, 0.41 mmol) in a polyethylene flask at −50° C. under argon was added 60% HF in pyridine (12 mL). To the solution was added tert-butylnitrite (0.074 mL, 0.62 mmol) dropwise for 5 min. The reaction was warmed to −40° C. and stirred for 30 min at the temperature. The reaction was diluted with CHCl$_3$ (100 mL) and poured into K$_2$CO$_3$ (3 g) in a beaker. To the mixture was carefully added ice water (50 mL). The CHCl$_3$ layer was separated, washed with aqueous NaHCO$_3$ solution (20 mL) and brine (20 mL), dried with Na$_2$SO$_4$, and concentrated to dryness. Silica gel chromatography (Hexanes:EtOAc=75:25) yielded 118 mg (77%) of 7-benzyl-2-fluoro-4-(2,4,6-trimethyl-phenylsulfanyl)-7H-pyrrolo[2,3-d]pyrimidine as a yellow solid.

Step C

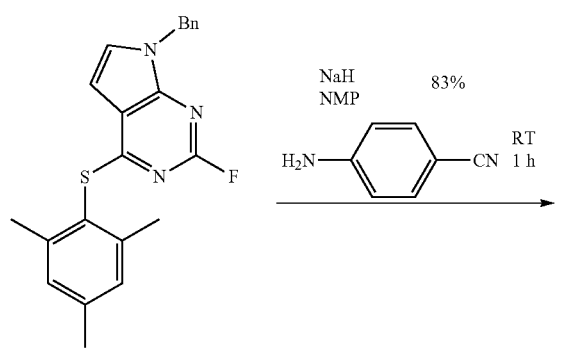

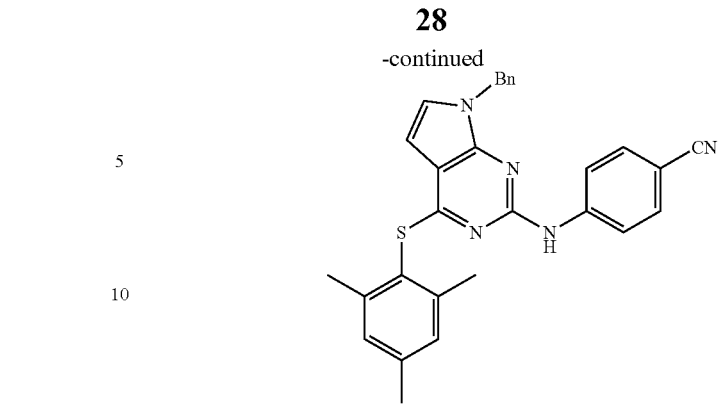

4-[7-benzyl-4-(2,4,6-trimethyl-phenylsulfanyl)-7H-pyrrolo[2,3-d]pyrimidin-2-ylamino]-benzonitrile To a solution of 4-aminobenzonitrile (184 mg, 1.56 mmol) in 1-methyl-2-pyrridone (2 mL) was added NaH (62 mg, 1.56 mmol). The reaction mixture was stirred at room temperature for 15 min and a solution of 7-benzyl-2-fluoro-4-(2,4,6-trimethyl-phenylsulfanyl)-7H-pyrrolo[2,3-d]pyrimidine (118 mg, 0.31 mmol) in 1-methyl-2-pyrridone (2 mL) was added to the mixture. The mixture was stirred at room temperature for 4 h, then poured into ice water and extracted with EtOAc (2×20 mL). The combined organic solution was washed with H$_2$O (20 mL) and brine (20 mL), dried with Na$_2$SO$_4$, and concentrated to dryness. Silica gel chromatography (Hexanes:EtOAc=75:25) yielded 123 mg (83%) of 4-[7-benzyl-4-(2,4,6-trimethyl-phenylsulfanyl)-7H-pyrrolo[2,3-d]pyrimidin-2-ylamino]-benzonitrile.

Step D

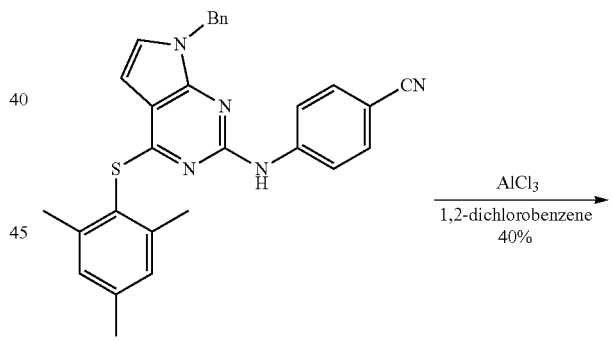

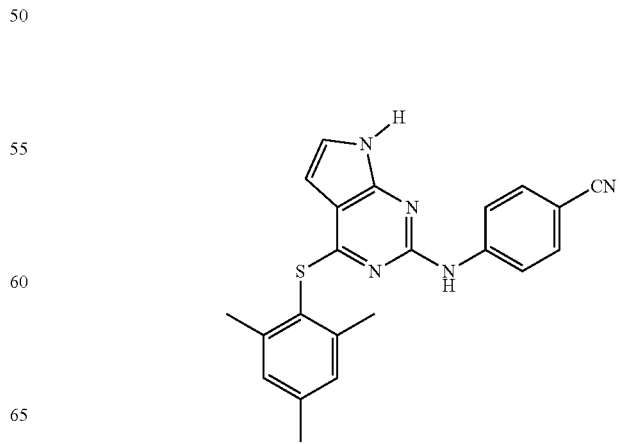

4-[4-(2,4,6-Trimethyl-phenylsulfanyl)-7H-pyrrolo[2,3-d]pyrimidin-2-ylamino]-benzonitrile To a solution of 4-[7-benzyl-4-(2,4,6-trimethyl-phenylsulfanyl)-7H-pyrrolo[2,3-d]pyrimidin-2-ylamino]-benzonitrile (103 mg, 0.21 mmol) in 1,2-dichlorobenzene (2 mL) was added aluminum chloride (87 mg, 0.65 mmol). The reaction mixture was stirred at 160° C. for 1.5 h and cooled to room temperature. The mixture was poured into ice water and extracted with $CH_2Cl_2$ (2×10 mL). The combined organic solution was washed with brine (10 mL), dried with $Na_2SO_4$, and concentrated to dryness. Silica gel chromatography (Hexanes:EtOAc=50:50) yielded 28 mg (34%) of 4-[4-(2,4,6-trimethyl-phenylsulfanyl)-7H-pyrrolo[2,3-d]pyrimidin-2-ylamino]-benzonitrile as a tan solid.

Example 3

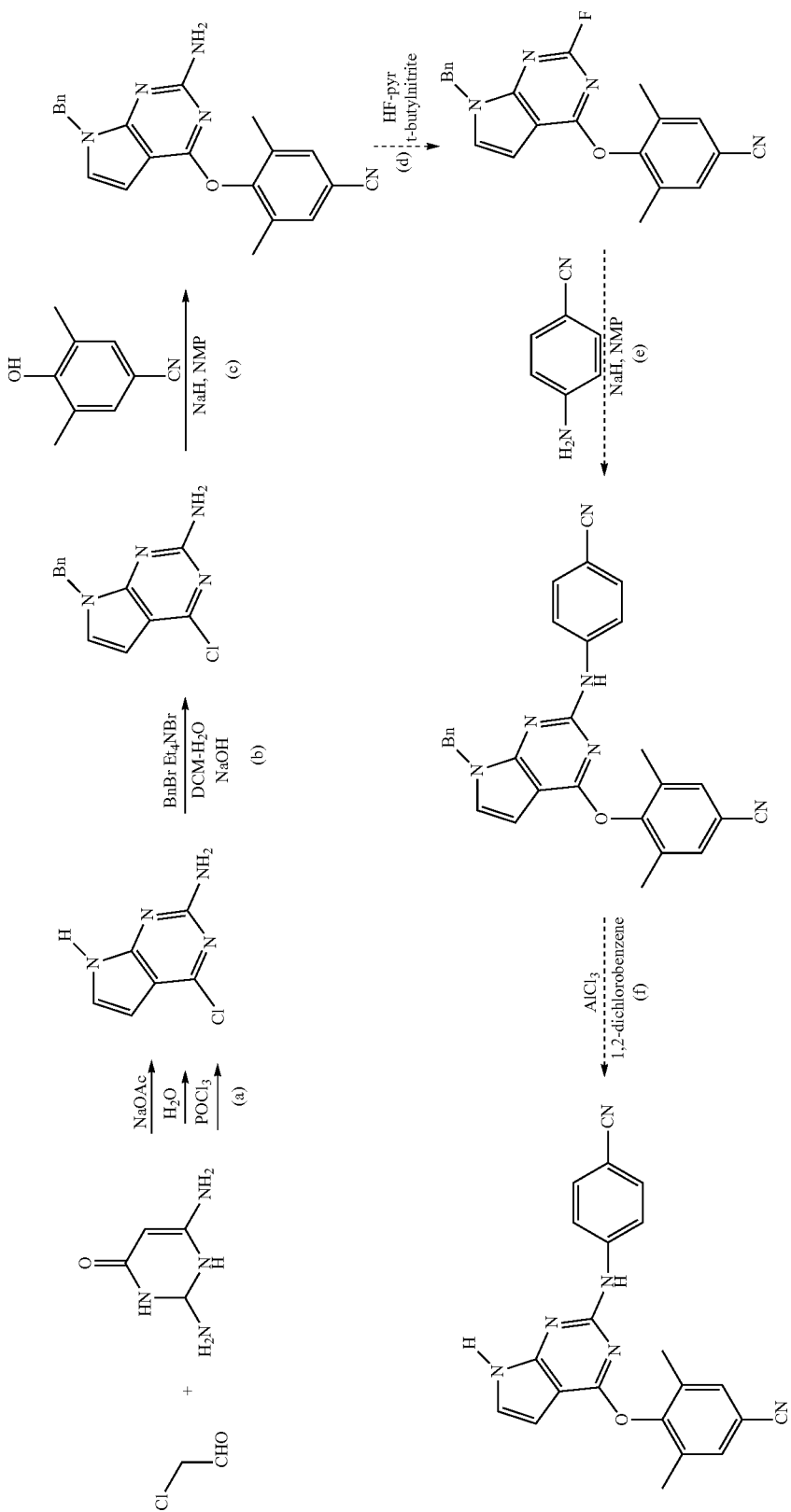

Steps A and B as in Example 1
Step C

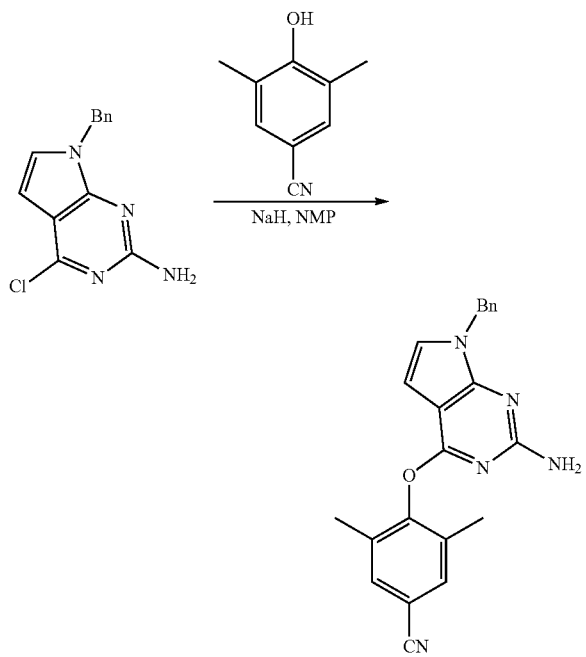

4-(2-Amino-7-benzyl-7H-pyrrolo[2,3-d]pyrimidin-4-yloxy)-3,5-dimethyl-benzonitrile To a solution of 4-hydroxy-3,5-dimethylbenzonitrile (1.62 mg, 11.0 mmol) in 1-methyl-2-pyrridone (5 mL) in a sealed tube was added NaH (441 mg, 11.0 mmol). The reaction mixture was stirred at room temperature for 15 min and a solution of 7-benzyl-4-chloro-7H-pyrrolo[2,3-d]pyrimidin-2-ylamine (950 mg, 3.67 mmol) in 1-methyl-2-pyrridone (5 mL) was added to the mixture. The mixture was heated at 150° C. for 16 h and cooled to room temperature. The reaction was poured into ice water and extracted with EtOAc (2×50 mL). The combined organic solution was washed with H₂O (50 mL) and brine (50 mL), dried with Na₂SO₄, and concentrated to dryness. Silica gel chromatography (Hexanes:EtOAc=75:25) yielded 1.12 mg (83%) of 4-(2-amino-7-benzyl-7H-pyrrolo[2,3-d]pyrimidin-4-yloxy)-3,5-dimethyl-benzonitrile.

Step D

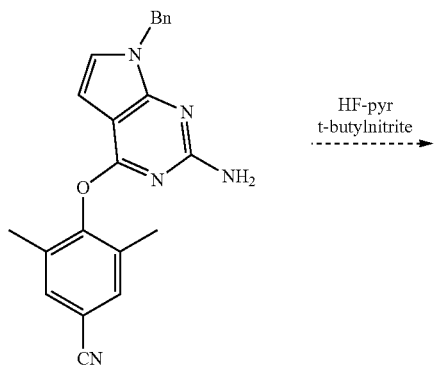

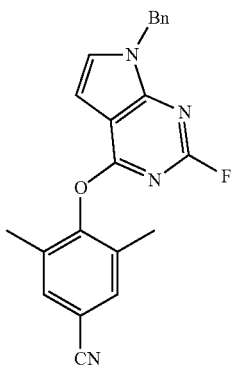

4-(7-benzyl-2-fluoro-7H-pyrrolo[2,3-d]pyrimidin-4-yloxy)-3,5-dimethyl-benzonitrile To 4-(2-amino-7-benzyl-7H-pyrrolo[2,3-d]pyrimidin-4-yloxy)-3,5-dimethyl-benzonitrile (70 mg, 0.19 mmol) in a polyethylene flask at −50° C. under argon was added 60% HF in pyridine (12 mL). To the solution was added tert-butylnitrite (0.068 mL, 0.57 mmol) dropwise for 5 min. The reaction was warmed to −40° C. and stirred for 30 min at the temperature. The reaction was diluted with CHCl₃ (100 mL) and poured into K₂CO₃ (3 g) in a beaker. To the mixture was carefully added ice water (50 mL). The CHCl₃ layer was separated, washed with aqueous NaHCO₃ solution (20 mL) and brine (20 mL), dried with Na₂SO₄, and concentrated to dryness. Silica gel chromatography (Hexanes:EtOAc=75:25) yielded 36 mg (51%) of 4-(7-benzyl-2-fluoro-7H-pyrrolo[2,3-d]pyrimidin-4-yloxy)-3,5-dimethyl-benzonitrile.

Step E

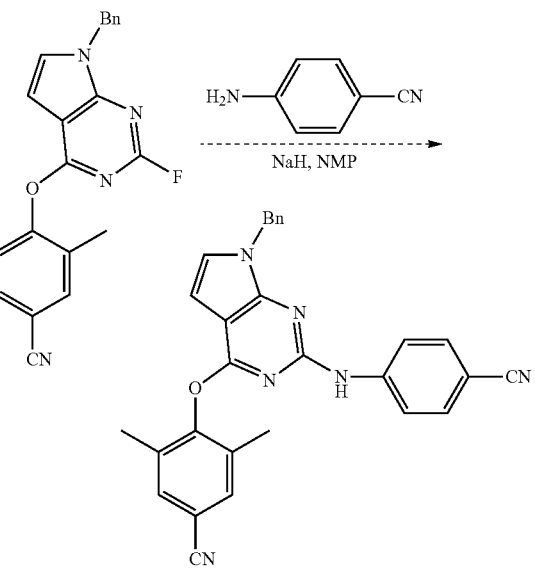

4-[7-benzyl-2-(4-cyano-phenylamino)-7H-pyrrolo[2,3-d]pyrimidin-4-yloxy]-3,5-dimethyl-benzonitrile To a solution of 4-aminobenzonitrile (54 mg, 0.46 mmol) in 1-methyl-2-pyrridone (1 mL) was added NaH (18 mg, 0.46 mmol). The reaction mixture was stirred at room temperature for 15 min and a solution of 4-(7-benzyl-2-fluoro-7H-pyrrolo[2,3-d]pyrimidin-4-yloxy)-3,5-dimethyl-benzonitrile (34 mg, 0.091 mmol) in 1-methyl-2-pyrridone (1 mL) was added to the mixture. The mixture was stirred at room temperature for 1 h, poured into ice water, and extracted with EtOAc (2×20 mL). The combined organic solution was washed with H₂O (20 mL) and brine (20 mL), dried with Na₂SO₄, and concentrated to dryness. Silica gel chromatography (Hexanes:EtOAc=75:25) yielded 28 mg (65%) of 4-[7-benzyl-2-(4-cyano-phenylamino)-7H-pyrrolo[2,3-d]pyrimidin-4-yloxy]-3,5-dimethyl-benzonitrile.

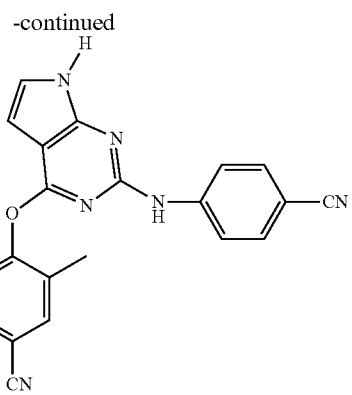

4-[2-(4-Cyano-phenylamino)-7H-pyrrolo[2,3-d]pyrimidin-4-yloxy]-3,5-dimethyl-benzonitrile To a solution of 4-[7-benzyl-2-(4-cyano-phenylamino)-7H-pyrrolo[2,3-d]pyrimidin-4-yloxy]-3,5-dimethyl-benzonitrile (28 mg, 0.060 mmol) in 1,2-dichlorobenzene (1 mL) was added aluminum chloride (40 mg, 0.30 mmol). The reaction mixture was stirred at 160° C. for 45 min and cooled to room temperature. The mixture was poured into ice water and extracted with CH₂Cl₂ (2×10 mL). The combined organic solution was washed with brine (10 mL), dried with Na₂SO₄, and concentrated to dryness. Silica gel chromatography (Hexanes:EtOAc=50:50) yielded 6 mg (27%) of 4-[2-(4-cyano-phenylamino)-7l'-pyrrolo[2,3-d]pyrimidin-4-yloxy]-3,5-dimethyl-benzonitrile as a tan solid.

Step F

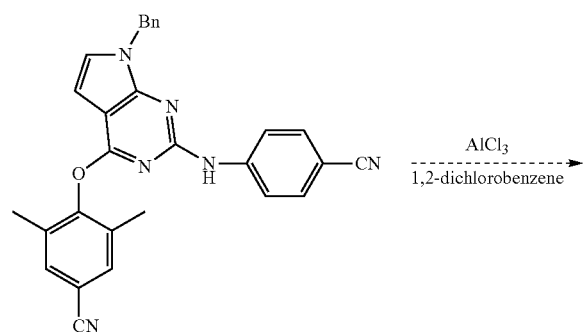

Example 4

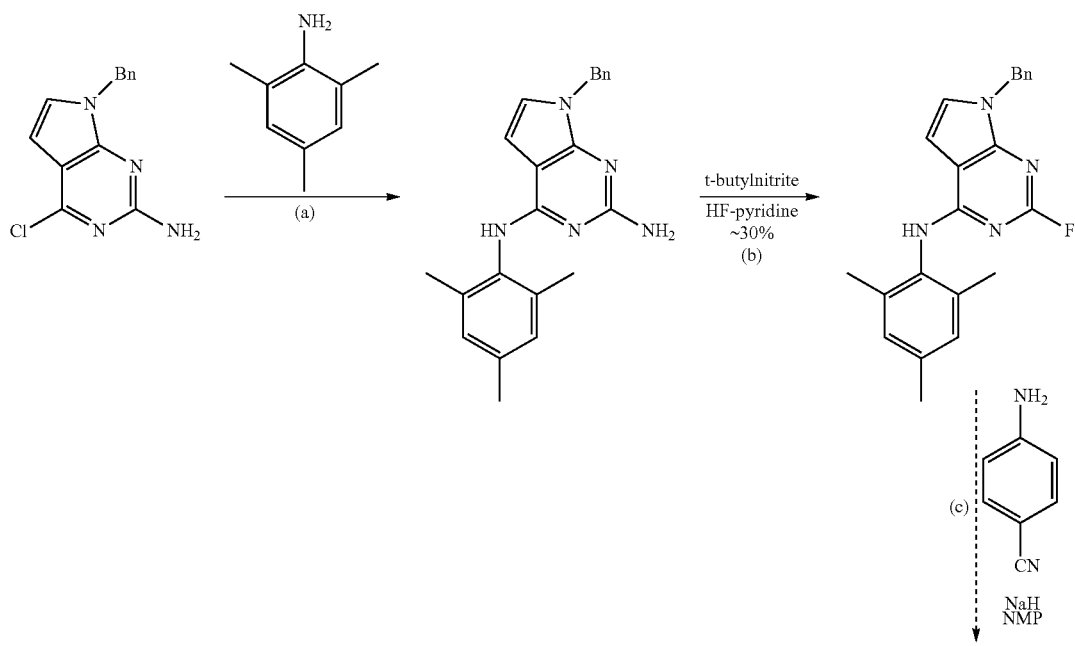

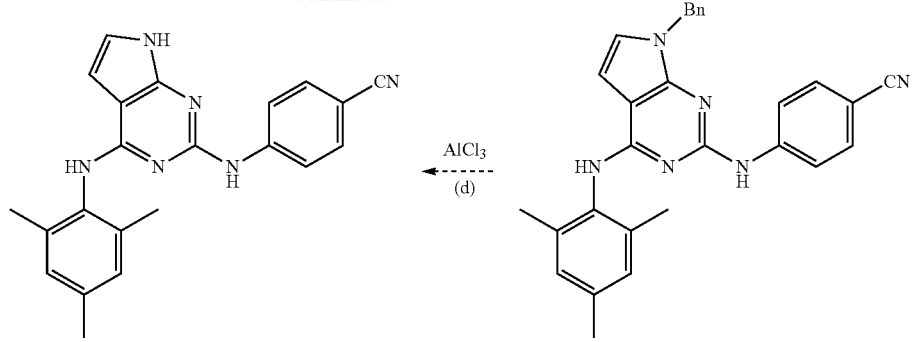

Step A

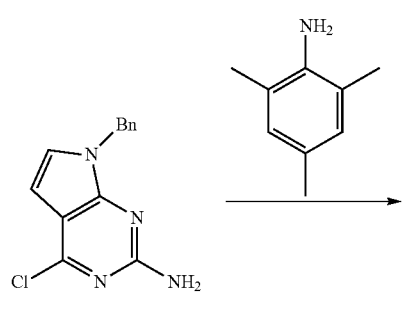

7-benzyl-N4-(2,4,6-trimethyl-phenyl)-7H-pyrrolo[2,3-d]pyrimidine-2,4-diamine

To a suspension of 7-benzyl-4-chloro-7H-pyrrolo[2,3-d]pyrimidin-2-ylamine (200 mg, 0.78 mmol) and 2,4,6-trimethylaniline (0.44 mL, 3.08 mmol) in 2,2,2-trifluoroethanol (4 mL) was added trifluoroacetic acid (0.48 mL, 6.24 mmol). The resulting solution was heated at 100° C. for 2 days and cooled to room temperature. The reaction was concentrated to brown oil and diluted with CH₂Cl₂ (30 mL). The organic solution was washed with aqueous NaHCO₃ solution (20 mL) and brine (20 mL), dried with Na₂SO₄, and concentrated to dryness. Silica gel chromatography (CH₂Cl₂:MeOH=95:5) yielded 251 mg (90%) of 7-benzyl-N4-(2,4,6-trimethyl-phenyl)-7H-pyrrolo[2,3-d]pyrimidine-2,4-diamine.

Step B

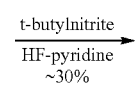

(7-benzyl-2-fluoro-7H-pyrrolo[2,3-d]pyrimidin-4-yl)-(2,4,6-trimethyl-phenyl)-amine To 7-benzyl-N4-(2,4,6-trimethyl-phenyl)-7H-pyrrolo[2,3-d]pyrimidine-2,4-diamine (251 mg, 0.70 mmol) in a polyethylene flask at −50° C. under argon was added 60% HF in pyridine (24 mL). To the solution was added tert-butylnitrite (0.42 mL, 3.5 mmol) dropwise for 10 min. The reaction was warmed to −40° C. and stirred for 30 min at the temperature. The reaction was diluted with CHCl₃ (200 mL) and poured into K₂CO₃ (6 g) in a beaker. To the mixture was carefully added ice water (100 mL). The CHCl₃ layer was separated, washed with aqueous NaHCO₃ solution (40 mL) and brine (40 mL), dried with Na₂SO₄, and concentrated to dryness. Silica gel chromatography (Hexanes:EtOAc=75:25) yielded 56 mg (22%) of (7-benzyl-2-fluoro-7H-pyrrolo[2,3-d]pyrimidin-4-yl)-(2,4,6-trimethyl-phenyl)-amine.

Step C

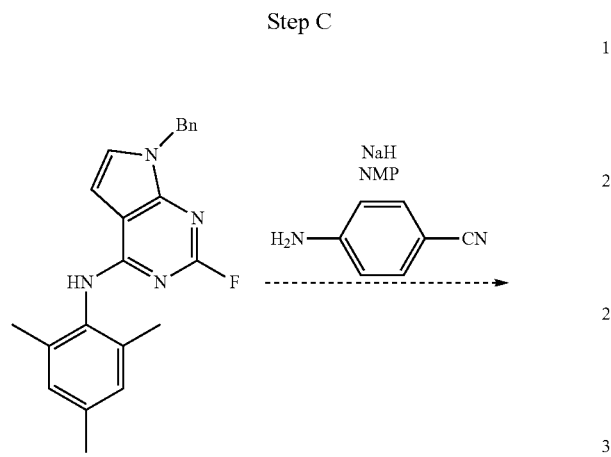

4-[7-benzyl-4-(2,4,6-trimethyl-phenylamino)-7H-pyrrolo[2,3-d]pyrimidin-2-ylamino]-benzonitrile To a suspension of (7-benzyl-2-fluoro-7H-pyrrolo[2,3-d]pyrimidin-4-yl)-(2,4,6-trimethyl-phenyl)-amine (42 mg, 0.12 mmol) and 4-aminobenzonitrile (55 mg, 0.47 mmol) in 2,2,2-trifluoroethanol (4 mL) was added trifluoroacetic acid (0.072 mL, 0.94 mmol). The resulting solution was heated at 90° C. for 16 h, then cooled to room temperature. The reaction was concentrated to produce a brown oil and diluted with CH₂Cl₂ (30 mL). The organic solution was washed with H₂O (20 mL) and brine (20 mL), dried with Na₂SO₄, and concentrated to dryness. Silica gel chromatography (Hexanes:EtOAc=75:25) yielded 34 mg (64%) of 4-[7-benzyl-4-(2,4,6-trimethyl-phenylamino)-7H-pyrrolo[2,3-d]pyrimidin-2-ylamino]-benzonitrile.

Step D

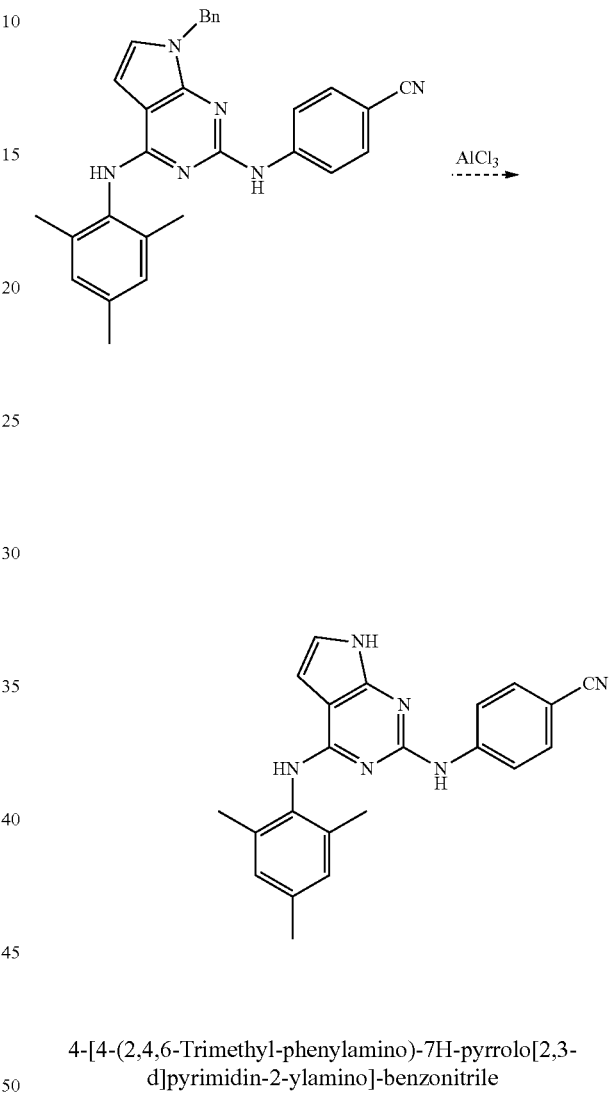

4-[4-(2,4,6-Trimethyl-phenylamino)-7H-pyrrolo[2,3-d]pyrimidin-2-ylamino]-benzonitrile To a solution of 4-[7-benzyl-4-(2,4,6-trimethyl-phenylamino)-7H-pyrrolo[2,3-d]pyrimidin-2-ylamino]-benzonitrile (34 mg, 0.074 mmol) in 1,2-dichlorobenzene (1 mL) was added aluminum chloride (50 mg, 0.37 mmol). The reaction mixture was stirred at 160° C. for 2 h and cooled to room temperature. The mixture was poured into ice water and extracted with CHCl₃ (2×10 mL). The combined organic solution was washed with brine (10 mL), dried with Na₂SO₄, and concentrated to dryness. Silica gel chromatography (CH₂Cl₂:Acetone=90:10) yielded 5 mg (19%) of 4-[4-(2,4,6-trimethyl-phenylamino)-7H-pyrrolo[2,3-d]pyrimidin-2-ylamino]-benzonitrile as a tan solid.

Example 5

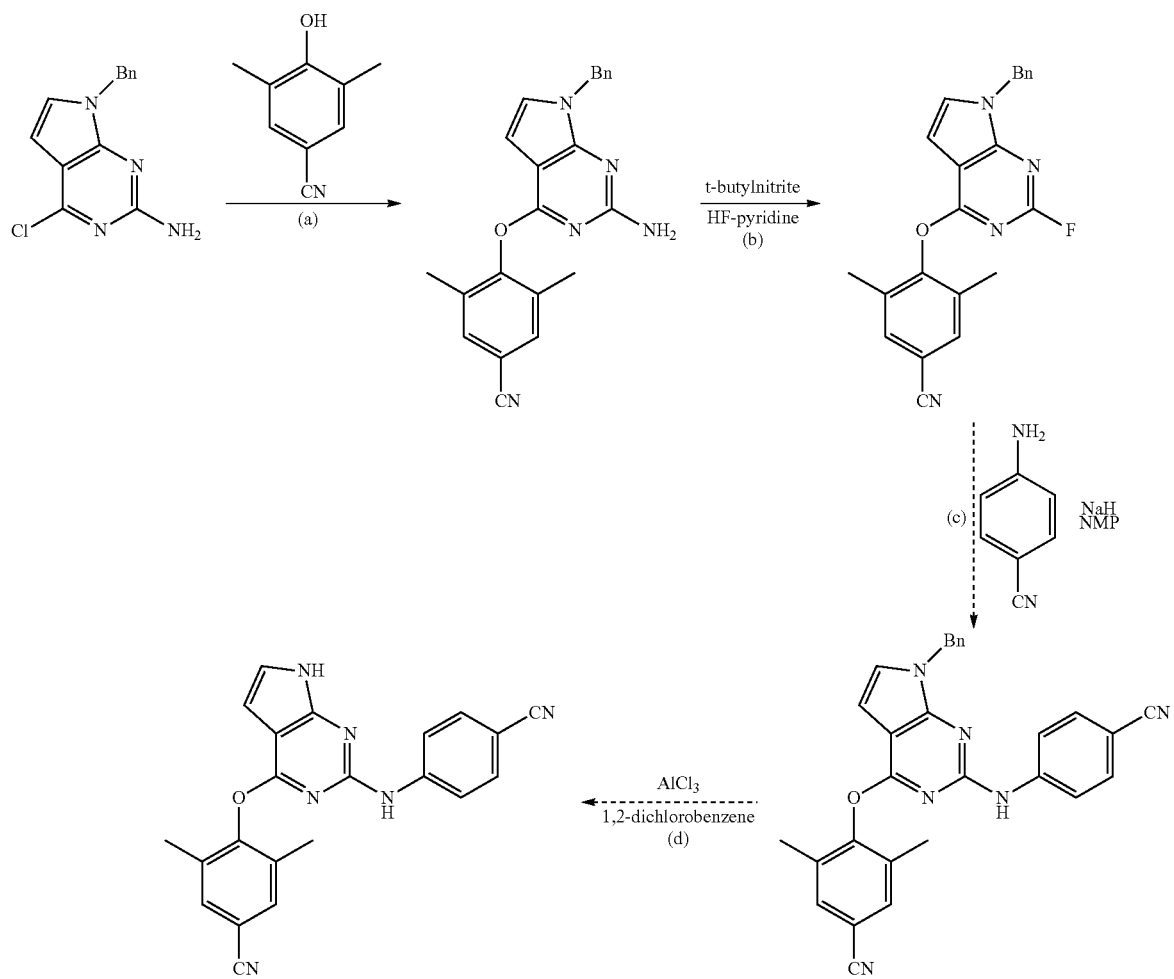

Step A

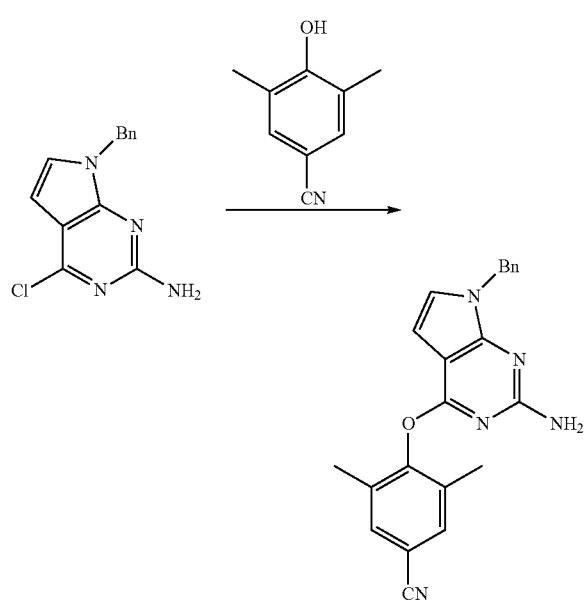

4-(2-Amino-7-benzyl-7H-pyrrolo[2,3-d]pyrimidin-4-yloxy)-3,5-dimethyl-benzonitrile To a solution of 4-hydroxy-3,5-dimethylbenzonitrile (1.62 mg, 11.0 mmol) in 1-methyl-2-pyrridone (5 mL) in a sealed tube was added NaH (441 mg, 11.0 mmol). The reaction mixture was stirred at room temperature for 15 min and a solution of 7-benzyl-4-chloro-7H-pyrrolo[2,3-d]pyrimidin-2-ylamine (950 mg, 3.67 mmol) in 1-methyl-2-pyrridone (5 mL) was added to the mixture. The mixture was heated at 150° C. for 16 h and cooled to room temperature. The reaction was poured into ice water and extracted with EtOAc (2×50 mL). The combined organic solution was washed with H₂O (50 mL) and brine (50 mL), dried with Na₂SO₄, and concentrated to dryness. Silica gel chromatography (Hexanes:EtOAc=75:25) yielded 1.12 mg (83%) of 4-(2-amino-7-benzyl-7H-pyrrolo[2,3-d]pyrimidin-4-yloxy)-3,5-dimethyl-benzonitrile.

Step B

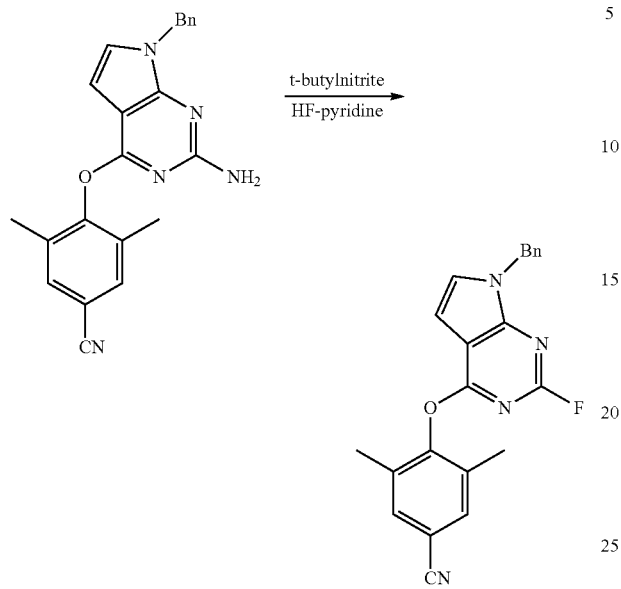

4-(7-benzyl-2-fluoro-7H-pyrrolo[2,3-d]pyrimidin-4-yloxy)-3,5-dimethyl-benzonitrile To 4-(2-amino-7-benzyl-7H-pyrrolo[2,3-d]pyrimidin-4-yloxy)-3,5-dimethyl-benzonitrile (70 mg, 0.19 mmol) in a polyethylene flask at −50° C. under argon was added 60% HF in pyridine (12 mL). To the solution was added tert-butylnitrite (0.068 mL, 0.57 mmol) dropwise for 5 min. The reaction was warmed to −40° C. and stirred for 30 min at the temperature. The reaction was then diluted with CHCl$_3$ (100 mL) and poured into K$_2$CO$_3$ (3 g) in a beaker. Ice water (50 mL) was carefully added. The CHCl$_3$ layer was separated, washed with aqueous NaHCO$_3$ solution (20 mL) and brine (20 mL), dried with Na$_2$SO$_4$, and concentrated to dryness. Silica gel chromatography (Hexanes:EtOAc=75:25) yielded 36 mg (51%) of 4-(7-benzyl-2-fluoro-7H-pyrrolo[2,3-d]pyrimidin-4-yloxy)-3,5-dimethyl-benzonitrile.

Step C

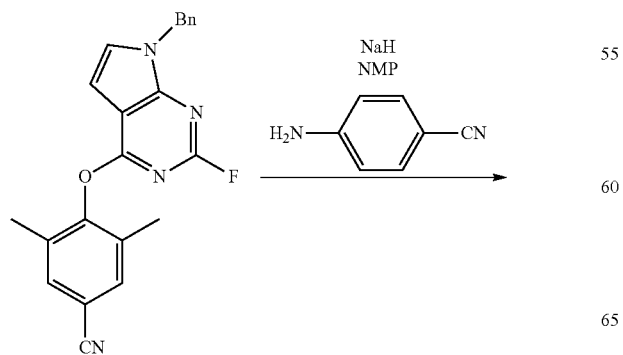

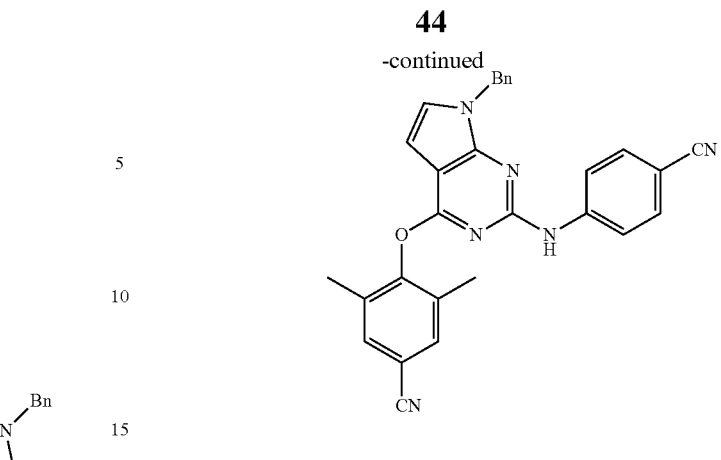

4-[7-benzyl-2-(4-cyano-phenylamino)-7H-pyrrolo[2,3-d]pyrimidin-4-yloxy]-3,5-dimethyl-benzonitrile To a solution of 4-aminobenzonitrile (54 mg, 0.46 mmol) in 1-methyl-2-pyrridone (1 mL) was added NaH (18 mg, 0.46 mmol). The reaction mixture was stirred at room temperature for 15 min and a solution of 4-(7-benzyl-2-fluoro-7H-pyrrolo[2,3-d]pyrimidin-4-yloxy)-3,5-dimethyl-benzonitrile (34 mg, 0.091 mmol) in 1-methyl-2-pyrridone (1 mL) was added to the mixture. The mixture was stirred at room temperature for 1 h, poured into ice water and extracted with EtOAc (2×20 mL). The combined organic solution was washed with H$_2$O (20 mL) and brine (20 mL), dried with Na$_2$SO$_4$, and concentrated to dryness. Silica gel chromatography (Hexanes:EtOAc=75:25) yielded 28 mg (65%) of 4-[7-benzyl-2-(4-cyano-phenylamino)-7H-pyrrolo[2,3-d]pyrimidin-4-yloxy]-3,5-dimethyl-benzonitrile.

Step D

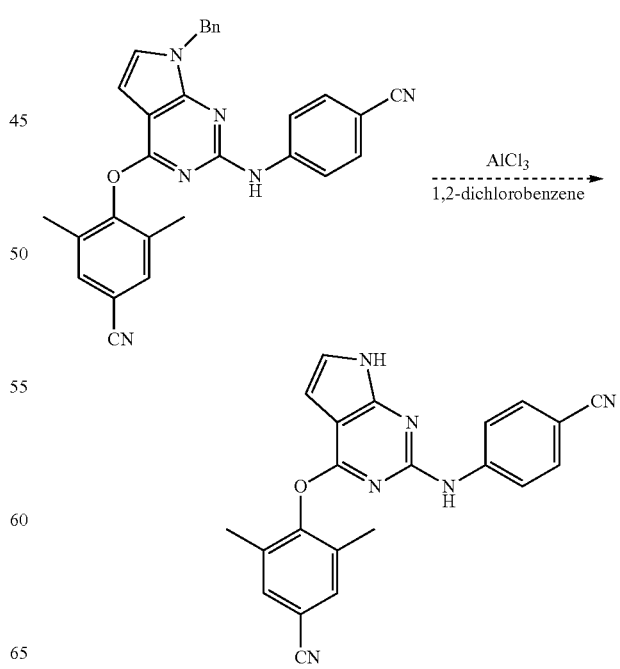

4-[2-(4-Cyano-phenylamino)-7H-pyrrolo[2,3-d]pyrimidin-4-yloxy]-3,5-dimethyl-benzonitrile To a solution of 4-[7-benzyl-2-(4-cyano-phenylamino)-7H-pyrrolo[2,3-d]pyrimidin-4-yloxy]-3,5-dimethyl-benzonitrile (28 mg, 0.060 mmol) in 1,2-dichlorobenzene (1 mL) was added aluminum chloride (40 mg, 0.30 mmol). The reaction mixture was stirred at 160° C. for 45 min and cooled to room temperature. The mixture was poured into ice water and extracted with $CH_2Cl_2$ (2×10 mL). The combined organic solution was washed with brine (10 mL), dried with $Na_2SO_4$, and concentrated to dryness. Silica gel chromatography (Hexanes:EtOAc=50:50) yielded 6 mg (27%) of 4-[2-(4-cyano-phenylamino)-7H-pyrrolo[2,3-d]pyrimidin-4-yloxy]-3,5-dimethyl-benzonitrile as a tan solid.

Example 6

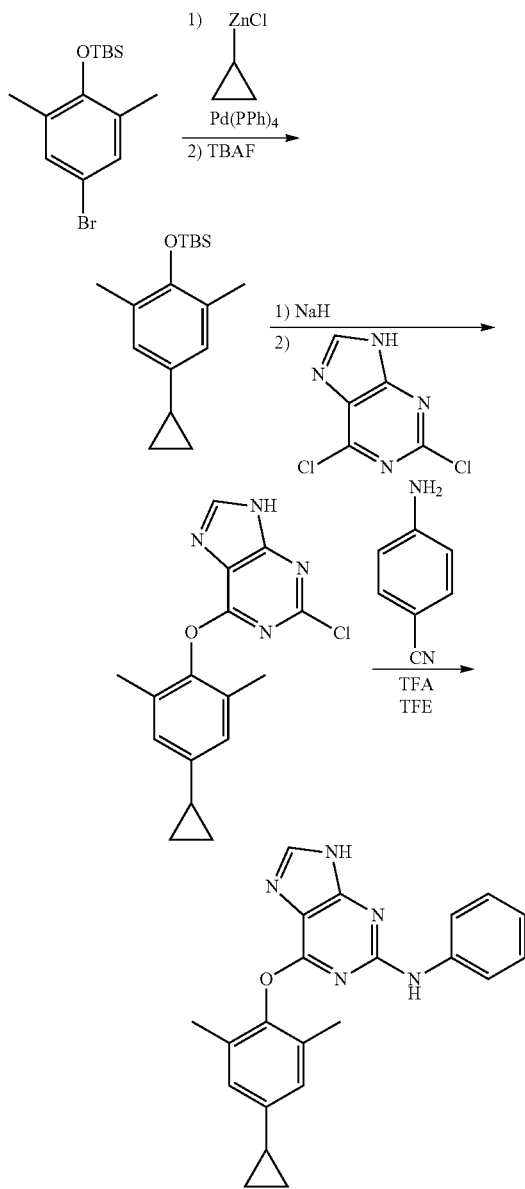

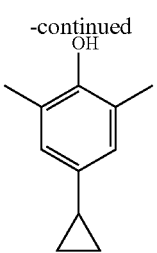

4-Cyclopropyl-2,6-dimethylphenol

To a suspension of (4-bromo-2,6-dimethylphenoxy) tert-butyldimethylsilane (668 mg, 2.12 mmol) and tetrakis(triphenylphosphine)palladium (122 mg, 0.11 mmol) in THF (20 mL) was added cyclopropyl zinc chloride (28.0 mL, 11.2 mmol). The mixture was heated at 80° C. for 24 h and cooled to room temperature. The reaction was passed through a short pad of $SiO_2$ to remove the catalyst and the solution was concentrated to oil. The resulting oil was diluted in EtOAc (100 mL), washed with brine (100 mL), dried with $Na_2SO_4$, and concentrated to dryness. Silica gel chromatography (Hexanes:EtOAc=90:10) yielded 370 mg (63%) of tert-butyl (4-cyclopropyl-2,6-dimethylphenoxy)dimethylsilane. To tert-butyl(4-cyclopropyl-2,6-dimethylphenoxy)dimethylsilane (320 mg, 1.16 mmol) in THF (10 mL) was added a solution of tetrabutylammonium fluoride (5.0 mL, 1 M in THF, 5.0 mmol) and acetic acid (0.40 mL). The reaction was stirred at room temperature for 3 h and concentrated to dryness. Silica gel chromatography (Hexanes:EtOAc=85:15) yielded 175 mg (93%) of 4-cyclopropyl-2,6-dimethylphenol as a light yellow oil.

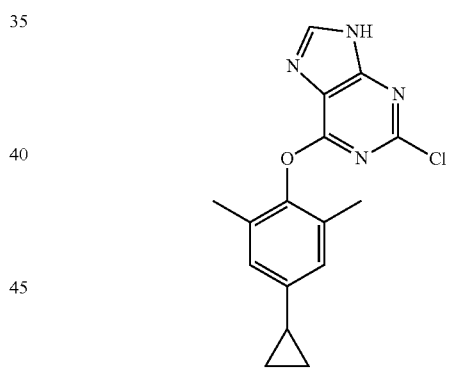

2-chloro-6-(4-cyclopropyl-2,6-dimethylphenoxy)-9H-purine

To a solution of 4-cyclopropyl-2,6-dimethylphenol (263 mg, 1.62 mmol) in 1-methyl-2-pyrridone (3 mL) at 0° C. was added NaH (65 mg, 1.62 mmol). The reaction mixture was stirred at room temperature for 30 min and a solution of 2,6-dichloropurine (102 mg, 0.54 mmol) in 1-methyl-2-pyrridone (2 mL) was added to the mixture. The mixture was heated at 100° C. for 16 h and then cooled to room temperature. The reaction was poured into ice water and extracted with $CHCl_3$ (3×20 mL). The combined organic solution was washed with $H_2O$ (20 mL) and brine (20 mL), dried with $Na_2SO_4$, and concentrated to dryness. Silica gel chromatography (MeOH:$CHCl_3$=5:95) yielded 114 mg (67%) of 2-chloro-6-(4-cyclopropyl-2,6-dimethylphenoxy)-9H-purine.

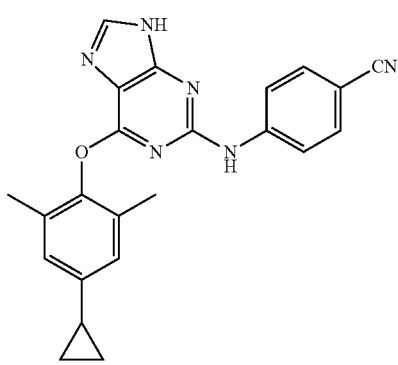 [SMILES: Cc1cc(C2CC2)cc(C)c1Oc1nc(Nc2ccc(C#N)cc2)nc2[nH]cnc12]

4-(6-(4-cyclopropyl-2,6-dimethylphenoxy)-9H-purin-2-ylamino)benzonitrile

To a suspension of 2-chloro-6-(4-cyclopropyl-2,6-dimethylphenoxy)-9-1'-purine (28 mg, 0.088 mmol) and 4-aminobenzonitrile (42 mg, 0.35 mmol) in 2,2,2-trifluoroethanol (3 mL) in a sealed tube was added trifluoroacetic acid (0.056 mL, 0.70 mmol). The resulting solution was heated at 90° C. for 3 days. The reaction was cooled to room temperature and concentrated to dryness. Silica gel chromatography (CH$_2$Cl$_2$:Acetone=80:20) yielded 7 mg (20%) of 4-(6-(4-cyclopropyl-2,6-dimethylphenoxy)-9H-purin-2-ylamino)benzonitrile as a light yellow solid.

Example 7

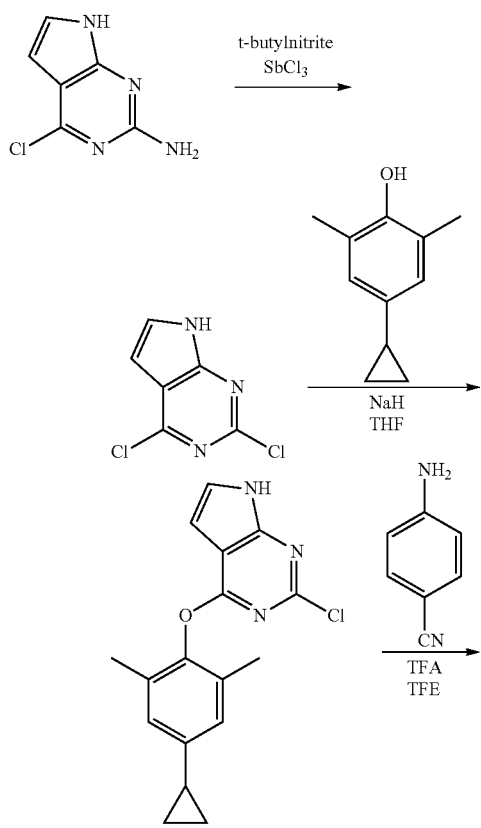

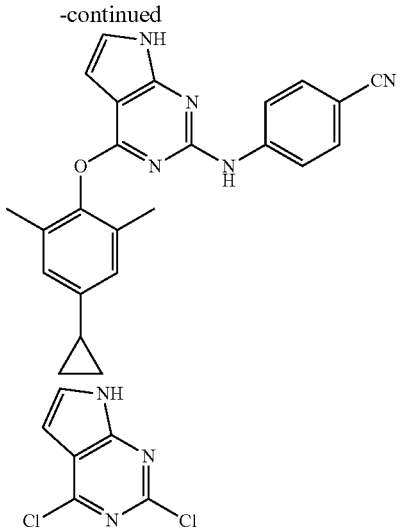

2,4-dichloro-7H-pyrrolo[2,3-d]pyrimidine

To a suspension of 4-chloro-7H-pyrrolo[2,3-d]pyrimidin-2-ylamine (500 mg, 2.97 mmol) in 1,2-dichloroethane (40 mL) at −10° C. under argon was added antimony chloride (750 mg, 3.29 mmol). After stirring for 5 min, tert-butylnitrite (2.50 mL, 20.8 mmol) was added to the solution. The reaction was stirred at −10° C. for 3 h. The reaction was diluted with CHCl$_3$ (100 mL) and poured into ice water (50 mL). The CHCl$_3$ layer was separated, washed with brine (20 mL), dried with Na$_2$SO$_4$, and concentrated to dryness. Silica gel chromatography (Hexanes:EtOAc=50:50) yielded 239 mg (43%) of 2,4-dichloro-7H-pyrrolo[2,3-d]pyrimidine as a tan solid.

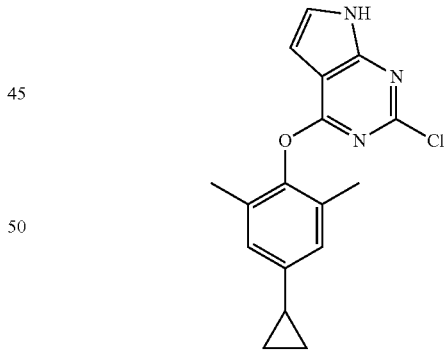

2-chloro-4-(4-cyclopropyl-2,6-dimethylphenoxy)-7H-pyrrolo[2,3-d]pyrimidine

To a solution of 4-cyclopropyl-2,6-dimethylphenol (259 mg, 1.60 mmol) in THF (3 mL) at 0° C. was added NaH (64 mg, 1.60 mmol). The reaction mixture was stirred at room temperature for 30 min and a solution of 2,4-dichloro-7H-pyrrolo[2,3-d]pyrimidine (100 mg, 0.53 mmol) in THF (2 mL) was added to the mixture. The mixture was heated at 80°

C. for 16 h and cooled to room temperature. The reaction was poured into ice water and extracted with CHCl₃ (3×20 mL). The combined organic solution was washed with H₂O (20 mL) and brine (20 mL), dried with Na₂SO₄, and concentrated to dryness. Silica gel chromatography (Hexanes:EtOAc=75:25) yielded 79 mg (48%) of 2-chloro-4-(4-cyclopropyl-2,6-dimethylphenoxy)-7H-pyrrolo[2,3-d]pyrimidine as a tan solid.

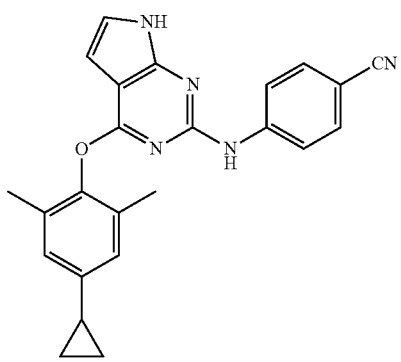

4-(4-(4-cyclopropyl-2,6-dimethylphenoxy)-7H-pyrrolo[2,3-d]pyrimidin-2-ylamino)benzonitrile To a suspension of 2-chloro-4-(4-cyclopropyl-2,6-dimethylphenoxy)-7H-pyrrolo[2,3-d]pyrimidine (75 mg, 0.24 mmol) and 4-aminobenzonitrile (113 mg, 0.96 mmol) in 2,2,2-trifluoroethanol (4 mL) in a sealed tube was added trifluoroacetic acid (0.15 mL, 1.92 mmol). The resulting solution was heated at 90° C. for 3 days. The reaction was diluted with EtOAc (50 mL), washed with NaHCO₃ (20 mL) and brine (20 mL), dried with Na₂SO₄, and concentrated to dryness. Silica gel chromatography (CH₂Cl₂:Acetone=90:10) yielded 15 mg (16%) of 4-(4-(4-cyclopropyl-2,6-dimethylphenoxy)-7H-pyrrolo[2,3-d]pyrimidin-2-ylamino)benzonitrile as a tan solid.

Example 8

Scheme 1

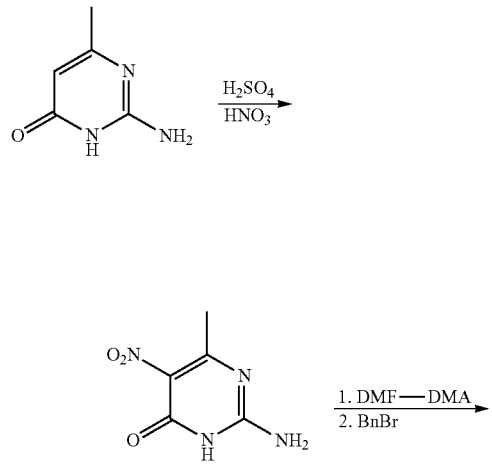

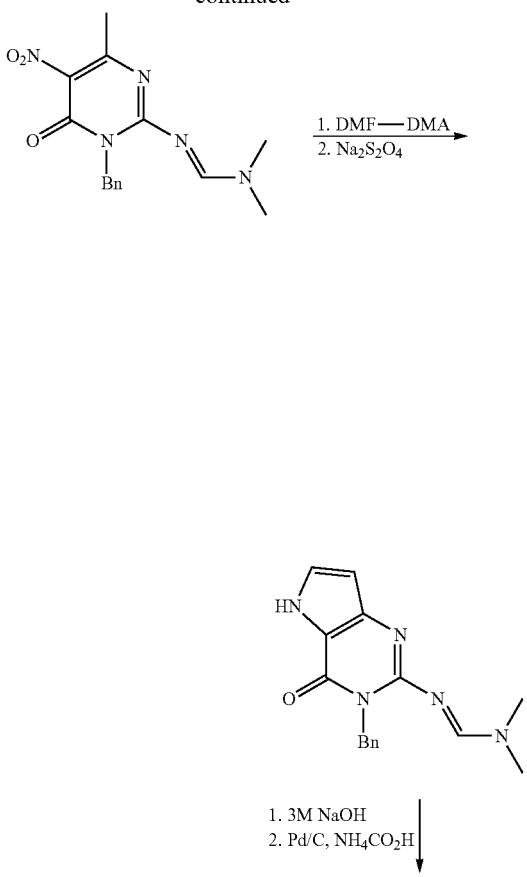

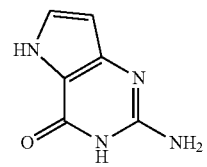

Scheme 1 illustrate the synthesis of 9-deazaguanine by starting with commercially available 2-amino-6-methylpyrimidin-4(3H)-one and nitrated with nitric acid followed by treatment of the nitrated product with N,N-dimethylformamide dimethyl acetal (DMF-DMA) to afford the corresponding 2-(dimethylamino)methyleneimino derivative. It was then benzylated to produce 3-benzyl-2-[(dimethylamino)methyleneimino]-5-nitro-6-methylpyrimidin-4-one by treating with benzyl bromide and converted to benzylated-2,6-bis-dimethylaminomethylene derivative with DMF-DMA. Reductive cyclization with sodium hydrosulfite followed by de-protection with 3M NaOH and de-benzylation with Pd/C and NH₄CO₂H afforded 9-deazaguanine.

51 52
Scheme 2
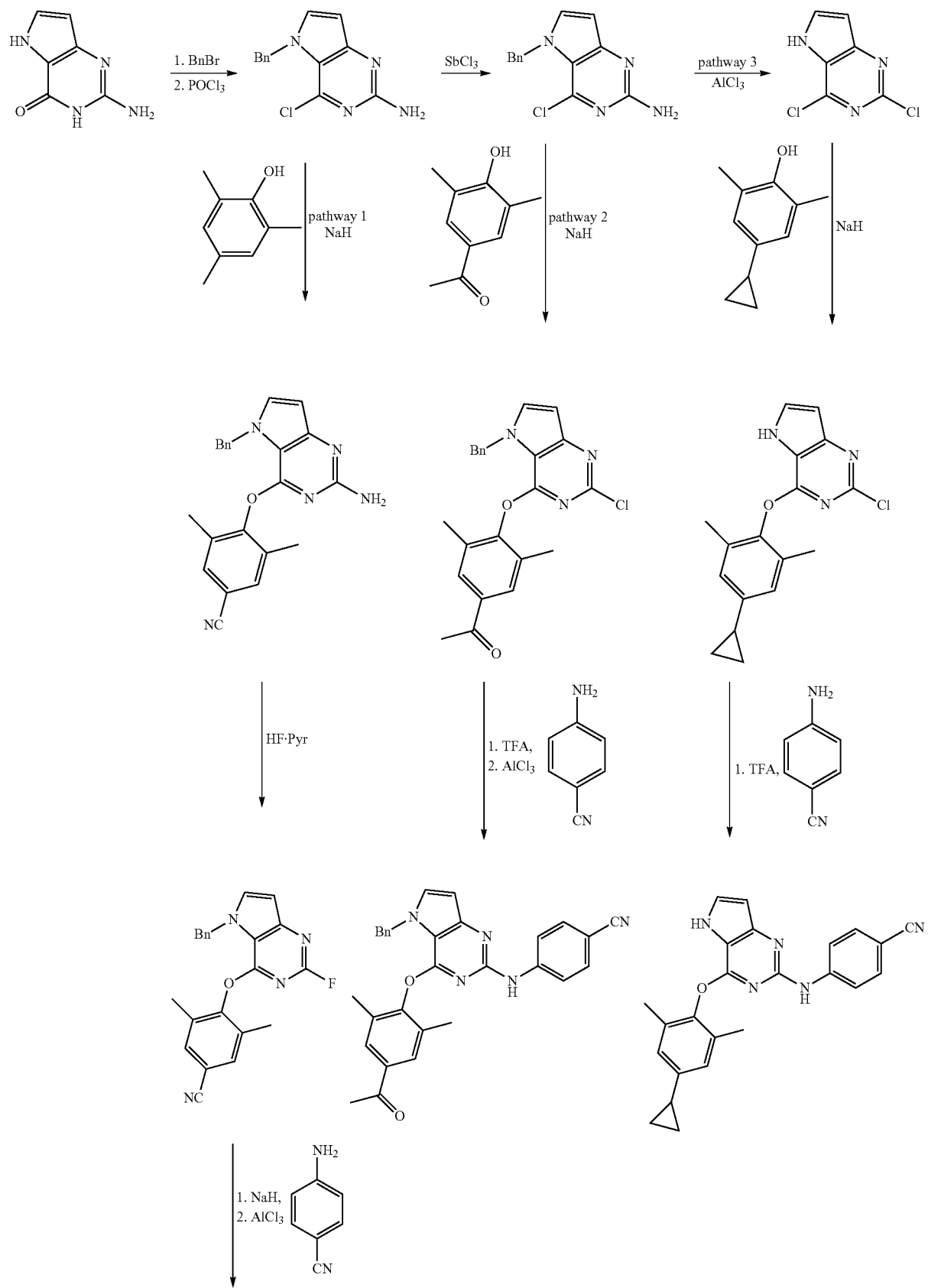

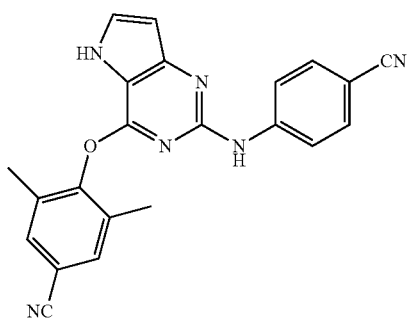 [SMILES: Cc1cc(C#N)cc(C)c1Oc1nc(Nc2ccc(C#N)cc2)nc2cc[nH]c12]

Scheme 2 illustrates the 3 different pathways which provide the various substituted 9-deazapurines. Other products are synthesized by analogous methods, which a person skilled in the art could formulate, based on the reaction sequences given above. In certain cases, the person skilled in the art would see that protecting groups might be necessary. The synthetic scheme can be summarized as follows.

Benzylation of 9-deazaguanine followed by chlorination with POCl₃ gives the chlorinated 9-deazapurine product. This chlorinated intermediate can either be coupled with R2 (pathway 1) followed by diazotization with t-butyl nitrite; displaced with F; coupled with R3 and de-benzylated to give the product; or it can undergo pathway 2, which is diazotization with t-butyl nitrite in the presence of antimony chloride followed by coupling with R2 and R3, followed by de-benzylation to afford the final product. Alternatively, pathway 3 provides for de-benzylation of the dichloro-9-deazapurine followed by the coupling with R2 and R3 respectively to provide the various substituted 9-deazapurine.

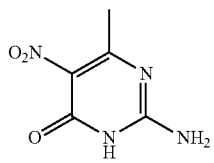

2-Amino-6-methyl-5-nitropyrimidin-4(3H)-one

To a mixture of 2-amino-6-methylpyrimidin-4(3H)-one (50 g, 0.4 mol) in 250 mL of H₂SO₄ at 0° C. was added 40 mL of HNO₃ with an additional funnel. After being stirred at room temperature for 3 h, the reaction mixture was slowly poured into 3.6 L of diethyl ether and stirred for 15 min. Decant the ether solution and added 1.0 L of ethyl acetate to the solid and stirred for 10 h. The solid (54.8 g, 81% yield) was filtered and used for next step without any further purification.

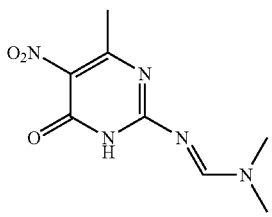 [SMILES: Cc1nc(/N=C/N(C)C)[nH]c(=O)c1[N+](=O)[O-]]

(E)-N,N-Dimethyl-N'-(4-methyl-5-nitro-6-oxo-1,6-dihydropyrimidin-2-yl)formimidamide To a suspension of 2-Amino-6-methyl-5-nitropyrimidin-4 (3H)-one (54.8 g, 0.32 mol) in CH₂Cl₂ (461 mL) was added DMF-dimethylacetal (103.1 mL, 0.77 mol) and stirred at room temperature for 1.5 h. The reaction mixture was filtered, washed with CH₂Cl₂, and used for the next step without further purification (31.9 g, 44% yield).

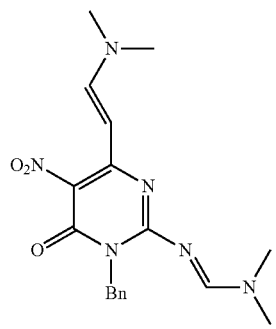 [SMILES: CN(C)/C=C/c1nc(/N=C/N(C)C)n(Cc2ccccc2)c(=O)c1[N+](=O)[O-]]

(E)-N'(1-benzyl-4-methyl-5-nitro-6-oxo-1,6-dihydropyrimidin-2-yl)-N,N-dimethylformimidamide To a suspension of (E)-N,N-Dimethyl-N'-(4-methyl-5-nitro-6-oxo-1,6-dihydropyrimidin-2-yl)formimidamide (53.4 g, 0.24 mmol) in DMF (690 mL) was added DBU (44.6 mL, 0.30 mol) and benzyl bromide (44.4 mL, 0.29 mol) and stirred at room temperature for 1 h. The excess of DBU was neutralized with HCl, and the mixture was concentrated in vacuo. The residue was dissolved in methylene chloride and extracted twice with 2M HCl and water, then dried over Na₂SO₄ and concentrated. Trituration with ethanol afforded the crystalline product which was washed with ethanol to give the product (64.7 g, 86% yield) and used in the next step without further purification.

(E)-N'-(1-benzyl-4-((E)-2-(dimethylamino)vinyl)-5-nitro-6-oxo-1,6-dihydropyrimidin-2-yl)-N,N-dimethylformimidamide To a solution of (E)-N'(1-benzyl-4-methyl-5-nitro-6-oxo-1,6-dihydropyrimidin-2-yl)-N,N-dimethylformimidamide (64.7 g, 0.2 mol) in DMF (254 mL) was added DMF-dimethylacetal (54.5 mL, 0.41 mol). The reaction mixture was stirred for 3 h at 65° C., cooled, and the solvent was removed under reduced pressure. The residue was triturated with ethanol, and the solid was collected by vacuum filtration (69.2 g, 91%) and used in the next step without further purification.

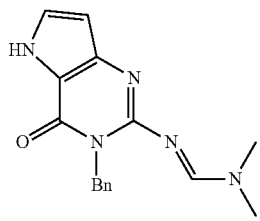 [SMILES: CN(C)/C=N/c1nc2cc[nH]c2c(=O)n1Cc1ccccc1]

(E)-N'-(3-benzyl-4-oxo-4,5-dihydro-3H-pyrrolo[3,2-d]pyrimidin-2-yl)-N,N-dimethylformimidamide To a mixture of (E)-N'-(1-benzyl-4-((E)-2-(dimethylamino)vinyl)-5-nitro-6-oxo-1,6-dihydropyrimidin-2-yl)-N,N-dimethylformimidamide (43.0 g, 0.12 mol) in THF (151 mL) was added an aqueous saturated solution of $Na_2S_2O_4$ and stirred at room temperature overnight. Upon completion of the reaction, the solid was filtered and washed with THF to afford the product (21.2 g, 62% yield) which was used in the next step without further purification.

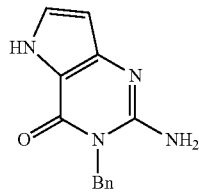 [SMILES: Nc1nc2cc[nH]c2c(=O)n1Cc1ccccc1]

2-Amino-3-benzyl-3H-pyrrolo[3,2-d]pyrimidin-4(5H)-one

To a mixture of (E)-N'-(3-benzyl-4-oxo-4,5-dihydro-3H-pyrrolo[3,2-d]pyrimidin-2-yl)-N,N-dimethylformimidamide (21.2 g, 0.07 mol) in MeOH (382 mL) was added 3M NaOH (276 mL) and heated at 100° C. for 5 h. After completion of the reaction, the reaction mixture was cooled to 0° C. The solid was filtered (15.8 g, 91%) and used in the next step without further purification.

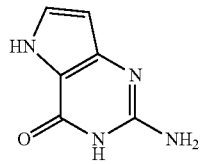

2-Amino-3H-pyrrolo[3,2-d]pyrimidin-4(5H)-one

To a mixture of 2-amino-3-benzyl-3H-pyrrolo[3,2-d]pyrimidin-4(5H)-one (10 g, 0.04 mol) in MeOH (334 mL) was added 10% Pd/C (2 g), ammonium formate (13.2 g, 0.21 mmol) and heated at 75° C. for 4 h. After completion of the reaction, the reaction mixture was cooled and filtered through a pad of Celite with hot 1:1 DMF/MeOH. The filtrate was concentrated in vacuo to provide the product as an off-white solid (6.2 g, 99%).

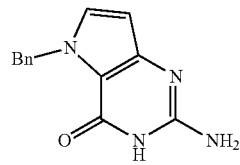 [SMILES: Nc1nc2ccn(Cc3ccccc3)c2c(=O)[nH]1]

2-Amino-5-benzyl-3H-pyrrolo[3,2-d]pyrimidin-4(5H)-one

To a suspension of 2-amino-3H-pyrrolo[3,2-d]pyrimidin-4(5H)-one (336.7 mg, 2.0 mmol) in $CH_2Cl_2$ (14.3 mL) was added benzyl bromide (0.26 mL, 2.2 mmol) and TBABr (644 mg, 2.0 mmol). The reaction mixture was cooled to 0° C., and to it was added 50% NaOH (1.7 mL). The resulting mixture was stirred for 2 h as it warmed from 0° C. to room temperature. Water was then added, and the solution was washed with $CHCl_3$. The combined organic layers were washed with brine, dried over $Na_2SO_4$, filtered, and concentrated in vacuo. Purification by column chromatography, eluting with $CH_2Cl_2$/Acetone (5:1-1:1), afforded the product as a tan solid (423 mg, 82%)

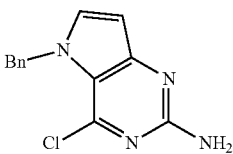 [SMILES: Nc1nc(Cl)c2c(ccn2Cc2ccccc2)n1]

5-benzyl-4-chloro-5H-pyrrolo[3,2-d]pyrimidin-2-amine

A mixture of 2-amino-5-benzyl-3H-pyrrolo[3,2-d]pyrimidin-4(5H)-one (1.1 g, 7.4 mmol) and $POCl_3$ (7 mL, 74 mmol) was heated at 116° C. for 3 h. Upon completion of the reaction, the reaction mixture was poured into ice and extracted three times with ethyl acetate. The combined organic layers were washed with brine, dried over $Na_2SO_4$, filtered, and concentrated in vacuo. Purification by column chromatography, eluting with $CH_2Cl_2$/Acetone (3:1), afforded the product as a white solid (490 mg, 40%).

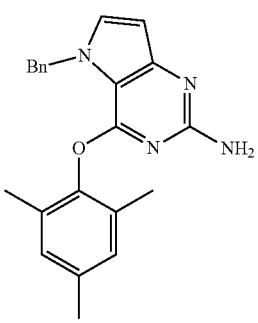 [SMILES: Cc1cc(C)c(Oc2nc(N)nc3ccn(Cc4ccccc4)c23)c(C)c1]

5-benzyl-4-(mesityloxy)-5H-pyrrolo[3,2-d]pyrimidin-2-amine

To a stirred suspension of NaH (56 mg, 2.33 mmol) in dry NMP (2 mL) was added 2,4,6-trimethyl phenol (317 mg, 2.33 mmol). The mixture was stirred at room temperature for 30 min under argon. The reaction mixture was added to a solution of 5-benzyl-4-chloro-5H-pyrrolo[3,2-d]pyrimidin-2-amine (200 mg, 0.78 mmol) in dry NMP (1.5 mL) and the resulting solution was heated at 90° C. for 16 h. After completion of the reaction, the reaction mixture was diluted with water and washed with EtOAc. The combined organic layers were washed with water, 2% NaOH, and brine and dried over $Na_2SO_4$, filtered, and concentrated in vacuo. The crude product was purified by column chromatography, eluting with hexanes/ethyl acetate (3:1) to give the product as a white solid (140 mg, 50%).

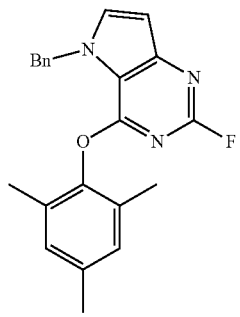 [SMILES: Cc1cc(C)c(Oc2nc(F)nc3ccn(Cc4ccccc4)c23)c(C)c1]

5-benzyl-2-fluoro-4-(mesityloxy)-5H-pyrrolo[3,2-d]pyrimidine

A solution of 5-benzyl-4-(mesityloxy)-5H-pyrrolo[3,2-d]pyrimidin-2-amine (139.9 mg, 0.39 mmol) in pyridine (1.6 mL) was cooled to −50° C. and HF-pyr (8 mL) and t-butyl nitrite (0.19 mL, 1.56 mmol) was added dropwise. The reaction mixture was stirred at 50° C. to −30° C. for 1.5 h. Upon completion of the reaction, the reaction mixture was poured into $K_2CO_3$ (5 g), slowly added water and washed with $CHCl_3$×3. The combined organic layers were washed with brine, dried ($Na_2SO_4$), filtered and concentrated in vacuo. The crude product was purified by silica gel column chromatography, eluting with hexanes/ethyl acetate (2:1) to give the product as a white solid (116 mg, 82%).

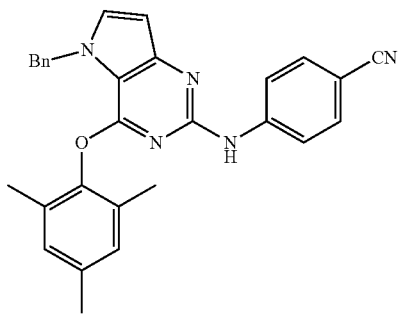

4-(5-benzyl-4-(mesityloxy)-5H-pyrrolo[3,2-d]pyrimidin-2-ylamino)benzonitrile A stirred suspension of NaH (63.8 mg, 2.66 mmol) in dry NMP (1.5 mL) was added 4-aminobenzylnitrile (188 mg, 2.66 mmol) and stirred at room temperature for 30 min under argon. The reaction mixture was added to a solution of 5-benzyl-2-fluoro-4-(mesityloxy)-5H-pyrrolo[3,2-d]pyrimidine (115 mg, 0.32 mmol) in dry NMP (1.7 mL) and stirred at room temperature for 2 h. After completion of the reaction, the resulting mixture was diluted with water and washed with EtOAc 3 times. The combined organic layers were washed with water, $NH_4Cl$, water×2, and brine, dried over $Na_2SO_4$, filtered, and concentrated in vacuo. The crude product was purified by column chromatography, eluting with 1% MeOH: $CH_2Cl_2$, which afforded the product as a tan solid (120 mg, 80%).

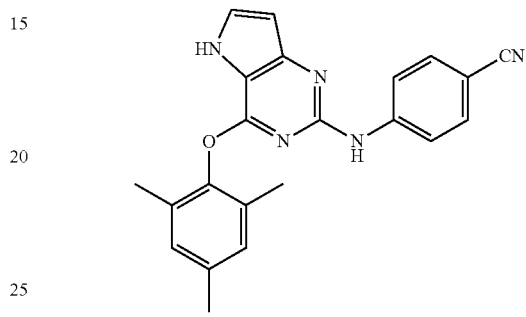

4-(4-(Mesityloxy)-5H-pyrrolo[3,2-d]pyrimidin-2-ylamino)benzonitrile

To a suspension of 4-(5-benzyl-4-(mesityloxy)-5H-pyrrolo[3,2-d]pyrimidin-2-ylamino)benzonitrile (150 mg, 0.33 mmol) in 1,2-dichlorobenzene (13 mL) was added $AlCl_3$ (436 mg, 3.27 mmol). The reaction mixture was heated at 160° C. for 1.5 h during which the reaction mixture became dark and homogeneous. Upon completion of the reaction, the reaction mixture was cooled and washed with $NH_4Cl$. The combined organic layers were washed with brine, dried over $Na_2SO_4$, filtered, and concentrated in vacuo. The crude product was purified by column chromatography, eluting with Hexanes: Ethyl acetate (5:1-1:1) provided the product as a tan solid (27.8 mg, 23%).

Example 9

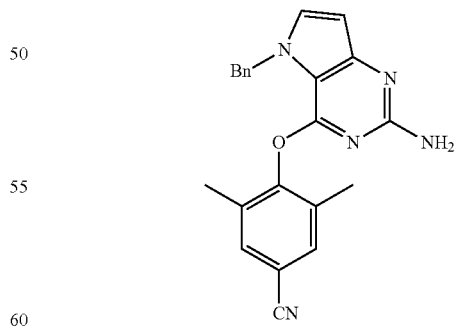

4-(2-Amino-5-benzyl-5H-pyrrolo[3,2-d]pyrimidin-4-yloxy)-3,5-dimethylbenzonitrile To a stirred suspension of NaH (155 mg, 6.47 mmol) in dry NMP (4 mL) was added 4-hydroxy-3,5-dimethylbenzonitrile (570 mg, 3.88 mmol), and the mixture was stirred at room temperature for 30 min under argon. The reaction mixture was added to a solution of 5-benzyl-4-chloro-5H-pyrrolo[3,2-d]pyrimidin-2-amine (400 mg, 1.55 mmol) in dry NMP (4 mL) and heated at 160° C. for 16 h. After completion of the reaction, the resulting mixture was diluted with water and washed with EtOAc. The combined organic layers were washed with water, 2% NaOH, brine, dried over Na₂SO₄, filtered, and concentrated in vacuo. The crude product was purified by column chromatography, eluting with hexanes/ethyl acetate (2:1-1:4) to give the product as a light yellow solid (342 mg, 60%).

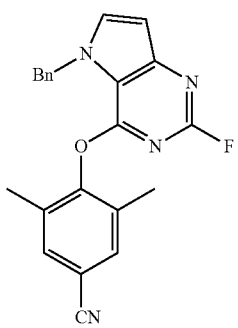 [SMILES: Cc1cc(C#N)cc(C)c1Oc1nc(F)nc2ccn(Cc3ccccc3)c12]

4-(5-benzyl-2-fluoro-5H-pyrrolo[3,2-d]pyrimidin-4-yloxy)-3,5-dimethylbenzonitrile A solution of 4-(2-amino-5-benzyl-5H-pyrrolo[3,2-d]pyrimidin-4-yloxy)-3,5-dimethylbenzonitrile (319.4 mg, 0.87 mmol) in pyridine (3 mL) was cooled to −50° C. and HF-pyr (15 mL) and t-butyl nitrite (0.42 mL, 3.46 mmol) were added dropwise. The reaction mixture was stirred at −50° C. to −20° C. for 1.5 h. Upon completion of the reaction, the mixture was poured into K₂CO₃ (8 g), diluted with water and washed with CHCl₃×3. The combined organic layers were washed with brine, dried (Na₂SO₄), filtered, and concentrated in vacuo. The crude product was purified by silica gel column chromatography, eluting with hexanes/ethyl acetate (2:1-1:1) which same the product as a light yellow solid (314 mg, 97%).

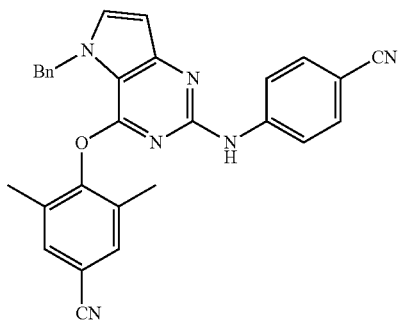 [SMILES: Cc1cc(C#N)cc(C)c1Oc1nc(Nc2ccc(C#N)cc2)nc2ccn(Cc3ccccc3)c12]

4-(5-benzyl-2-(4-cyanophenylamino)-5H-pyrrolo[3,2-d]pyrimidin-4-yloxy)-3,5-dimethylbenzonitrile To a stirred suspension of NaH (101 mg, 4.21 mmol) in dry NMP (4 mL) was added 4-aminobenzylnitrile (299 mg, 2.53 mmol) and stirred at room temperature for 30 min under argon. The reaction mixture was added to a solution of 4-(5-benzyl-2-fluoro-5H-pyrrolo[3,2-d]pyrimidin-4-yloxy)-3,5-dimethylbenzonitrile (314 mg, 0.84 mmol) in dry NMP (4.4 mL) and stirred at room temperature for 2 h. After completion of the reaction, the resulting mixture was diluted with water and washed with EtOAc×3. The combined organic layers were washed with water, NH₄Cl, water×2, brine, dried over Na₂SO₄, filtered, and concentrated in vacuo. The crude product was purified by column chromatography, eluting with 1% MeOH:CH₂Cl₂, producing the product as a tan solid (320 mg, 80%).

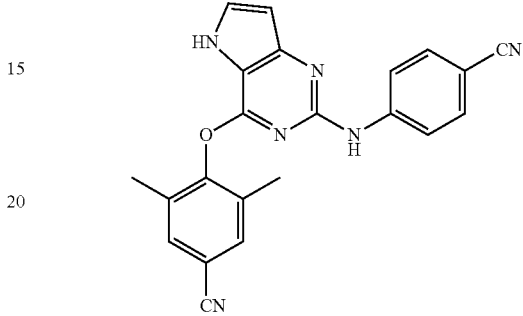

4-(2-(4-Cyanophenylamino)-5H-pyrrolo[3,2-d]pyrimidin-4-yloxy)-3,5-dimethylbenzonitrile To a suspension of 4-(5-benzyl-2-(4-cyanophenylamino)-5H-pyrrolo[3,2-d]pyrimidin-4-yloxy)-3,5-dimethylbenzonitrile (240 mg, 0.51 mmol) in 1,2-dichlorobenzene (20 mL) was added AlCl₃ (681 mg, 5.1 mmol). The reaction mixture was heated at 160° C. for 1.5 h, during which time the reaction mixture became dark and homogeneous. Upon completion of the reaction, the reaction mixture was cooled and washed with NH₄Cl. The combined organic layers were washed with brine, dried over Na₂SO₄, filtered and concentrated in vacuo. The crude product was purified by preparative TLC TLC eluting with Hexanes:Ethyl acetate (2.5:1) and produced the product as a pink solid (51 mg, 26%).

Example 10

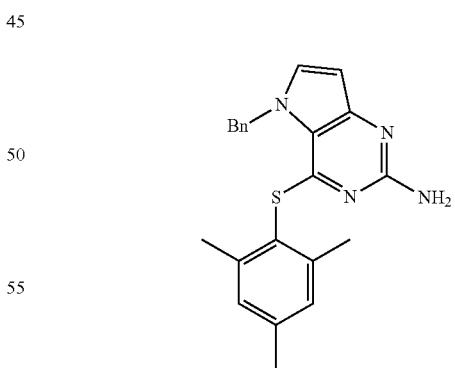

5-benzyl-4-(mesitylthio)-5H-pyrrolo[3,2-d]pyrimidin-2-amine

To a stirred suspension of NaH (48 mg, 2 mmol) in dry NMP (2 mL) was added 2,4,6-trimethyl-benzene-1-thiol (191 mg, 1.2 mmol) The mixture was and stirred at room temperature for 30 min under argon. The reaction mixture was then added to a solution of 5-benzyl-4-chloro-5H-pyrrolo[3,2-d]pyrimidin-2-amine (103 mg, 0.4 mmol) in dry NMP (2.5 mL) and heated at 60° C. for 16 h. After completion of the reaction, the resulting mixture was diluted with water and washed with EtOAc. The combined organic layers were washed with water, 2% NaOH, and brine; dried over $Na_2SO_4$; filtered; and concentrated in vacuo. The crude product was purified by column chromatography, eluting with hexanes/ethyl acetate (2:1-1:3) to give the product as a light yellow solid (131 mg, 88%).

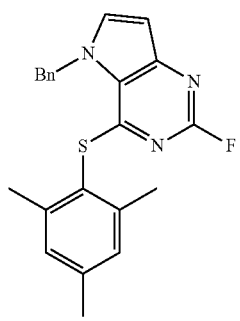 [SMILES: Cc1cc(C)c(Sc2nc(F)nc3ccn(Cc4ccccc4)c23)c(C)c1]

5-benzyl-2-fluoro-4-(mesitylthio)-5H-pyrrolo[3,2-d]pyrimidine

A solution of 5-benzyl-4-(mesitylthio)-5H-pyrrolo[3,2-d]pyrimidin-2-amine (131 mg, 0.35 mmol) in pyridine (1.6 mL) was cooled to −50° C. and added HF-pyr (8 mL) and t-butyl nitrite (0.17 mL, 1.4 mmol) dropwise. The reaction mixture was stirred at −50° C. to −40° C. for 1.5 h. Upon completion of the reaction, the reaction was poured into $K_2CO_3$ (5 g), slowly added water and washed with $CHCl_3$×3. The combined organic layers were washed with brine, dried ($Na_2SO_4$), filtered and concentrated in vacuo. The crude product was purified by silica gel column chromatography, eluting with hexanes/ethyl acetate (5:1-1:1) to give the product as an off-white solid (94 mg, 71%).

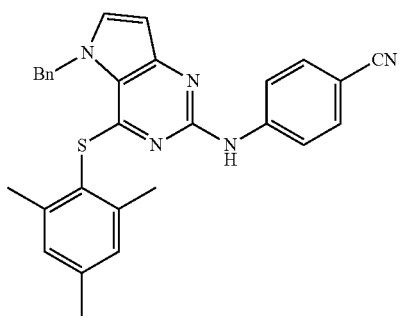 [SMILES: Cc1cc(C)c(Sc2nc(Nc3ccc(C#N)cc3)nc3ccn(Cc4ccccc4)c23)c(C)c1]

4-(5-benzyl-4-(mesitylthio)-5H-pyrrolo[3,2-d]pyrimidin-2-ylamino)benzonitrile

To a stirred suspension of NaH (30 mg, 1.25 mmol) in dry NMP (1.5 mL) was added 4-aminobenzylnitrile (87.4 mg, 0.74 mmol) and stirred at room temperature for 30 min under argon. The reaction mixture was added to a solution of 5-benzyl-2-fluoro-4-(mesitylthio)-5H-pyrrolo[3,2-d]pyrimidine (93 mg, 0.25 mmol) in dry NMP (1 mL) and stirred at room temperature for 2 h. After completion of the reaction, the resulting mixture was diluted with water and washed with EtOAc×3. The combined organic layers were washed with water, $NH_4Cl$, water×2, brine, dried over $Na_2SO_4$, filtered, and concentrated in vacuo. The crude product was purified by preparative TLC TLC, eluting with Hexanes:Ethyl acetate (1.5:1) afforded the product as a tan solid (12.6 mg, 11%).

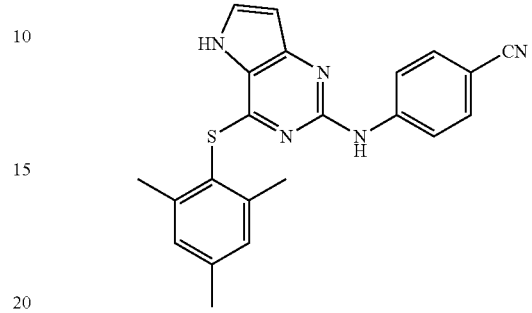

4-(4-(mesitylthio)-5H-pyrrolo[3,2-d]pyrimidin-2-ylamino)benzonitrile

To a suspension of 4-(5-benzyl-4-(mesitylthio)-5H-pyrrolo[3,2-a]pyrimidin-2-ylamino)benzonitrile (9.2 mg, 0.03 mmol) in 1,2-dichlorobenzene (1 mL) was added $AlCl_3$ (26 mg, 0.3 mmol). The reaction mixture was heated at 160° C. for 1.5 h, which the reaction mixture became dark and homogeneous. Upon completion of the reaction, the reaction mixture was cooled and washed with $NH_4Cl$. The combined organic layers were washed with brine, dried over $Na_2SO_4$, filtered, and concentrated in vacuo. The crude product was purified by preparative TLC TLC, eluting with Hexanes:Ethyl acetate (2.5:1) produced the product as a pink solid (7.7 mg, 20%).

Example 11

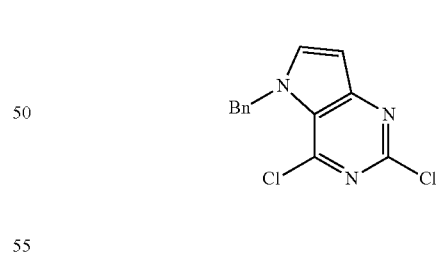

5-benzyl-2,4-dichloro-5H-pyrrolo[3,2-d]pyrimidine

To a suspension of 5-benzyl-4-chloro-5H-pyrrolo[3,2-d]pyrimidin-2-amine (641 mg, 2.5 mmol) in 1,2-dichloroethane (35 mL) was cooled to −10° C. $SbCl_3$ (850 mg, 3.7 mmol) was added. The reaction mixture was stirred for 5 min. t-butyl nitrite (2.1 mL, 17.4 mmol) was added dropwise and the stirred mixture was from −10° C. to room temperature for 5 h. Upon completion of the reaction, the reaction mixture was poured into ice water and washed with $CH_2Cl_2$. The combined organic layers were washed with brine, dried over Na$_2$SO$_4$, filtered and concentrated in vacuo. The crude product was purified by silica gel column chromatography eluting with Hexanes:Ethyl acetate (9:1-1:1), and gave the product as an off-white solid (528 mg, 77%).

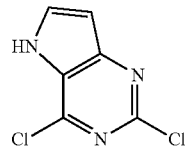

2,4-Dichloro-5H-pyrrolo[3,2-d]pyrimidine

To a suspension of 5-benzyl-2,4-dichloro-5H-pyrrolo[3,2-d]pyrimidine (177 mg, 0.64 mmol) in 1,2-dichlorobenzene (20 mL) was added AlCl$_3$ (852 mg, 6.4 mmol). The reaction mixture was heated at 160° C. for 1.5 h, during which the reaction mixture became dark and homogeneous. Upon completion of the reaction, the reaction mixture was cooled, added CHCl$_3$ and washed with NH$_4$Cl. The combined organic layers were washed with brine, dried over Na$_2$SO$_4$, filtered, and concentrated in vacuo. Added Hexanes and filtered off the product as purple solids (100 mg, 80%) and used for the next step without further purification.

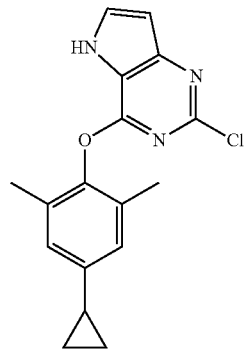 [SMILES: Cc1cc(C2CC2)cc(C)c1Oc1nc(Cl)nc2cc[nH]c12]

2-Chloro-4-(4-cyclopropyl-2,6-dimethylphenoxy)-5H-pyrrolo[3,2-d]pyrimidine

To a stirred suspension of NaH (25 mg, 0.64 mmol) in dry NMP (1.5 mL) was added 4-cyclopropyl-2,6-dimethylphenol (103 mg, 0.64 mmol) and the resolution mixture was stirred at room temperature for 30 min under argon. The reaction mixture was added to a solution of 2,4-dichloro-5H-pyrrolo[3,2-d]pyrimidine (120 mg, 0.64 mmol) in dry NMP (1.7 mL) and heated at 90° C. for 16 h. After completion of the reaction, the resulting mixture was diluted with water and washed with EtOAc. The combined organic layers were washed with water, brine, dried over Na$_2$SO$_4$, filtered, and concentrated in vacuo. The crude product was purified by column chromatography, eluting with hexanes/ethyl acetate (4:1-2:1), to give the product as a light yellow solid (20.2 mg, 8%).

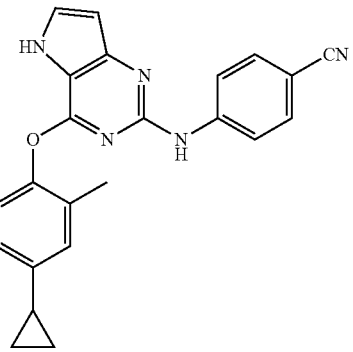

4-(4-(4-Cyclopropyl-2,6-dimethylphenoxy)-5H-pyrrolo[3,2-d]pyrimidin-2-ylamino)benzonitrile In a sealed tube was placed 2-chloro-4-(4-cyclopropyl-2,6-dimethylphenoxy)-5H-pyrrolo[3,2-d]pyrimidine (20 mg, 0.064 mmol), 4-aminobenzonitrile (31 mg, 0.26 mmol), TFE (0.21 mL) and TFA (0.04 mL, 0.51 mmol). The reaction mixture was stirred at 90° C. for 16 h. Upon completion of the reaction, the resulting mixture was diluted with water and washed with EtOAc. The combined organic layers were washed with NaHCO$_3$, brine, dried over Na$_2$SO$_4$, filtered, and concentrated in vacuo. The crude product was purified by preparative TLC TLC, eluting with 5% Acetone/CH$_2$Cl$_2$ to give the product as a light yellow solid (10.5 mg, 45%).

Example 12

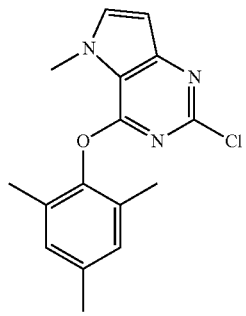 [SMILES: Cc1cc(C)c(Oc2nc(Cl)nc3ccn(C)c23)c(C)c1]

2-Chloro-4-(mesityloxy)-5-methyl-5H-pyrrolo[3,2-d]pyrimidine

To a stirred suspension of NaH (8.9 mg, 0.22 mmol) in dry NMP (1.0 mL) was added 2,4,6-trimethyl phenol (30.2 mg, 0.22 mmol) and stirred at room temperature for 30 min under argon. The reaction mixture was added to a solution of 2,4-dichloro-5-methyl-5H-pyrrolo[3,2-d]pyrimidine (44.6 mg, 0.22 mmol) in dry NMP (1.0 mL) and heated at 90° C. for 16 h. After completion of the reaction, the resulting mixture was cooled, diluted with water and washed with EtOAc. The combined organic layers were washed with water, brine, dried over Na$_2$SO$_4$, filtered, and concentrated in vacuo. The crude product was purified by column chromatography, eluting with hexanes/ethyl acetate (5:1-2:1), to give the product as a light yellow solid (52.7 mg, 80%).

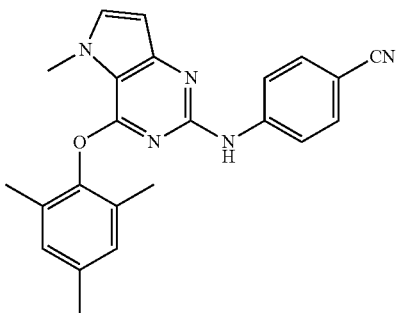 [SMILES: Cc1cc(C)c(Oc2nc(Nc3ccc(C#N)cc3)nc3ccn(C)c23)c(C)c1]

4-(4-(Mesityloxy)-5-methyl-5H-pyrrolo[3,2-d]pyrimidin-2-ylamino)benzonitrile

In a sealed tube was added 2-chloro-4-(mesityloxy)-5-methyl-5H-pyrrolo[3,2-d]pyrimidine (52.7 mg, 0.18 mmol), 4-aminobenzonitrile (83 mg, 0.70 mmol), TFE (1.0 mL) and TFA (0.11 mL, 1.44 mmol). The reaction mixture was stirred at 90° C. for 48 h. Upon completion of the reaction, the resulting mixture was cooled, diluted with water and washed with EtOAc. The combined organic layers were washed with NaHCO$_3$, brine, dried over Na$_2$SO$_4$, filtered, and concentrated in vacuo. The crude product was purified by preparative TLC, eluting with hexanes:ethyl acetate (5:1-2:1), to give the product as a light yellow solid

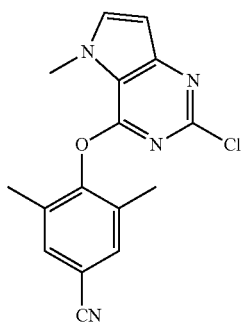 [SMILES: Cc1cc(C#N)cc(C)c1Oc1nc(Cl)nc2ccn(C)c12]

4-(2-Chloro-5-methyl-5H-pyrrolo[3,2-d]pyrimidin-4-yloxy)-3,5-dimethylbenzonitrile To a stirred solution of NaH (42.1 mg, 1.05 mmol) in dry NMP (2.5 mL) was added 4-hydroxy-3,5-dimethylbenzonitrile (154.7 mg, 1.05 mmol) and stirred at room temperature for 30 min under argon. The reaction mixture was added to a solution of 2,4-dichloro-5-methyl-5H-pyrrolo[3,2-d]pyrimidine (211.3 mg, 1.05 mmol) in dry NMP (2.7 mL) and heated at 160° C. for 16 h. After completion of the reaction, the resulting mixture was diluted with water and washed with EtOAc. The combined organic layers were washed with water, brine, dried over Na$_2$SO$_4$, filtered, and concentrated in vacuo. The crude product was purified by column chromatography, eluting with hexanes/ethyl acetate (3:1-1:1), to give the product as a light yellow solid (294 mg, 85%).

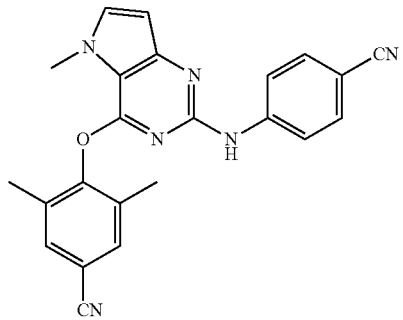 [SMILES: Cc1cc(C#N)cc(C)c1Oc1nc(Nc2ccc(C#N)cc2)nc2ccn(C)c12]

4-(2-(4-Cyanophenylamino)-5-methyl-5H-pyrrolo[3,2-d]pyrimidin-4-yloxy)-3,5-dimethylbenzonitrile In a sealed tube was added 4-(2-chloro-5-methyl-5H-pyrrolo[3,2-d]pyrimidin-4-yloxy)-3,5-dimethylbenzonitrile (294 mg, 0.94 mmol), 4-aminobenzonitrile (455 mg, 3.77 mmol), TFE (3.1 mL) and TFA (0.58 mL, 7.52 mmol). The reaction mixture was stirred at 90° C. for 48 h. Upon completion of the reaction, the resulting mixture was cooled, diluted with water and washed with EtOAc. The combined organic layers were washed with NaHCO$_3$, brine, dried over Na$_2$SO$_4$, filtered, and concentrated in vacuo. The crude product was purified by preparative TLC, eluting with hexanes:ethyl acetate (4:1-1:2), to give the product as an off-white solid (133 mg, 40%).

Example 13

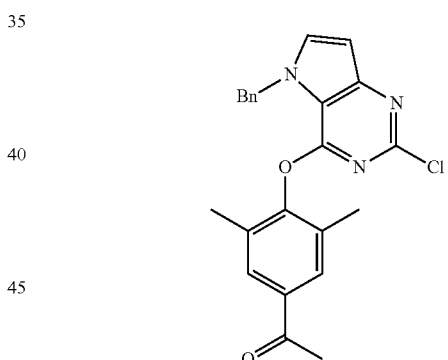

1-(4-(5-benzyl-2-chloro-5H-pyrrolo[3,2-d]pyrimidin-4-yloxy)-3,5-dimethylphenyl)ethanone To a stirred solution of NaH (31 mg, 0.78 mmol) in dry NMP (2 mL) was added 1-(4-hydroxy-3,5-dimethylphenyl)ethanone (127 mg, 0.78 mmol) and stirred at room temperature for 30 min under argon. The reaction mixture was added to a solution of 5-benzyl-2,4-dichloro-5H-pyrrolo[3,2-d]pyrimidine (216 mg, 0.78 mmol) in dry NMP (2.4 mL) and heated at 160° C. for 16 h. After completion of the reaction, the resulting mixture was diluted with water and washed with EtOAc. The combined organic layers were washed with water, 2% NaOH, brine, dried over Na$_2$SO$_4$, filtered, and concentrated in vacuo. The crude product was purified by column chromatography, eluting with hexanes/ethyl acetate (4:1-2:1), to give the product as a light yellow solid (111 mg, 35%).

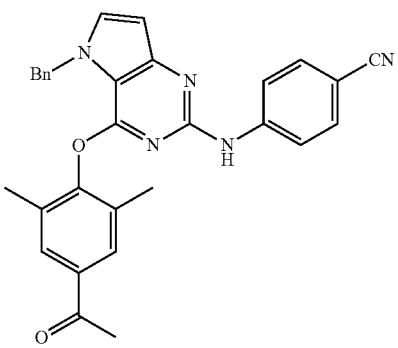 [SMILES: CC(=O)c1cc(C)c(Oc2nc(Nc3ccc(C#N)cc3)nc3ccn(Cc4ccccc4)c23)c(C)c1]

4-(4-(4-Acetyl-2,6-dimethylphenoxy)-5-benzyl-5H-pyrrolo[3,2-d]pyrimidin-2-ylamino)benzonitrile In a sealed tube was added 1-(4-(5-benzyl-2-chloro-5H-pyrrolo[3,2-d]pyrimidin-4-yloxy)-3,5-dimethylphenyl)ethanone (111 mg, 0.27 mmol), 4-aminobenzonitrile (129 mg, 1.1 mmol), TFE (1.7 mL) and TFA (0.2 mL, 2.16 mmol). The reaction mixture was stirred at 90° C. for 16 h. Upon completion of the reaction, the resulting mixture was cooled, diluted with water, and washed with EtOAc. The combined organic layers were washed with NaHCO$_3$ and brine; dried over Na$_2$SO$_4$; filtered; and concentrated in vacuo. The crude product was purified by silica gel column chromatography, eluting with hexanes:ethyl acetate (9:1-100% EtOAc), to give the product as an off-white solid (68 mg, 51%).

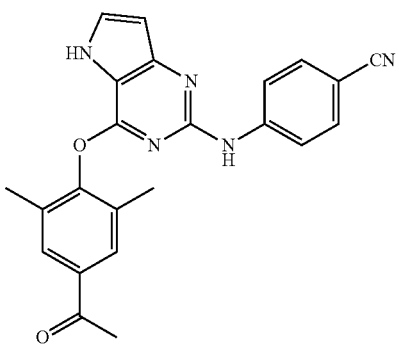 [SMILES: CC(=O)c1cc(C)c(Oc2nc(Nc3ccc(C#N)cc3)nc3cc[nH]c23)c(C)c1]

4-(4-(4-Acetyl-2,6-dimethylphenoxy)-5H-pyrrolo[3,2-d]pyrimidin-2-ylamino)benzonitrile To a suspension of 4-(4-(4-acetyl-2,6-dimethylphenoxy)-5-benzyl-5H-pyrrolo[3,2-d]pyrimidin-2-ylamino)benzonitrile (65 mg, 0.13 mmol) in 1,2-dichlorobenzene (5.3 mL) was added AlCl$_3$ (178 mg, 1.3 mmol). The reaction mixture was heated at 160° C. for 1.5 h, after which time the reaction mixture became dark and homogeneous. Upon completion of the reaction, the reaction mixture was cooled, CHCl$_3$ was added, and the mixture was washed with NH$_4$Cl. The combined organic layers were washed with brine, dried over Na$_2$SO$_4$, filtered, and concentrated in vacuo. The crude product was purified by silica gel column chromatography, eluting with hexanes:ethyl acetate (3:1), to give the product as a brown solid (41 mg, 77%).

Example 14

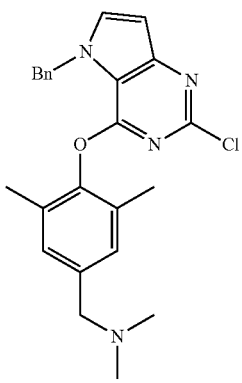 [SMILES: Cc1cc(CN(C)C)cc(C)c1Oc1nc(Cl)nc2ccn(Cc3ccccc3)c12]

1-(4-(5-benzyl-2-5H-pyrrolo[3,2-d]pyrimidin-4-yloxy)-3,5-dimethylphenyl)-N,N-dimethylmethanamine To a stirred solution of NaH (80.4 mg, 1.0 mmol) in dry NMP (3 mL) was added 4-((dimethylamino)methyl)-2,6-dimethylphenol (216.4 mg, 1.0 mmol) and the mixture was stirred at room temperature for 30 min under argon. The reaction mixture was added to a solution of 5-benzyl-2,4-dichloro-5H-pyrrolo[3,2-d]pyrimidine (216 mg, 0.78 mmol) in dry NMP (2.6 mL) and heated at 120° C. for 16 h. After completion of the reaction, the resulting mixture was diluted with water and washed with EtOAc. The combined organic layers were washed twice with water, washed with, brine, dried over Na$_2$SO$_4$, filtered, and concentrated in vacuo. The crude product was purified by silica gel column chromatography, eluting with MeOH/CH$_2$Cl$_2$ (10%-30%), to give the product as a tan solid (71 mg, 17%).

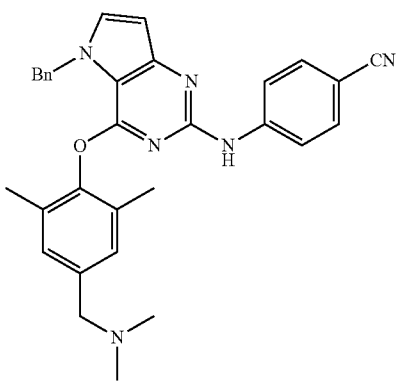 [SMILES: Cc1cc(CN(C)C)cc(C)c1Oc1nc(Nc2ccc(C#N)cc2)nc2ccn(Cc3ccccc3)c12]

4-(5-benzyl-4-(4-((dimethylamino)methyl)-2,6-dimethylphenoxy)-5H-pyrrolo[3,2-d]pyrimidin-2-ylamino)benzonitrile In a sealed tube was added 1-(4-(5-benzyl-2-5H-pyrrolo[3,2-d]pyrimidin-4-yloxy)-3,5-dimethylphenyl)-N,N-dimethylmethanamine (70.7 mg, 0.17 mmol), 4-aminobenzonitrile (78.9 mg, 0.67 mmol), TFE (1.1 mL) and TFA (0.1 mL, 1.3 mmol). The reaction mixture was stirred at 90° C. for 16 h. Upon completion of the reaction, the resulting mixture was cooled, diluted with water, and washed with EtOAc. The combined organic layers were washed with NaHCO$_3$ solution and with brine, dried over Na$_2$SO$_4$, filtered, and concentrated in vacuo. The crude product was purified by silica gel column chromatography, eluting with MeOH/CH$_2$Cl$_2$ (20%-40%), to give the product as a tan solid (17 mg, 20%).

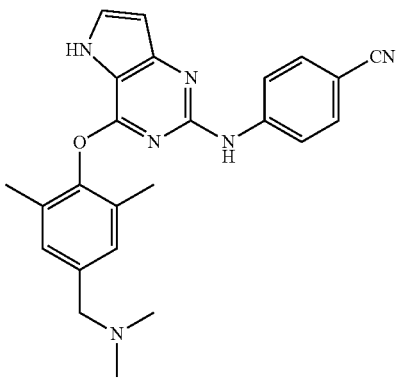 [SMILES: Cc1cc(CN(C)C)cc(C)c1Oc1nc(Nc2ccc(C#N)cc2)nc2cc[nH]c12]

4-(4-(4-((dimethylamino)methyl)-2,6-dimethylphenoxy)-5H-pyrrolo[3,2-d]pyrimidin-2-ylamino)benzonitrile The benzyl group was removed according to the same procedure as described for example 13.

Example 15

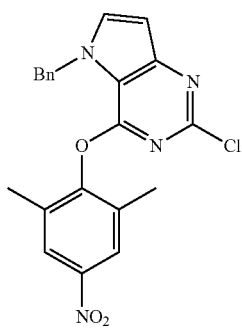 [SMILES: Cc1cc([N+](=O)[O-])cc(C)c1Oc1nc(Cl)nc2ccn(Cc3ccccc3)c12]

5-benzyl-2-chloro-4-(2,6-dimethyl-4-nitrophenoxy)-5H-pyrrolo[3,2-d]pyrimidine

To a stirred solution of NaH (61.9 mg, 2.6 mmol) in dry NMP (4.7 mL) was added 2,6-dimethyl-4-nitrophenol (258.9 mg, 1.55 mmol) and stirred at room temperature for 30 min under argon. The reaction mixture was added to a solution of 5-benzyl-2,4-dichloro-5H-pyrrolo[3,2-d]pyrimidine (431 mg, 1.55 mmol) in dry NMP (4 mL) and heated at 90° C. for 16 h. After completion of the reaction, the resulting mixture was diluted with water and washed with EtOAc. The combined organic layers were washed twice with water, washed with brine, dried over Na$_2$SO$_4$, filtered, and concentrated in vacuo. The crude product was purified by silica gel column chromatography, eluting with hexanes:ethyl acetate (3:1-1:1), to give the product as a white solid (598 mg, 94%).

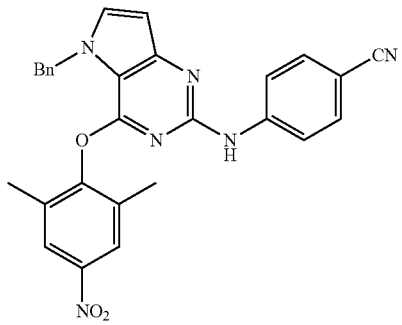 [SMILES: Cc1cc([N+](=O)[O-])cc(C)c1Oc1nc(Nc2ccc(C#N)cc2)nc2ccn(Cc3ccccc3)c12]

4-(5-benzyl-4-(2,6-dimethyl-4-nitrophenoxy)-5H-pyrrolo[3,2-d]pyrimidin-2-ylamino)benzonitrile In a sealed tube was added 5-benzyl-2-chloro-4-(2,6-dimethyl-4-nitrophenoxy)-5H-pyrrolo[3,2-d]pyrimidine (598 mg, 1.46 mmol), 4-aminobenzonitrile (691 mg, 5.85 mmol), TFE (9.1 mL) and TFA (1.97 mL, 11.7 mmol). The reaction mixture was stirred at 90° C. for 16 h. Upon completion of the reaction, the resulting mixture was cooled, diluted with water and washed with EtOAc. The combined organic layers were washed with NaHCO$_3$, brine, dried over Na$_2$SO$_4$, filtered, and concentrated in vacuo. The crude product was purified by silica gel column chromatography, eluting with hexanes:ethyl acetate (3:1-1:1), to give the product (442 mg, 60%).

Example 16

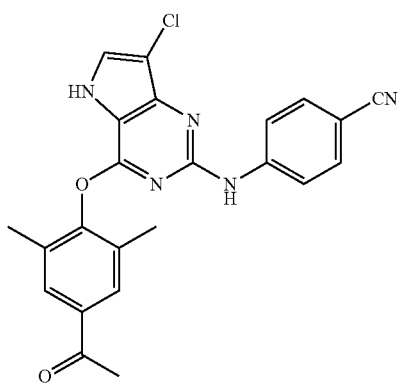 [SMILES: CC(=O)c1cc(C)c(Oc2nc(Nc3ccc(C#N)cc3)nc3c(Cl)c[nH]c23)c(C)c1]

4-(4-(4-Acetyl-2,6-dimethylphenoxy)-7-chloro-5H-pyrrolo[3,2-d]pyrimidin-2-ylamino)benzonitrile To a solution of 4-(4-(4-acetyl-2,6-dimethylphenoxy)-5H-pyrrolo[3,2-d]pyrimidin-2-ylamino)benzonitrile (13 mg, 0.03 mmol) in CH$_2$Cl$_2$ (1 mL) was added NCS (4.4 mg, 0.03 mmol) and the mixture refluxed for 16 h. After the completion of the reaction, the solvent was concentrated and purified by preparative TLC eluting with hexanes:ethyl acetate (2:1) to give the product (4.2 mg, 30%).

Example 17

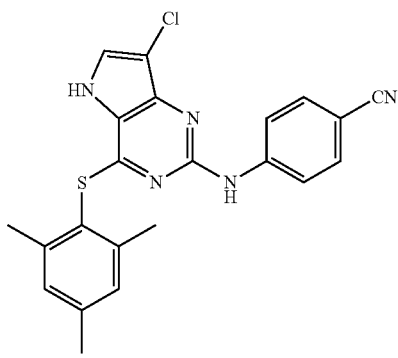

4-(7-Chloro-4-(mesitylthio)-5H-pyrrolo[3,2-d]pyrimidin-2-ylamino)benzonitrile

To a solution of 4-(4-(mesitylthio)-5H-pyrrolo[3,2-d]pyrimidin-2-ylamino)benzonitrile (10 mg, 0.02 mmol) in $CH_2Cl_2$ (5 mL) was added NCS (2.8 mg, 0.02 mmol) and the resolution mixture refluxed for 16 h. After the completion of the reaction, the solvent was concentrated and purified by preparative TLC, eluting with hexanes:ethyl acetate (3:1), to give the product (8.8 mg, 88%).

Example 18

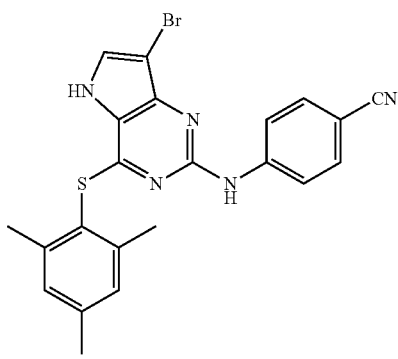 [SMILES: Cc1cc(C)c(Sc2nc(Nc3ccc(C#N)cc3)nc3c(Cl)c[nH]c23)c(C)c1]

4-(7-bromo-4-(mesitylthio)-5H-pyrrolo[3,2-d]pyrimidin-2-ylamino)benzonitrile

To a solution of 4-(4-(mesitylthio)-5H-pyrrolo[3,2-d]pyrimidin-2-ylamino)benzonitrile (22.7 mg, 0.06 mmol) in $CH_2Cl_2$ (10 mL) was added NBS (10.5 mg, 0.06 mmol) and the resultant mixture was refluxed for 16 h. After completion of the reaction, the solvent was concentrated and purified by reversed phase HPLC to give the product as a white solid (6.4 mg, 23%).

Example 19

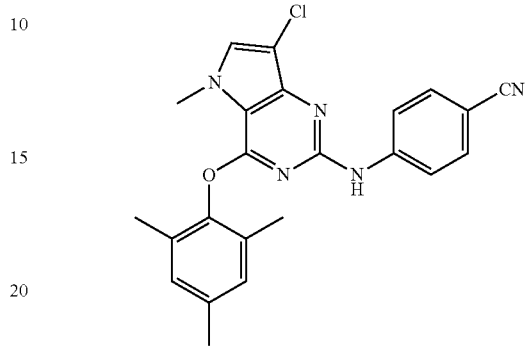

4-(7-chloro-4-(mesityloxy)-5-methyl-5H-pyrrolo[3,2-d]pyrimidin-2-ylamino)benzonitrile To a solution of 4-(4-(mesityloxy)-5-methyl-5H-pyrrolo[3,2-d]pyrimidin-2-ylamino)benzonitrile (17.3 mg, 0.05 mmol) in $CH_2Cl_2$ (5 mL) was added NCS (6.03 mg, 0.05 mmol) and the resultant mixture was refluxed for 16 h. After completion of the reaction, the solvent was concentrated and purified by preparative TLC, eluting with hexanes:ethyl acetate (3:1), to give the product as an off-white solid (3.4 mg, 6%).

Example 20

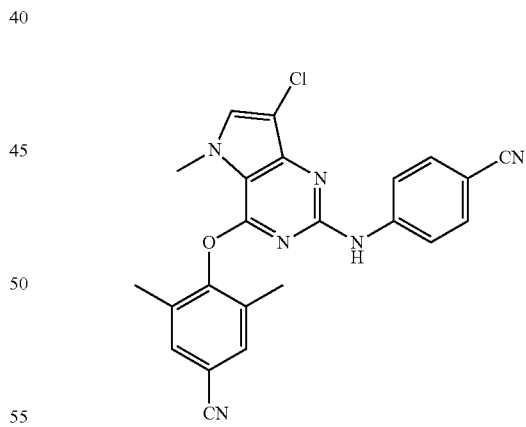

4-(7-Chloro-2-(4-cyanophenylamino)-5-methyl-5H-pyrrolo[3,2-d]pyrimidin-4-yloxy)-3,5-dimethylbenzonitrile To a solution of 4-(2-(4-cyanophenylamino)-5-methyl-5H-pyrrolo[3,2-a]pyrimidin-4-yloxy)-3,5-dimethylbenzonitrile (21.5 mg, 0.06 mmol) in $CH_2Cl_2$ (3 mL) was added NCS (7.3 mg, 0.06 mmol) and the resultant mixture was refluxed for 16 h. After completion of the reaction, the solvent was concentrated and purified by preparative TLC, eluting with Hexanes:Ethyl acetate (3:1), to give the product as a light yellow solid (13.2 mg, 56%).

Example 21

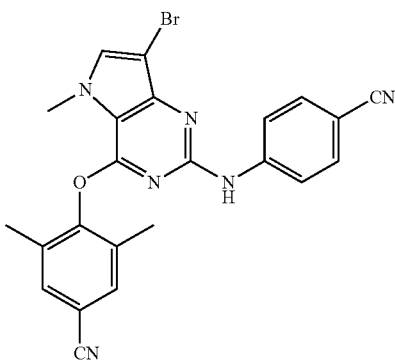

4-(7-Bromo-2-(4-cyanophenylamino)-5-methyl-5H-pyrrolo[3,2-d]pyrimidin-4-yloxy)-3,5-dimethylbenzonitrile To a solution of 4-(2-(4-cyanophenylamino)-5-methyl-5H-pyrrolo[3,2-d]pyrimidin-4-yloxy)-3,5-dimethylbenzonitrile (58 mg, 0.15 mmol) in $CH_2Cl_2$ (8 mL) was added NBS (29 mg, 0.16 mmol) and the resultant mixture was refluxed for 16 h. After completion of the reaction, the solvent was concentrated and purified by preparative TLC, eluting with hexanes:ethyl acetate (2:1), to give the product as a yellow solid (40 mg, 57%).

Example 22

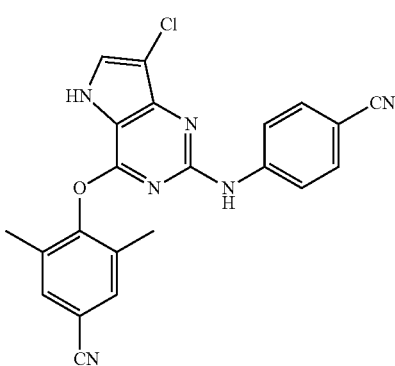 [SMILES: Cc1cc(C#N)cc(C)c1Oc1nc(Nc2ccc(C#N)cc2)nc2c(Cl)c[nH]c12]

4-(7-Chloro-2-(4-cyanophenylamino)-5H-pyrrolo[3,2-d]pyrimidin-4-yloxy)-3,5-dimethylbenzonitrile To a solution of 4-(2-(4-cyanophenylamino)-5H-pyrrolo[3,2-d]pyrimidin-4-yloxy)-3,5-dimethylbenzonitrile (28.1 mg, 0.07 mmol) in $CH_2Cl_2$ (4 mL) was added NCS (9.9 mg, 0.07 mmol) and the resultant mixture was refluxed for 16 h. After completion of the reaction, the solvent was concentrated and purified by preparative TLC eluting with hexanes: ethyl acetate (2:1), to give the product as a pink solid (20 mg, 65%).

Biological Activity

Inhibition of HIV-1 Reverse Transcriptase

Numerous compounds were screened for inhibitory activity against human immunodeficiency virus type 1 (HIV-1) using a high throughput cell-based assay using HIV-1 expressing firefly luciferase as a reporter gene and pseudotyped with vesicular stomatitis virus envelope glycoprotein (VSV-G). Experimental procedures were essentially as described by Connor et al. in *Journal of Virology* (1996), 70: 5306-5311 (Characterization of the functional properties of env genes from long-term survivors of human immunodeficiency virus type 1 infection), and Popik et al. in *Journal of Virology* (2002), 76: 4709-4722 (Human immunodeficiency virus type 1 uses lipid raft-co-localized CD4 and chemokine receptors for productive entry into CD4+ T cells). It should be particularly appreciated that the virus contains two introduced mutations in the RT gene (K103N and Y181C, created by PCR mutagenesis) that render the virus highly resistant to current non-nucleoside HIV-1 drugs. Virus stocks were generated by cotransfection of plasmid DNA encoding VSV-G with vector pNL4-3Env(−)Luc(+) into 293T cells. Sixty-four hours after transfection, virus-containing medium was collected by centrifugation and stored frozen at −80° C.

HeLa cells were infected with the VSV-G pseudotyped virus in the presence of screening compounds in a 384-well microtiter plate format. Forty-eight hours after initial infection, lysis buffer and Luciferase Assay Reagent (Promega) was added to the cells and luciferase activity was determined by counting the resultant luminescence using a LJL luminometer. Since the luciferase gene is carried in the virus genome, its expression level directly reflects the virus replication level in the presence of a compound.

To evaluate the activity of the compounds against wild type HIV-1, the HeLa-JC53 cell line that expresses high levels of CD4 and CCR5 (see e.g., Platt et al. in *Journal of Virology* (1998), 72: 2855-2864: Effect of CCR5 and CD4 cell surface concentrations on infection by macrophagetropic isolates of human immunodeficiency virus type 1) was modified by isolation of a stable cell line that expresses luciferase under the control of the HIV-1 promoter (long terminal repeat, i.e., LTR). HIV-1 infection of this cell line stimulates the transcription of luciferase from the HIV-1 promoter and the luciferase gene expression level is proportional to the level of virus replication (Harrington et al. in *Journal of Virology Methods* (2000), 88: 111-115: Direct detection of infection of HIV-1 in blood using a centrifugation-indicator cell assay; and Roos et al. in *Virology* (2000), 273: 307-315: LuSIV cells: a reporter cell line for the detection and quantitation of a single cycle of HIV and SW replication). Procedures for virus infection, compound testing and luciferase activity determination were the same as for the VSV-G pseudotyped HIV-1.

Two approaches were used to evaluate the cytotoxicity of the positive compounds discovered in the HIV-1 virus assays. The first approach employed another modified HeLa-JC53 cell line that constitutively expresses high level of luciferase without virus infection. The level of luciferase expression in these cells served as an indicator for cell replication in the presence of the compounds. Procedures for compound testing and luciferase activity determination were the same as for the virus infection tests. The other toxicity assay utilized HeLe-JC53 cells and a commercially available MTS assay kit (Promega) that measures the mitochondria function of the cells.

Results

The results are listed in Table A as EC50 (nM) and IC50 (nM). Table legend: A is <10, B is between 10 and 100, C is >100, ND is not determined. Note that many compounds of this invention exhibit activities on wild-type (WT) and resistant mutants below 10 nM.

TABLE A

| Cpd | Structure | EC$_{50}$ WT (nM) | EC$_{50}$ Y181C (nM) | EC$_{50}$ Y188L (nM) | EC$_{50}$ L100I-K103N (nM) |
|---|---|---|---|---|---|
| 1 | CLogP: 6.31119 | A | B | B | B |
| 2 | CLogP: 7.1942 | A | B | B | C |
| 3 | CLogP: 5.24519 | A | A | A | A |

TABLE A-continued
| Cpd | Structure | EC$_{50}$ WT (nM) | EC$_{50}$ Y181C (nM) | EC$_{50}$ Y188L (nM) | EC$_{50}$ L100I-K103N (nM) |
|---|---|---|---|---|---|
| 4 | 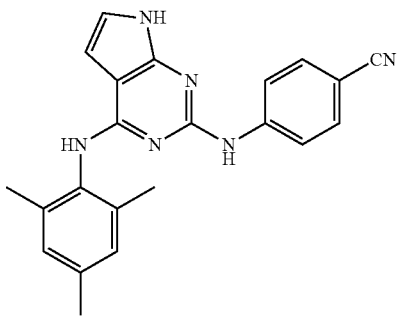 [SMILES: Cc1cc(C)c(Oc2nc(Nc3ccc(C#N)cc3)nc3[nH]ccc23)c(C)c1] CLogP: 7.00339 | A | B | B | B |
| 5 | 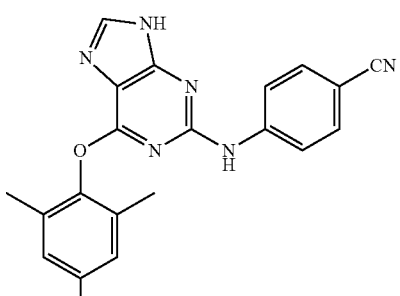 CLogP: 5.71888 | A | A | A | A |
| 6 | 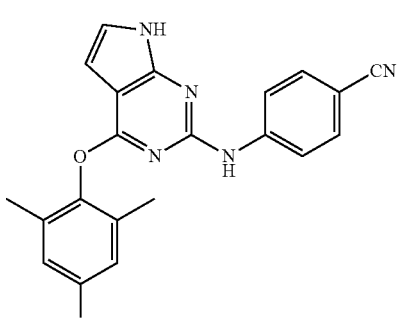 CLogP: 6.67519 | A | B | B | B |
| 7 | 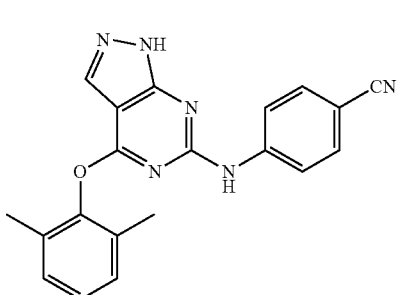 CLogP: 5.85982 | A | A | B | B |

TABLE A-continued

| Cpd | Structure | EC$_{50}$ WT (nM) | EC$_{50}$ Y181C (nM) | EC$_{50}$ Y188L (nM) | EC$_{50}$ L100I-K103N (nM) |
|---|---|---|---|---|---|
| 8 | CLogP: 8.36608 | B | C | C | C |
| 9 | CLogP: 5.81219 | A | C | C | C |
| 10 | CLogP: 6.65919 | A | B | B | B |
| 11 | CLogP: 6.5252 | A | B | A | B |

TABLE A-continued

| Cpd | Structure | EC$_{50}$ WT (nM) | EC$_{50}$ Y181C (nM) | EC$_{50}$ Y188L (nM) | EC$_{50}$ L100I-K103N (nM) |
|---|---|---|---|---|---|
| 12 | CLogP: 4.43498 | B | C | C | C |
| 13 | CLogP: 5.18408 | A | A | A | A |
| 14 | CLogP: 6.24839 | A | C | C | C |
| 15 | CLogP: 4.67978 | B | C | C | C |

| Cpd | Structure | EC$_{50}$ WT (nM) | EC$_{50}$ Y181C (nM) | EC$_{50}$ Y188L (nM) | EC$_{50}$ L100I-K103N (nM) |
|---|---|---|---|---|---|
| 16 | CLogP: 6.01359 | C | C | C | C |
| 17 | CLogP: 4.79382 | A | B | A | B |
| 18 | CLogP: 7.04473 | B | C | C | C |
| 19 | CLogP: 6.16288 | A | A | A | B |

TABLE A-continued

| Cpd | Structure | EC$_{50}$ WT (nM) | EC$_{50}$ Y181C (nM) | EC$_{50}$ Y188L (nM) | EC$_{50}$ L100I-K103N (nM) |
|---|---|---|---|---|---|
| 20 | CLogP: 6.67638 | A | B | C | C |
| 21 | CLogP: 6.10888 | A | B | B | C |
| 22 | CLogP: 7.12038 | A | C | C | C |
| 23 | CLogP: 6.50038 | A | A | A | B |

TABLE A-continued

| Cpd | Structure | EC$_{50}$ WT (nM) | EC$_{50}$ Y181C (nM) | EC$_{50}$ Y188L (nM) | EC$_{50}$ L100I-K103N (nM) |
|---|---|---|---|---|---|
| 24 | CLogP: 4.46648 | B | C | C | C |
| 25 | CLogP: 4.65288 | A | A | A | B |
| 26 | CLogP: 5.71308 | A | B | B | C |
| 27 | CLogP: 7.17134 | A | B | B | B |

TABLE A-continued

| Cpd | Structure | EC$_{50}$ WT (nM) | EC$_{50}$ Y181C (nM) | EC$_{50}$ Y188L (nM) | EC$_{50}$ L100I-K103N (nM) |
| --- | --- | --- | --- | --- | --- |
| 28 | CLogP: 6.94438 | A | A | B | B |
| 29 | CLogP: 6.01638 | A | C | C | C |
| 30 | CLogP: 5.42063 | C | C | C | C |
| 31 | CLogP: 6.34288 | A | B | A | B |

TABLE A-continued

| Cpd | Structure | EC$_{50}$ WT (nM) | EC$_{50}$ Y181C (nM) | EC$_{50}$ Y188L (nM) | EC$_{50}$ L100I-K103N (nM) |
|---|---|---|---|---|---|
| 32 | CLogP: 6.67638 | A | B | C | C |
| 33 | CLogP: 6.75519 | A | B | B | B |
| 34 | CLogP: 6.41174 | A | A | B | B |
| 35 | CLogP: 6.18265 | A | B | C | C |

TABLE A-continued
| Cpd | Structure | EC$_{50}$ WT (nM) | EC$_{50}$ Y181C (nM) | EC$_{50}$ Y188L (nM) | EC$_{50}$ L100I-K103N (nM) |
|---|---|---|---|---|---|
| 36 | 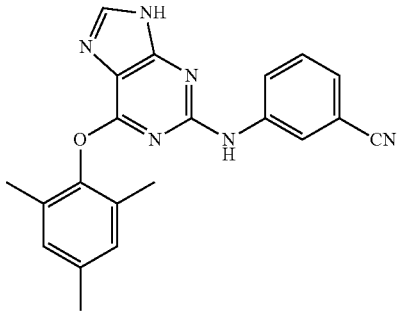 [SMILES: Cc1cc(C)c(Oc2nc(Nc3cccc(C#N)c3)nc3[nH]cnc23)c(C)c1] CLogP: 5.71888 | A | B | C | C |
| 37 | 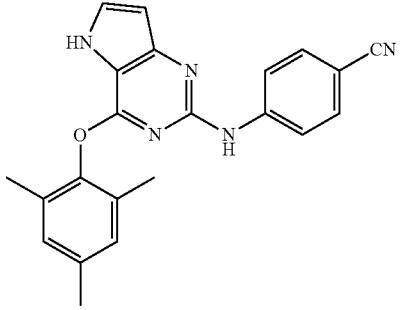 [SMILES: Cc1cc(C)c(Oc2nc(Nc3ccc(C#N)cc3)nc3cc[nH]c23)c(C)c1] CLogP;: 6.52119 | A | A | A | A |
| 38 | 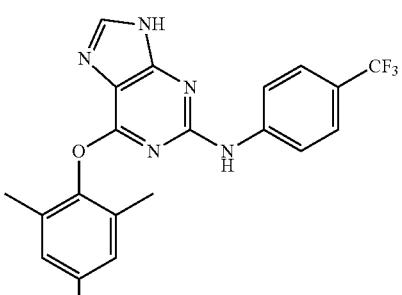 CLogP: 7.16147 | B | C | C | C |
| 39 | 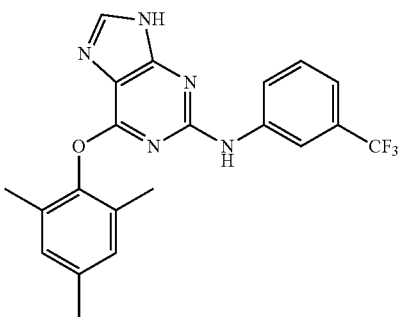 [SMILES: Cc1cc(C)c(Oc2nc(Nc3cccc(C(F)(F)F)c3)nc3[nH]cnc23)c(C)c1] CLogP: 7.16147 | C | C | C | C |

TABLE A-continued
| Cpd | Structure | EC$_{50}$ WT (nM) | EC$_{50}$ Y181C (nM) | EC$_{50}$ Y188L (nM) | EC$_{50}$ L100I-K103N (nM) |
|---|---|---|---|---|---|
| 40 | 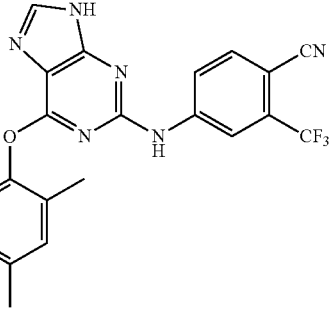 CLogP: 6.60982 | B | B | C | B |
| 41 | 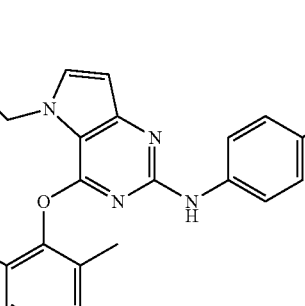 CLogP: 7.16208 | A | A | B | B |
| 42 | 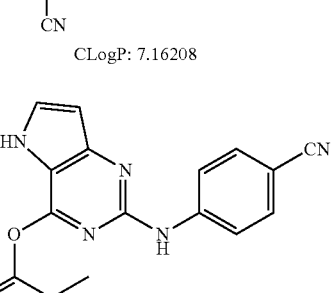 CLogP: 5.45519 | A | A | A | A |
| 43 | 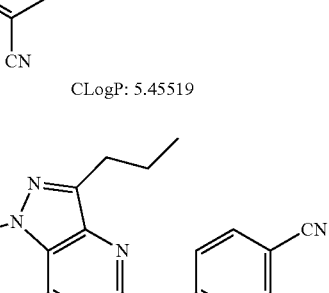 CLogP: 6.95418 | B | B | C | B |

TABLE A-continued

| Cpd | Structure | EC$_{50}$ WT (nM) | EC$_{50}$ Y181C (nM) | EC$_{50}$ Y188L (nM) | EC$_{50}$ L100I-K103N (nM) |
|---|---|---|---|---|---|
| 44 | CLogP: 7.19878 | B | C | C | C |
| 45 | CLogP: 5.46143 | A | A | A | B |
| 46 | CLogP: 6.29507 | C | C | C | C |
| 47 | CLogP: 8.67208 | B | B | C | C |

TABLE A-continued
| Cpd | Structure | EC₅₀ WT (nM) | EC₅₀ Y181C (nM) | EC₅₀ Y188L (nM) | EC₅₀ L100I-K103N (nM) |
|---|---|---|---|---|---|
| 48 | 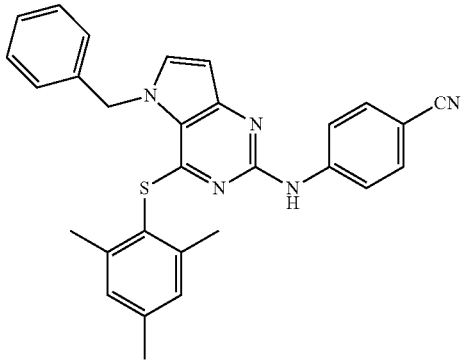 CLogP: 9.11123 | B | B | C | C |
| 49 | 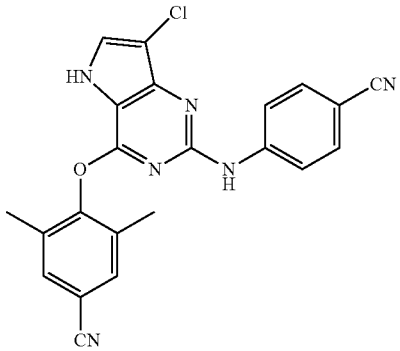 [SMILES: Cc1cc(C#N)cc(C)c1Oc1nc(Nc2ccc(C#N)cc2)nc2c(Cl)c[nH]c12] CLogP: 6.18873 | A | A | A | A |
| 50 | 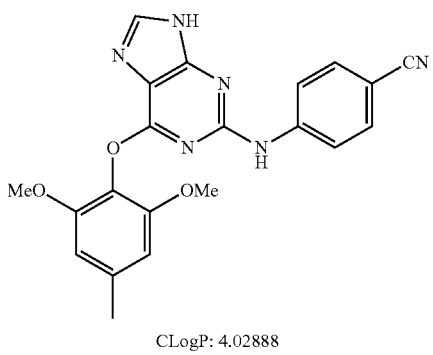 CLogP: 4.02888 | A | A | B | C |
| 51 | 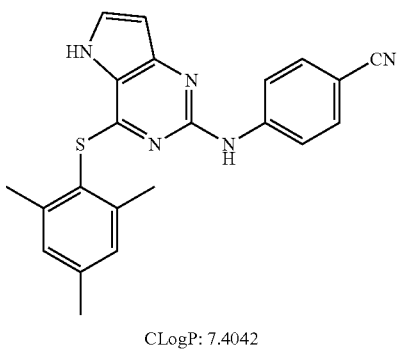 CLogP: 7.4042 | A | A | A | B |

TABLE A-continued

| Cpd | Structure | EC$_{50}$ WT (nM) | EC$_{50}$ Y181C (nM) | EC$_{50}$ Y188L (nM) | EC$_{50}$ L100I-K103N (nM) |
|---|---|---|---|---|---|
| 52 | CLogP: 6.96519 | A | A | A | A |
| 53 | CLogP: 8.13777 | A | B | B | C |
| 54 | CLogP: 9.83084 | A | B | B | C |
| 55 | CLogP: 8.28777 | A | B | B | C |

TABLE A-continued

| Cpd | Structure | EC$_{50}$ WT (nM) | EC$_{50}$ Y181C (nM) | EC$_{50}$ Y188L (nM) | EC$_{50}$ L100I-K103N (nM) |
|---|---|---|---|---|---|
| 56 | CLogP: 7.88168 | B | B | B | B |
| 57 | CLogP: 6.46008 | A | A | A | A |
| 58 | CLogP: 8.59208 | B | B | C | C |
| 59 | CLogP: 7.17968 | B | B | B | B |

TABLE A-continued

| Cpd | Structure | EC$_{50}$ WT (nM) | EC$_{50}$ Y181C (nM) | EC$_{50}$ Y188L (nM) | EC$_{50}$ L100I-K103N (nM) |
|---|---|---|---|---|---|
| 60 | CLogP: 7.16808 | A | A | B | B |
| 61 | CLogP: 5.46119 | A | A | A | A |
| 62 | CLogP: 7.39368 | A | A | A | A |
| 63 | CLogP: 8.44208 | B | B | C | C |

TABLE A-continued
| Cpd | Structure | EC$_{50}$ WT (nM) | EC$_{50}$ Y181C (nM) | EC$_{50}$ Y188L (nM) | EC$_{50}$ L100I-K103N (nM) |
|---|---|---|---|---|---|
| 64 | 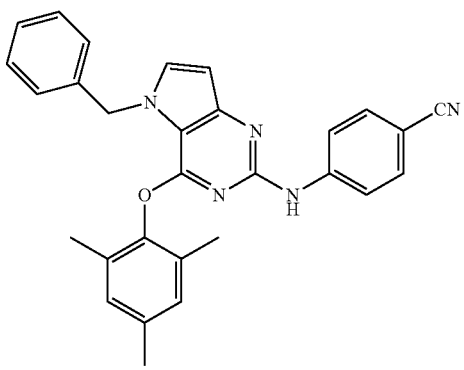 [SMILES: Cc1cc(C)c(Oc2nc(Nc3ccc(C#N)cc3)nc3ccn(Cc4ccccc4)c23)c(C)c1]<br>CLogP: 8.22808 | A | B | C | C |
| 65 | 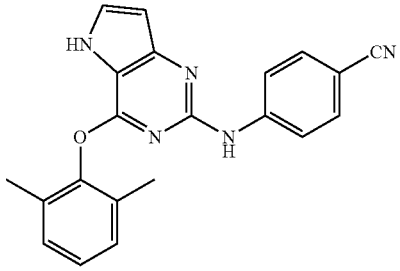 [SMILES: Cc1cccc(C)c1Oc1nc(Nc2ccc(C#N)cc2)nc2cc[nH]c12]<br>CLogP: 6.02219 | A | A | A | C |
| 66 | 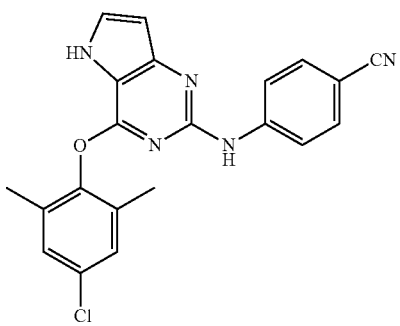<br>CLogP: 6.73519 | A | A | A | A |
| 67 | 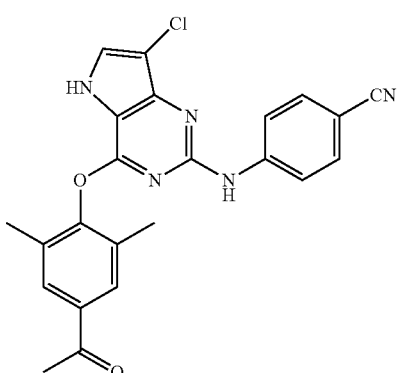<br>CLogP: 6.19473 | A | A | B | A |

TABLE A-continued

| Cpd | Structure | EC$_{50}$ WT (nM) | EC$_{50}$ Y181C (nM) | EC$_{50}$ Y188L (nM) | EC$_{50}$ L100I-K103N (nM) |
|---|---|---|---|---|---|
| 68 | CLogP: 5.39408 | A | A | A | A |
| 69 | CLogP: 6.11368 | A | A | A | A |
| 70 | CLogP: 6.26368 | A | A | A | A |
| 71 | CLogP: 6.86919 | A | A | A | A |

Contemplated Compounds and Prophetic Examples

In addition to the examples listed above, this invention provides or contemplates many compounds, examples of which are shown in the tables that follow.

TABLE 1

Contemplated Compounds of Formula IA-1

IA-1

|  | Ar | V | W | Z |
|---|---|---|---|---|
| 1. | o,o'-diCH$_3$O-p-(CH=CHCN)phenyl | CN | H | CH$_3$ |
| 2. | o,o'-diCH$_3$O-p-(CH=CHCN)phenyl | CN | benzyl | CH$_3$ |
| 3. | o,o'-diCH$_3$O-p-(CH=CHCN)phenyl | CN | benzyl | H |
| 4. | o,o'-diCH$_3$O-p-(CH=CHCN)phenyl | CN | 3-Me-benzyl | CH$_3$ |
| 5. | o,o'-diCH$_3$O-p-(CH=CHCN)phenyl | CN | 4-Me-benzyl | H |
| 6. | o,o'-diCH$_3$O-p-(CH=CHCN)phenyl | CN | 3-MeO-benzyl | H |
| 7. | o,o'-diCH$_3$O-p-(CH=CHCN)phenyl | CN | 4-MeO-benzyl | CH$_3$ |
| 8. | o,o'-diCH$_3$O-p-(CH=CHCN)phenyl | CN | H | H |
| 9. | o,o'-diCH$_3$O-p-(CH=CHCN)phenyl | CN | H | Br |
| 10. | o,o'-diCH$_3$O-p-(CH=CHCN)phenyl | CN | cyclopropyl | CH$_2$CH$_3$ |
| 11. | o,o'-diCH$_3$O-p-(CH=CHCN)phenyl | CN | CH$_2$CF$_3$ | CH$_2$CH$_3$ |
| 12. | o,o'-diCH$_3$O-p-(CH=CHCN)phenyl | CH=CHCN | H | CH$_3$ |
| 13. | o,o'-diCH$_3$O-p-(CH=CHCN)phenyl | CH=CHCN | benzyl | CH$_3$ |
| 14. | o,o'-diCH$_3$O-p-(CH=CHCN)phenyl | CH=CHCN | benzyl | H |
| 15. | o,o'-diCH$_3$O-p-(CH=CHCN)phenyl | CH=CHCN | 3-Me-benzyl | cyclopropyl |
| 16. | o,o'-diCH$_3$O-p-(CH=CHCN)phenyl | CH=CHCN | 3-MeO-benzyl | benzyl |
| 17. | o,o'-diCH$_3$O-p-(CH=CHCN)phenyl | CH=CHCN | H | H |
| 18. | o,o'-diCH$_3$O-p-(CH=CHCN)phenyl | C≡CCH$_3$ | CH$_2$CH$_3$ | CH$_3$ |
| 19. | o,o'-diCH$_3$O-p-(CH=CHCN)phenyl | Cl | CH$_2$CH=CH$_2$ | H |
| 20. | o,o'-diCH$_3$O-p-(CH=CHCN)phenyl | SO$_2$CH$_3$ | CH$_2$CH=CH$_2$ | H |
| 21. | o,o'-diCH$_3$O-p-(CH=CHCN)phenyl | Cl | CH$_2$CH$_3$ | CH$_2$CH$_3$ |
| 22. | o,o'-diCH$_3$O-p-(CH=CHCN)phenyl | Cl | H | H |
| 23. | 4-cyclopropylnaphth-1-yl | CN | H | CH$_3$ |
| 24. | 4-cyclopropylnaphth-1-yl | CN | benzyl | CH$_3$ |
| 25. | 4-cyclopropylnaphth-1-yl | CN | benzyl | H |
| 26. | 4-cyclopropylnaphth-1-yl | CN | H | H |
| 27. | 4-cyclopropylnaphth-1-yl | CH=CHCN | H | CH$_3$ |
| 28. | 4-cyclopropylnaphth-1-yl | CH=CHCN | benzyl | CH$_3$ |
| 29. | 4-cyclopropylnaphth-1-yl | CH=CHCN | benzyl | H |
| 30. | 4-cyclopropylnaphth-1-yl | CH=CHCN | H | H |
| 31. | 4-cyclopropylnaphth-1-yl | SO$_2$NHCH$_3$ | CH$_2$CN | F |
| 32. | 4-cyclopropylnaphth-1-yl | SO$_2$NHCH$_3$ | cyclopropyl | Cl |
| 33. | o,o'-di-CH$_3$O-p-CN-phenyl | SO$_2$NH$_2$ | CH$_2$CH$_2$CN | Br |
| 34. | o,o'-di-CH$_3$O-p-CN-phenyl | SO$_2$NH$_2$ | CH$_2$CN | benzyl |
| 35. | o,o'-di-CH$_3$O-p-CN-phenyl | C≡CCH$_3$ | 3-MeO-benzyl | F |
| 36. | o,o'-di-CH$_3$O-p-CN-phenyl | F | 3-Me-benzyl | Cl |
| 37. | o,o'-di-CH$_3$O-p-CN-phenyl | CN | H | CH$_3$ |
| 38. | o,o'-di-CH$_3$O-p-CN-phenyl | CN | benzyl | CH$_3$ |
| 39. | o,o'-di-CH$_3$O-p-CN-phenyl | CN | benzyl | H |
| 40. | o,o'-di-CH$_3$O-p-CN-phenyl | CN | H | H |
| 41. | o,o'-di-CH$_3$O-p-CN-phenyl | CH=CHCN | H | CH$_3$ |
| 42. | o,o'-di-CH$_3$O-p-CN-phenyl | CH=CHCN | benzyl | CH$_3$ |
| 43. | o,o'-di-CH$_3$O-p-CN-phenyl | CH=CHCN | benzyl | H |
| 44. | o,o'-di-CH$_3$O-p-CN-phenyl | CH=CHCN | H | H |
| 45. | o,o'-di-CH$_3$-p-CN-phenyl | CN | H | CH$_3$ |
| 46. | o,o'-di-CH$_3$-p-CN-phenyl | CN | benzyl | CH$_3$ |
| 47. | o,o'-di-CH$_3$-p-CN-phenyl | CN | 3,5-di MeO-benzyl | CH$_3$ |
| 48. | o,o'-di-CH$_3$-p-CN-phenyl | CN | benzyl | H |
| 49. | o,o'-di-CH$_3$-p-CN-phenyl | CN | H | H |
| 50. | o,o'-di-CH$_3$-p-CN-phenyl | CH=CHCN | H | CH$_3$ |
| 51. | o,o'-di-CH$_3$-p-CN-phenyl | CH=CHCN | benzyl | CH$_3$ |
| 52. | o,o'-di-CH$_3$-p-CN-phenyl | CH=CHCN | benzyl | H |
| 53. | o,o'-di-CH$_3$-p-CN-phenyl | CH=CHCN | H | H |
| 54. | o,o'-diCH$_3$O-p-(CH=CHCN)phenyl | CN | H | F |
| 55. | o,o'-diCH$_3$O-p-(CH=CHCN)phenyl | CN | benzyl | F |
| 56. | o,o'-diCH$_3$O-p-(CH=CHCN)phenyl | CH=CHCN | benzyl | F |
| 57. | o,o'-diCH$_3$O-p-(CH=CHCN)phenyl | CH=CHCN | H | F |

TABLE 1-continued

Contemplated Compounds of Formula IA-1

IA-1

|  | Ar | V | W | Z |
|---|---|---|---|---|
| 58. | 4-cyclopropylnaphth-1-yl | CN | H | F |
| 59. | 4-cyclopropylnaphth-1-yl | CN | benzyl | F |
| 60. | 4-cyclopropylnaphth-1-yl | CH=CHCN | H | F |
| 61. | 4-cyclopropylnaphth-1-yl | CH=CHCN | benzyl | F |
| 62. | o,o'-di-CH₃O-p-CN-phenyl | CN | H | F |
| 63. | o,o'-di-CH₃O-p-CN-phenyl | CN | benzyl | F |
| 64. | o,o'-di-CH₃O-p-CN-phenyl | CH=CHCN | H | F |
| 65. | o,o'-di-CH₃O-p-CN-phenyl | CH=CHCN | benzyl | F |
| 66. | o,o'-di-CH₃-p-CN-phenyl | CN | H | F |
| 67. | o,o'-di-CH₃-p-CN-phenyl | CN | benzyl | F |
| 68. | o,o'-di-CH₃-p-CN-phenyl | CH=CHCN | H | F |
| 69. | o,o'-di-CH₃-p-CN-phenyl | CH=CHCN | benzyl | F |
| 70. | o,o'-diCH₃O-p-(CH=CHCN)phenyl | SO₂NH₂ | H | CH₃ |
| 71. | o,o'-diCH₃O-p-(CH=CHCN)phenyl | SO₂NH₂ | benzyl | CH₃ |
| 72. | o,o'-diCH₃O-p-(CH=CHCN)phenyl | SO₂NH₂ | benzyl | H |
| 73. | o,o'-diCH₃O-p-(CH=CHCN)phenyl | SO₂NH₂ | H | H |
| 74. | o,o'-diCH₃O-p-(CH=CHCN)phenyl | SO₂NH₂ | H | CH₃ |
| 75. | o,o'-diCH₃O-p-(CH=CHCN)phenyl | F | benzyl | CH₃ |
| 76. | o,o'-diCH₃O-p-(CH=CHCN)phenyl | F | benzyl | H |
| 77. | o,o'-diCH₃O-p-(CH=CHCN)phenyl | F | H | H |
| 78. | 4-cyclopropylnaphth-1-yl | SO₂NH₂ | H | CH₃ |
| 79. | 4-cyclopropylnaphth-1-yl | SO₂NH₂ | benzyl | CH₃ |
| 80. | 4-cyclopropylnaphth-1-yl | SO₂NH₂ | benzyl | H |
| 81. | 4-cyclopropylnaphth-1-yl | SO₂NH₂ | H | H |
| 82. | 4-cyclopropylnaphth-1-yl | F | H | CH₃ |
| 83. | 4-cyclopropylnaphth-1-yl | F | benzyl | CH₃ |
| 84. | 4-cyclopropylnaphth-1-yl | F | benzyl | H |
| 85. | 4-cyclopropylnaphth-1-yl | F | H | H |
| 86. | o,o'-di-CH₃O-p-CN-phenyl | SO₂NH₂ | H | CH₃ |
| 87. | o,o'-di-CH₃O-p-CN-phenyl | SO₂NH₂ | benzyl | CH₃ |
| 88. | o,o'-di-CH₃O-p-CN-phenyl | SO₂NH₂ | benzyl | H |
| 89. | o,o'-di-CH₃O-p-CN-phenyl | SO₂NH₂ | H | H |
| 90. | o,o'-di-CH₃O-p-CN-phenyl | F | H | CH₃ |
| 91. | o,o'-di-CH₃O-p-CN-phenyl | F | benzyl | CH₃ |
| 92. | o,o'-di-CH₃O-p-CN-phenyl | F | benzyl | H |
| 93. | o,o'-di-CH₃O-p-CN-phenyl | F | H | H |
| 94. | o,o'-di-CH₃-p-CN-phenyl | SO₂NH₂ | H | CH₃ |
| 95. | o,o'-di-CH₃-p-CN-phenyl | SO₂NH₂ | benzyl | CH₃ |
| 96. | o,o'-di-CH₃-p-CN-phenyl | SO₂NH₂ | 3-Me-benzyl | CH₃ |
| 97. | o,o'-di-CH₃-p-CN-phenyl | SO₂NHCH₃ | benzyl | H |
| 98. | o,o'-di-CH₃-p-CN-phenyl | SO₂NH₂ | benzyl | H |
| 99. | o,o'-di-CH₃-p-CN-phenyl | SO₂NH₂ | H | H |
| 100. | o,o'-di-CH₃-p-CN-phenyl | F | H | CH₃ |
| 101. | o,o'-di-CH₃-p-CN-phenyl | F | benzyl | CH₃ |
| 102. | o,o'-di-CH₃-p-CN-phenyl | F | benzyl | H |
| 103. | o,o'-di-CH₃-p-CN-phenyl | F | H | H |
| 104. | o,o'-diCH₃O-p-(CH=CHCN)phenyl | SO₂NH₂ | H | F |
| 105. | o,o'-diCH₃O-p-(CH=CHCN)phenyl | SO₂NH₂ | benzyl | F |
| 106. | o,o'-diCH₃O-p-(CH=CHCN)phenyl | F | benzyl | F |
| 107. | o,o'-diCH₃O-p-(CH=CHCN)phenyl | F | H | F |
| 108. | 4-cyclopropylnaphth-1-yl | SO₂NH₂ | H | F |
| 109. | 4-cyclopropylnaphth-1-yl | SO₂NH₂ | benzyl | F |
| 110. | 4-cyclopropylnaphth-1-yl | F | H | F |
| 111. | 4-cyclopropylnaphth-1-yl | F | benzyl | F |
| 112. | o,o'-di-CH₃O-p-CN-phenyl | SO₂NH₂ | H | F |
| 113. | o,o'-di-CH₃O-p-CN-phenyl | SO₂NH₂ | benzyl | F |
| 114. | o,o'-di-CH₃O-p-CN-phenyl | F | H | F |
| 115. | o,o'-di-CH₃O-p-CN-phenyl | F | benzyl | F |
| 116. | o,o'-di-CH₃-p-CN-phenyl | SO₂NH₂ | H | F |
| 117. | o,o'-di-CH₃-p-CN-phenyl | SO₂NH₂ | benzyl | F |
| 118. | o,o'-di-CH₃-p-CN-phenyl | F | H | F |
| 119. | o,o'-di-CH₃-p-CN-phenyl | F | benzyl | F |
| 120. | 2,4,6-trimethyl phenyl | CN | H | CH₃ |

TABLE 1-continued

Contemplated Compounds of Formula IA-1

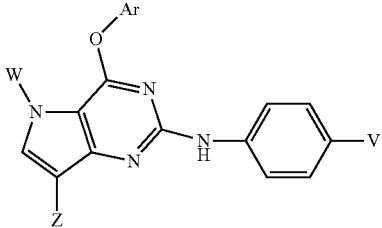

IA-1

| | Ar | V | W | Z |
|---|---|---|---|---|
| 121. | 2,4,6-trimethyl phenyl | CN | benzyl | $CH_3$ |
| 122. | 2,4,6-trimethyl phenyl | CN | benzyl | H |
| 123. | 2,4,6-trimethyl phenyl | CN | H | H |
| 124. | 2,4,6-trimethyl phenyl | CH=CHCN | H | $CH_3$ |
| 125. | 2,4,6-trimethyl phenyl | CH=CHCN | benzyl | $CH_3$ |
| 126. | 2,4,6-trimethyl phenyl | CH=CHCN | benzyl | H |
| 127. | 2,4,6-trimethyl phenyl | CH=CHCN | H | H |
| 128. | 2,4,6-trimethyl phenyl | CN | H | F |
| 129. | 2,4,6-trimethyl phenyl | CN | benzyl | F |
| 130. | 2,4,6-trimethyl phenyl | CH=CHCN | H | F |
| 131. | 2,4,6-trimethyl phenyl | CH=CHCN | benzyl | F |
| 132. | 2,4,6-trimethyl phenyl | $SO_2NH_2$ | H | $CH_3$ |
| 133. | 2,4,6-trimethyl phenyl | $SO_2NH_2$ | benzyl | $CH_3$ |
| 134. | 2,4,6-trimethyl phenyl | $SO_2NH_2$ | benzyl | H |
| 135. | 2,4,6-trimethyl phenyl | $SO_2NH_2$ | H | H |
| 136. | 2,4,6-trimethyl phenyl | F | H | $CH_3$ |
| 137. | 2,4,6-trimethyl phenyl | F | benzyl | $CH_3$ |
| 138. | 2,4,6-trimethyl phenyl | F | benzyl | H |
| 139. | 4-cyclopropyl phenyl | F | H | H |
| 140. | 4-cyclopropyl phenyl | $SO_2NH_2$ | H | F |
| 141. | 4-cyclopropyl phenyl | $SO_2NH_2$ | benzyl | F |
| 142. | 4-cyclopropyl phenyl | F | H | F |
| 143. | 4-cyclopropyl phenyl | F | benzyl | F |
| 144. | o,o'-dimethyl-p-cyclopropyl phenyl | CN | H | $CH_3$ |
| 145. | o,o'-dimethyl-p-cyclopropyl phenyl | CN | benzyl | $CH_3$ |
| 146. | o,o'-dimethyl-p-cyclopropyl phenyl | CN | benzyl | H |
| 147. | o,o'-dimethyl-p-cyclopropyl phenyl | CN | H | H |
| 148. | o,o'-dimethyl-p-cyclopropyl phenyl | CH=CHCN | H | $CH_3$ |
| 149. | o,o'-dimethyl-p-cyclopropyl phenyl | CH=CHCN | benzyl | $CH_3$ |
| 150. | o,o'-dimethyl-p-cyclopropyl phenyl | CH=CHCN | benzyl | H |
| 151. | o,o'-dimethyl-p-cyclopropyl phenyl | CH=CHCN | H | H |
| 152. | o,o'-dimethyl-p-cyclopropyl phenyl | CN | H | F |
| 153. | o,o'-dimethyl-p-cyclopropyl phenyl | CN | benzyl | F |
| 154. | o,o'-dimethyl-p-cyclopropyl phenyl | CH=CHCN | H | F |
| 155. | o,o'-dimethyl-p-cyclopropyl phenyl | CH=CHCN | benzyl | F |
| 156. | o,o'-dimethyl-p-cyclopropyl phenyl | $SO_2NH_2$ | H | $CH_3$ |
| 157. | o,o'-dimethyl-p-cyclopropyl phenyl | $SO_2NH_2$ | benzyl | $CH_3$ |
| 158. | o,o'-dimethyl-p-cyclopropyl phenyl | $SO_2NH_2$ | benzyl | H |
| 159. | o,o'-dimethyl-p-cyclopropyl phenyl | $SO_2NH_2$ | H | H |
| 160. | o,o'-dimethyl-p-cyclopropyl phenyl | F | H | $CH_3$ |
| 161. | o,o'-dimethyl-p-cyclopropyl phenyl | F | benzyl | $CH_3$ |
| 162. | o,o'-dimethyl-p-cyclopropyl phenyl | F | benzyl | H |
| 163. | o,o'-dimethyl-p-cyclopropyl phenyl | F | H | H |
| 164. | o,o'-dimethyl-p-cyclopropyl phenyl | $SO_2NH_2$ | H | F |
| 165. | o,o'-dimethyl-p-cyclopropyl phenyl | $SO_2NH_2$ | benzyl | F |
| 166. | o,o'-dimethyl-p-cyclopropyl phenyl | F | H | F |
| 167. | o,o'-dimethyl-p-cyclopropyl phenyl | F | benzyl | F |
| 168. | o,o'-di$CH_3$O-p-(CH=CHCN)phenyl | CN | $CH_3$ | $CH_3$ |
| 169. | o,o'-di$CH_3$O-p-(CH=CHCN)phenyl | CN | cyclopropyl | $CH_3$ |
| 170. | o,o'-di$CH_3$O-p-(CH=CHCN)phenyl | CN | cyclopropyl | H |
| 171. | o,o'-di$CH_3$O-p-(CH=CHCN)phenyl | CN | $CH_3$ | H |
| 172. | o,o'-di$CH_3$O-p-(CH=CHCN)phenyl | CN | $CH_3$ | $CH_3$ |
| 173. | o,o'-di$CH_3$O-p-(CH=CHCN)phenyl | CH=CHCN | cyclopropyl | $CH_3$ |
| 174. | o,o'-di$CH_3$O-p-(CH=CHCN)phenyl | CH=CHCN | cyclopropyl | H |
| 175. | o,o'-di$CH_3$O-p-(CH=CHCN)phenyl | CH=CHCN | $CH_3$ | H |
| 176. | 4-cyclopropylnaphth-1-yl | CN | $CH_3$ | $CH_3$ |
| 177. | 4-cyclopropylnaphth-1-yl | CN | cyclopropyl | $CH_3$ |
| 178. | 4-cyclopropylnaphth-1-yl | CN | cyclopropyl | H |
| 179. | 4-cyclopropylnaphth-1-yl | CN | $CH_3$ | H |
| 180. | 4-cyclopropylnaphth-1-yl | CH=CHCN | $CH_3$ | $CH_3$ |
| 181. | 4-cyclopropylnaphth-1-yl | CH=CHCN | cyclopropyl | $CH_3$ |
| 182. | 4-cyclopropylnaphth-1-yl | CH=CHCN | cyclopropyl | H |
| 183. | 4-cyclopropylnaphth-1-yl | CH=CHCN | $CH_3$ | H |

TABLE 1-continued

Contemplated Compounds of Formula IA-1

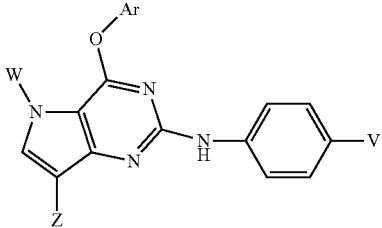

IA-1

| | Ar | V | W | Z |
|---|---|---|---|---|
| 184. | o,o'-di-CH₃O-p-CN-phenyl | CN | CH₃ | CH₃ |
| 185. | o,o'-di-CH₃O-p-CN-phenyl | CN | cyclopropyl | CH₃ |
| 186. | o,o'-di-CH₃O-p-CN-phenyl | CN | cyclopropyl | H |
| 187. | o,o'-di-CH₃O-p-CN-phenyl | CN | CH₃ | H |
| 188. | o,o'-di-CH₃O-p-CN-phenyl | CH=CHCN | CH₃ | CH₃ |
| 189. | o,o'-di-CH₃O-p-CN-phenyl | CH=CHCN | cyclopropyl | CH₃ |
| 190. | o,o'-di-CH₃O-p-CN-phenyl | CH=CHCN | cyclopropyl | H |
| 191. | o,o'-di-CH₃O-p-CN-phenyl | CH=CHCN | CH₃ | H |
| 192. | o,o'-di-CH₃-p-CN-phenyl | CN | CH₃ | CH₃ |
| 193. | o,o'-di-CH₃-p-CN-phenyl | CN | cyclopropyl | CH₃ |
| 194. | o,o'-di-CH₃-p-CN-phenyl | CN | cyclopropyl | H |
| 195. | o,o'-di-CH₃-p-CN-phenyl | CN | CH₃ | H |
| 196. | o,o'-di-CH₃-p-CN-phenyl | CH=CHCN | CH₃ | CH₃ |
| 197. | o,o'-di-CH₃-p-CN-phenyl | CH=CHCN | cyclopropyl | CH₃ |
| 198. | o,o'-di-CH₃-p-CN-phenyl | CH=CHCN | cyclopropyl | H |
| 199. | o,o'-di-CH₃-p-CN-phenyl | CH=CHCN | CH₃ | H |
| 200. | o,o'-diCH₃O-p-(CH=CHCN)phenyl | CN | CH₃ | F |
| 201. | o,o'-diCH₃O-p-(CH=CHCN)phenyl | CN | cyclopropyl | F |
| 202. | o,o'-diCH₃O-p-(CH=CHCN)phenyl | CH=CHCN | cyclopropyl | F |
| 203. | o,o'-diCH₃O-p-(CH=CHCN)phenyl | CH=CHCN | CH₃ | F |
| 204. | 4-cyclopropylnaphth-1-yl | CN | CH₃ | F |
| 205. | 4-cyclopropylnaphth-1-yl | CN | cyclopropyl | F |
| 206. | 4-cyclopropylnaphth-1-yl | CH=CHCN | CH₃ | F |
| 207. | 4-cyclopropylnaphth-1-yl | CH=CHCN | cyclopropyl | F |
| 208. | o,o'-di-CH₃O-p-CN-phenyl | CN | CH₃ | F |
| 209. | o,o'-di-CH₃O-p-CN-phenyl | CN | cyclopropyl | F |
| 210. | o,o'-di-CH₃O-p-CN-phenyl | CH=CHCN | CH₃ | F |
| 211. | o,o'-di-CH₃O-p-CN-phenyl | CH=CHCN | cyclopropyl | F |
| 212. | o,o'-di-CH₃-p-CN-phenyl | CN | CH₃ | F |
| 213. | o,o'-di-CH₃-p-CN-phenyl | CN | cyclopropyl | F |
| 214. | o,o'-di-CH₃-p-CN-phenyl | CH=CHCN | CH₃ | F |
| 215. | o,o'-di-CH₃-p-CN-phenyl | CH=CHCN | cyclopropyl | F |
| 216. | o,o'-diCH₃O-p-(CH=CHCN)phenyl | SO₂NH₂ | CH₃ | CH₃ |
| 217. | o,o'-diCH₃O-p-(CH=CHCN)phenyl | SO₂NH₂ | cyclopropyl | CH₃ |
| 218. | o,o'-diCH₃O-p-(CH=CHCN)phenyl | SO₂NH₂ | cyclopropyl | H |
| 219. | o,o'-diCH₃O-p-(CH=CHCN)phenyl | SO₂NH₂ | CH₃ | H |
| 220. | o,o'-diCH₃O-p-(CH=CHCN)phenyl | SO₂NH₂ | CH₃ | CH₃ |
| 221. | o,o'-diCH₃O-p-(CH=CHCN)phenyl | F | cyclopropyl | CH₃ |
| 222. | o,o'-diCH₃O-p-(CH=CHCN)phenyl | F | cyclopropyl | H |
| 223. | o,o'-diCH₃O-p-(CH=CHCN)phenyl | F | CH₃ | H |
| 224. | 4-cyclopropylnaphth-1-yl | SO₂NH₂ | CH₃ | CH₃ |
| 225. | 4-cyclopropylnaphth-1-yl | SO₂NH₂ | cyclopropyl | CH₃ |
| 226. | 4-cyclopropylnaphth-1-yl | SO₂NH₂ | cyclopropyl | H |
| 227. | 4-cyclopropylnaphth-1-yl | SO₂NH₂ | CH₃ | H |
| 228. | 4-cyclopropylnaphth-1-yl | F | CH₃ | CH₃ |
| 229. | 4-cyclopropylnaphth-1-yl | F | cyclopropyl | CH₃ |
| 230. | 4-cyclopropylnaphth-1-yl | F | cyclopropyl | H |
| 231. | 4-cyclopropylnaphth-1-yl | F | CH₃ | H |
| 232. | o,o'-di-CH₃O-p-CN-phenyl | SO₂NH₂ | CH₃ | CH₃ |
| 233. | o,o'-di-CH₃O-p-CN-phenyl | SO₂NHCH₃ | CH₃ | CH₃ |
| 234. | o,o'-di-CH₃O-p-CN-phenyl | SO₂NH₂ | cyclopropyl | CH₃ |
| 235. | o,o'-di-CH₃O-p-CN-phenyl | SO₂NH₂ | cyclopropyl | H |
| 236. | o,o'-di-CH₃O-p-CN-phenyl | SO₂NH₂ | CH₃ | H |
| 237. | o,o'-di-CH₃O-p-CN-phenyl | F | CH₃ | CH₃ |
| 238. | o,o'-di-CH₃O-p-CN-phenyl | F | cyclopropyl | CH₃ |
| 239. | o,o'-di-CH₃O-p-CN-phenyl | F | cyclopropyl | H |
| 240. | o,o'-di-CH₃O-p-CN-phenyl | F | CH₃ | H |
| 241. | o,o'-di-CH₃-p-CN-phenyl | SO₂NH₂ | CH₃ | CH₃ |
| 242. | o,o'-di-CH₃-p-CN-phenyl | SO₂NH₂ | cyclopropyl | CH₃ |
| 243. | o,o'-di-CH₃-p-CN-phenyl | SO₂NH₂ | cyclopropyl | H |
| 244. | o,o'-di-CH₃-p-CN-phenyl | SO₂NH₂ | CH₃ | H |
| 245. | o,o'-di-CH₃-p-CN-phenyl | F | CH₃ | CH₃ |
| 246. | o,o'-di-CH₃-p-CN-phenyl | F | cyclopropyl | CH₃ |

TABLE 1-continued

Contemplated Compounds of Formula IA-1

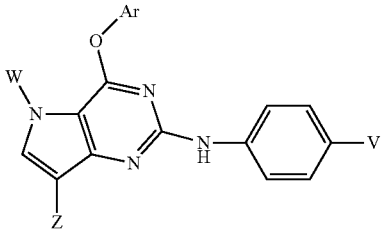

IA-1

| | Ar | V | W | Z |
|---|---|---|---|---|
| 247. | o,o'-di-CH$_3$-p-CN-phenyl | F | cyclopropyl | H |
| 248. | o,o'-di-CH$_3$-p-CN-phenyl | F | CH$_3$ | H |
| 249. | o,o'-diCH$_3$O-p-(CH=CHCN)phenyl | SO$_2$NH$_2$ | CH$_3$ | F |
| 250. | o,o'-diCH$_3$O-p-(CH=CHCN)phenyl | SO$_2$NH$_2$ | cyclopropyl | F |
| 251. | o,o'-diCH$_3$O-p-(CH=CHCN)phenyl | F | cyclopropyl | F |
| 252. | o,o'-diCH$_3$O-p-(CH=CHCN)phenyl | F | CH$_3$ | F |
| 253. | 4-cyclopropylnaphth-1-yl | SO$_2$NH$_2$ | CH$_3$ | F |
| 254. | 4-cyclopropylnaphth-1-yl | SO$_2$NH$_2$ | cyclopropyl | F |
| 255. | 4-cyclopropylnaphth-1-yl | F | CH$_3$ | F |
| 256. | 4-cyclopropylnaphth-1-yl | F | cyclopropyl | F |
| 257. | o,o'-di-CH$_3$O-p-CN-phenyl | SO$_2$NH$_2$ | CH$_3$ | F |
| 258. | o,o'-di-CH$_3$O-p-CN-phenyl | SO$_2$NH$_2$ | cyclopropyl | F |
| 259. | o,o'-di-CH$_3$O-p-CN-phenyl | F | CH$_3$ | F |
| 260. | o,o'-di-CH$_3$O-p-CN-phenyl | F | cyclopropyl | F |
| 261. | o,o'-di-CH$_3$-p-CN-phenyl | SO$_2$NH$_2$ | CH$_3$ | F |
| 262. | o,o'-di-CH$_3$-p-CN-phenyl | SO$_2$NH$_2$ | cyclopropyl | F |
| 263. | o,o'-di-CH$_3$-p-CN-phenyl | F | CH$_3$ | F |
| 264. | o,o'-di-CH$_3$-p-CN-phenyl | F | cyclopropyl | F |
| 265. | 4-cyclopropyl phenyl | CN | CH$_3$ | CH$_3$ |
| 266. | 2,4,6-trimethyl phenyl | CN | cyclopropyl | CH$_3$ |
| 267. | 2,4,6-trimethyl phenyl | CN | cyclopropyl | H |
| 268. | 2,4,6-trimethyl phenyl | CN | CH$_3$ | H |
| 269. | 2,4,6-trimethyl phenyl | CH=CHCN | CH$_3$ | CH$_3$ |
| 270. | 2,4,6-trimethyl phenyl | CH=CHCN | cyclopropyl | CH$_3$ |
| 271. | 2,4,6-trimethyl phenyl | CH=CHCN | cyclopropyl | H |
| 272. | 2,4,6-trimethyl phenyl | CH=CHCN | CH$_3$ | H |
| 273. | 2,4,6-trimethyl phenyl | CN | CH$_3$ | F |
| 274. | 2,4,6-trimethyl phenyl | CN | cyclopropyl | F |
| 275. | 2,4,6-trimethyl phenyl | CH=CHCN | CH$_3$ | F |
| 276. | 2,4,6-trimethyl phenyl | CH=CHCN | cyclopropyl | F |
| 277. | 2,4,6-trimethyl phenyl | SO$_2$NH$_2$ | CH$_3$ | CH$_3$ |
| 278. | 2,4,6-trimethyl phenyl | SO$_2$NH$_2$ | cyclopropyl | CH$_3$ |
| 279. | 2,4,6-trimethyl phenyl | SO$_2$NH$_2$ | cyclopropyl | H |
| 280. | 2,4,6-trimethyl phenyl | SO$_2$NH$_2$ | CH$_3$ | H |
| 281. | 2,4,6-trimethyl phenyl | F | CH$_3$ | CH$_3$ |
| 282. | 2,4,6-trimethyl phenyl | F | cyclopropyl | CH$_3$ |
| 283. | 2,4,6-trimethyl phenyl | F | cyclopropyl | H |
| 284. | 4-cyclopropyl phenyl | F | CH$_3$ | H |
| 285. | 4-cyclopropyl phenyl | SO$_2$NH$_2$ | CH$_3$ | F |
| 286. | 4-cyclopropyl phenyl | SO$_2$NH$_2$ | cyclopropyl | F |
| 287. | 4-cyclopropyl phenyl | F | CH$_3$ | F |
| 288. | 4-cyclopropyl phenyl | F | cyclopropyl | F |
| 289. | 2,4,6-trimethyl phenyl | CN | CH$_3$ | CH$_3$ |
| 290. | o,o'-dimethyl-p-cyclopropyl phenyl | CN | cyclopropyl | CH$_3$ |
| 291. | o,o'-dimethyl-p-cyclopropyl phenyl | CN | cyclopropyl | H |
| 292. | o,o'-dimethyl-p-cyclopropyl phenyl | CN | CH$_3$ | H |
| 293. | o,o'-dimethyl-p-cyclopropyl phenyl | CH=CHCN | CH$_3$ | CH$_3$ |
| 294. | o,o'-dimethyl-p-cyclopropyl phenyl | CH=CHCN | cyclopropyl | CH$_3$ |
| 295. | o,o'-dimethyl-p-cyclopropyl phenyl | CH=CHCN | cyclopropyl | H |
| 296. | o,o'-dimethyl-p-cyclopropyl phenyl | CH=CHCN | CH$_3$ | H |
| 297. | o,o'-dimethyl-p-cyclopropyl phenyl | CN | CH$_3$ | F |
| 298. | o,o'-dimethyl-p-cyclopropyl phenyl | CN | cyclopropyl | F |
| 299. | o,o'-dimethyl-p-cyclopropyl phenyl | CH=CHCN | CH$_3$ | F |
| 300. | o,o'-dimethyl-p-cyclopropyl phenyl | CH=CHCN | cyclopropyl | F |
| 301. | o,o'-dimethyl-p-cyclopropyl phenyl | SO$_2$NH$_2$ | CH$_3$ | CH$_3$ |
| 302. | o,o'-dimethyl-p-cyclopropyl phenyl | SO$_2$NH$_2$ | cyclopropyl | CH$_3$ |
| 303. | o,o'-dimethyl-p-cyclopropyl phenyl | SO$_2$NH$_2$ | cyclopropyl | H |
| 304. | o,o'-dimethyl-p-cyclopropyl phenyl | SO$_2$NH$_2$ | CH$_3$ | H |
| 305. | o,o'-dimethyl-p-cyclopropyl phenyl | F | CH$_3$ | CH$_3$ |
| 306. | o,o'-dimethyl-p-cyclopropyl phenyl | F | cyclopropyl | CH$_3$ |
| 307. | o,o'-dimethyl-p-cyclopropyl phenyl | F | cyclopropyl | H |
| 308. | 2,4,6-trimethyl phenyl | F | CH$_3$ | H |
| 309. | 2,4,6-trimethyl phenyl | SO$_2$NH$_2$ | CH$_3$ | F |

TABLE 1-continued

Contemplated Compounds of Formula IA-1

IA-1

| | Ar | V | W | Z |
|---|---|---|---|---|
| 310. | 2,4,6-trimethyl phenyl | $SO_2NH_2$ | cyclopropyl | F |
| 311. | 2,4,6-trimethyl phenyl | F | $CH_3$ | F |
| 312. | 2,4,6-trimethyl phenyl | F | cyclopropyl | F |
| 313. | o,o'-di-$CH_3$-p-acetyl-phenyl | CN | $CH_3$ | H |
| 314. | o,o'-di-$CH_3$-p-acetyl-phenyl | CN | H | H |
| 315. | o,o'-di-$CH_3$-p-acetyl-phenyl | CN | $CH_3$ | Cl |
| 316. | o,o'-di-$CH_3$-p-acetyl-phenyl | CN | H | Cl |

TABLE 2

Contemplated Compounds of Formula IA-2

| | Ar | V | W | Z |
|---|---|---|---|---|
| 1. | o,o'-di$CH_3$O-p-(CH=CHCN)-phenyl | CN | F | $CH_3$ |
| 2. | o,o'-di$CH_3$O-p-(CH=CHCN)-phenyl | CN | benzyl | $CH_3$ |
| 3. | o,o'--di$CH_3$O-p-(CH=CHCN)-phenyl | CN | benzyl | H |
| 4. | o,o'--di$CH_3$O-p-(CH=CHCN)-phenyl | CN | F | H |
| 5. | o,o'-di$CH_3$O-p-(CH=CHCN)-phenyl | CH=CHCN | Cl | $CH_3$ |
| 6. | o,o'-di$CH_3$O-p-(CH=CHCN)-phenyl | CH=CHCN | benzyl | $CH_3$ |
| 7. | o,o'-di$CH_3$O-p-(CH=CHCN)-phenyl | CH=CHCN | benzyl | H |
| 8. | o,o'-di$CH_3$O-p-(CH=CHCN)-phenyl | CH=CHCN | Cl | H |
| 9. | 4-cyclopropylnaphth-1-yl | C≡$CCH_3$ | allyl | ethyl |
| 10. | 4-cyclopropylnaphth-1-yl | CN | allyl | ethyl |
| 11. | 4-cyclopropylnaphth-1-yl | CN | benzyl | H |
| 12. | 4-cyclopropylnaphth-1-yl | CN | benzyl | H |
| 13. | 4-cyclopropylnaphth-1-yl | C≡$CCH_3$ | allyl | ethyl |
| 14. | 4-cyclopropylnaphth-1-yl | CH=CHCN | allyl | ethyl |
| 15. | 4-cyclopropylnaphth-1-yl | CH=CHCN | 3-MeO-benzyl | H |
| 16. | 4-cyclopropylnaphth-1-yl | CH=CHCN | benzyl | H |
| 17. | o,o'-di-$CH_3$O-p-CN-phenyl | $SO_2NHCH_3$ | CH=CHCN | $CH_3$ |
| 18. | o,o'-di-$CH_3$O-p-CN-phenyl | CN | CH=CHCN | $CH_3$ |
| 19. | o,o'-di-$CH_3$O-p-CN-phenyl | CN | 3-Me-benzyl | H |
| 20. | o,o'-di-$CH_3$O-p-CN-phenyl | CN | benzyl | H |
| 21. | o,o'-di-$CH_3$O-p-CN-phenyl | CH=CHCN | CH=CHCN | $CH_3$ |
| 22. | o,o'-di-$CH_3$O-p-CN-phenyl | CH=CHCN | $CH_2CH_2CN$ | $CH_3$ |
| 23. | o,o'-di-$CH_3$O-p-CN-phenyl | CH=CHCN | $CH_2CH_2CN$ | H |
| 24. | o,o'-di-$CH_3$O-p-CN-phenyl | CH=CHCN | benzyl | H |
| 25. | o,o'-di-$CH_3$O-p-(CH=CHCN)-phenyl | CN | $CH_3$ | H |
| 26. | o,o'-di-$CH_3$O-p-(CH=CHCN)-phenyl | CN | $CH_3$ | benzyl |
| 27. | o,o'-di-$CH_3$O-p-(CH=CHCN)-phenyl | CN | H | benzyl |
| 28. | o,o'-di-$CH_3$O-p-(CH=CHCN)-phenyl | CN | H | H |
| 29. | o,o'-di-$CH_3$O-p-(CH=CHCN)-phenyl | CH=CHCN | $CH_3$ | H |
| 30. | o,o'-di-$CH_3$O-p-(CH=CHCN)-phenyl | CH=CHCN | $CH_3$ | benzyl |
| 31. | o,o'-di-$CH_3$O-p-(CH=CHCN)-phenyl | CH=CHCN | H | benzyl |
| 32. | o,o'-di-$CH_3$O-p-(CH=CHCN)-phenyl | CH=CHCN | H | H |
| 33. | 4-cyclopropylnaphth-1-yl | CN | $CH_3$ | H |
| 34. | 4-cyclopropylnaphth-1-yl | CN | $CH_3$ | benzyl |
| 35. | 4-cyclopropylnaphth-1-yl | CN | H | benzyl |

TABLE 2-continued

Contemplated Compounds of Formula IA-2

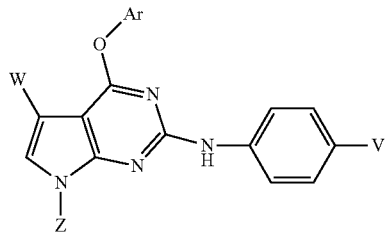

| | Ar | V | W | Z |
|---|---|---|---|---|
| 36. | 4-cyclopropylnaphth-1-yl | CN | H | H |
| 37. | 4-cyclopropylnaphth-1-yl | CH=CHCN | CH₃ | H |
| 38. | 4-cyclopropylnaphth-1-yl | CH=CHCN | CH₃ | benzyl |
| 39. | 4-cyclopropylnaphth-1-yl | CH=CHCN | H | benzyl |
| 40. | 4-cyclopropylnaphth-1-yl | CH=CHCN | H | H |
| 41. | o,o'-di-CH₃O-p-CN-phenyl | CN | CH₃ | H |
| 42. | o,o'-di-CH₃O-p-CN-phenyl | CN | CH₃ | benzyl |
| 43. | o,o'-di-CH₃O-p-CN-phenyl | CN | H | benzyl |
| 44. | o,o'-di-CH₃O-p-CN-phenyl | CN | H | H |
| 45. | o,o'-di-CH₃O-p-CN-phenyl | CH=CHCN | CH₃ | H |
| 46. | o,o'-di-CH₃O-p-CN-phenyl | CH=CHCN | CH₃ | benzyl |
| 47. | o,o'-di-CH₃O-p-CN-phenyl | CH=CHCN | H | benzyl |
| 48. | o,o'-di-CH₃O-p-CN-phenyl | CH=CHCN | H | H |
| 49. | o,o'-di-CH₃-p-CN-phenyl | CN | CH₃ | H |
| 50. | o,o'-di-CH₃-p-CN-phenyl | CN | CH₃ | benzyl |
| 51. | o,o'-di-CH₃-p-CN-phenyl | CN | H | benzyl |
| 52. | o,o'-di-CH₃-p-CN-phenyl | CN | H | H |
| 53. | o,o'-di-CH₃-p-CN-phenyl | CH=CHCN | CH₃ | H |
| 54. | o,o'-di-CH₃-p-CN-phenyl | CH=CHCN | CH₃ | benzyl |
| 55. | o,o'-di-CH₃-p-CN-phenyl | CH=CHCN | H | benzyl |
| 56. | o,o'-di-CH₃-p-CN-phenyl | CH=CHCN | H | H |
| 57. | o,o'-di-CH₃O-p-(CH=CHCN)-phenyl | CN | F | H |
| 58. | o,o'-di-CH₃O-p-(CH=CHCN)-phenyl | CN | F | benzyl |
| 59. | o,o'-di-CH₃O-p-(CH=CHCN)-phenyl | CH=CHCN | F | benzyl |
| 60. | o,o'-di-CH₃O-p-(CH=CHCN)-phenyl | CH=CHCN | F | H |
| 61. | 4-cyclopropylnaphth-1-yl | CN | F | H |
| 62. | 4-cyclopropylnaphth-1-yl | CN | F | benzyl |
| 63. | 4-cyclopropylnaphth-1-yl | CH=CHCN | F | H |
| 64. | 4-cyclopropylnaphth-l-yl | CH=CHCN | F | benzyl |
| 65. | o,o'-di-CH₃O-p-CN-phenyl | CN | F | H |
| 66. | o,o'-di-CH₃O-p-CN-phenyl | CN | F | benzyl |
| 67. | o,o'-di-CH₃O-p-CN-phenyl | CH=CHCN | F | H |
| 68. | o,o'-di-CH₃O-p-CN-phenyl | CH=CHCN | F | benzyl |
| 69. | o,o'-di-CH₃-p-CN-phenyl | CN | F | H |
| 70. | o,o'-di-CH₃-p-CN-phenyl | CN | F | benzyl |
| 71. | o,o'-di-CH₃-p-CN-phenyl | CH=CHCN | F | H |
| 72. | o,o'-di-CH₃-p-CN-phenyl | CH=CHCN | F | benzyl |
| 73. | o,o'-diCH₃O-p-(CH=CHCN)-phenyl | SO₂NH₂ | CH₃ | H |
| 74. | o,o'-diCH₃O-p-(CH=CHCN)-phenyl | SO₂NH₂ | CH₃ | benzyl |
| 75. | o,o'-diCH₃O-p-(CH=CHCN)-phenyl | SO₂NH₂ | H | benzyl |
| 76. | o,o'-diCH₃O-p-(CH=CHCN)-phenyl | SO₂NH₂ | H | H |
| 77. | o,o'-diCH₃O-p-(CH=CHCN)-phenyl | SO₂NH₂ | CH₃ | H |
| 78. | o,o'-diCH₃O-p-(CH=CHCN)-phenyl | F | CH₃ | benzyl |
| 79. | o,o'-diCH₃O-p-(CH=CHCN)-phenyl | F | H | benzyl |
| 80. | o,o'-diCH₃O-p-(CH=CHCN)-phenyl | F | H | H |
| 81. | 4-cyclopropylnaphth-1-yl | SO₂NH₂ | CH₃ | H |
| 82. | 4-cyclopropylnaphth-1-yl | SO₂NH₂ | CH₃ | benzyl |
| 83. | 4-cyclopropylnaphth-1-yl | SO₂NH₂ | H | benzyl |
| 84. | 4-cyclopropylnaphth-1-yl | SO₂NH₂ | H | H |
| 85. | 4-cyclopropylnaphth-1-yl | F | CH₃ | H |
| 86. | 4-cyclopropylnaphth-1-yl | F | CH₃ | benzyl |
| 87. | 4-cyclopropylnaphth-1-yl | F | H | benzyl |
| 88. | 4-cyclopropylnaphth-1-yl | F | H | H |
| 89. | o,o'-di-CH₃O-p-CN-phenyl | SO₂NH₂ | CH₃ | H |
| 90. | o,o'-di-CH₃O-p-CN-phenyl | SO₂NH₂ | CH₃ | benzyl |
| 91. | o,o'-di-CH₃O-p-CN-phenyl | SO₂NH₂ | H | benzyl |
| 92. | o,o'-di-CH₃O-p-CN-phenyl | SO₂NH₂ | H | H |
| 93. | o,o'-di-CH₃O-p-CN-phenyl | F | CH₃ | H |
| 94. | o,o'-di-CH₃O-p-CN-phenyl | F | CH₃ | benzyl |
| 95. | o,o'-di-CH₃O-p-CN-phenyl | F | H | benzyl |
| 96. | o,o'-di-CH₃O-p-CN-phenyl | F | H | H |
| 97. | o,o'-di-CH₃-p-CN-phenyl | SO₂NH₂ | CH₃ | H |
| 98. | o,o'-di-CH₃-p-CN-phenyl | SO₂NH₂ | CH₃ | benzyl |
| 99. | o,o'-di-CH₃-p-CN-phenyl | SO₂NH₂ | H | benzyl |

TABLE 2-continued

Contemplated Compounds of Formula IA-2

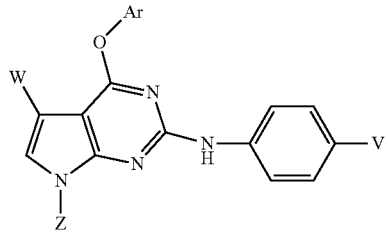

| | Ar | V | W | Z |
|---|---|---|---|---|
| 100. | o,o'-di-CH₃-p-CN-phenyl | SO₂NH₂ | H | H |
| 101. | o,o'-di-CH₃-p-CN-phenyl | F | CH₃ | H |
| 102. | o,o'-di-CH₃-p-CN-phenyl | F | CH₃ | benzyl |
| 103. | o,o'-di-CH₃-p-CN-phenyl | F | H | benzyl |
| 104. | o,o'-di-CH₃-p-CN-phenyl | F | H | H |
| 105. | o,o'-diCH₃O-p-(CH=CHCN)-phenyl | SO₂NH₂ | F | H |
| 106. | o,o'-diCH₃O-p-(CH=CHCN)-phenyl | SO₂NH₂ | F | benzyl |
| 107. | o,o'-diCH₃O-p-(CH=CHCN)-phenyl | F | F | benzyl |
| 108. | o,o'-diCH₃O-p-(CH=CHCN)-phenyl | F | F | H |
| 109. | 4-cyclopropylnaphth-1-yl | SO₂NH₂ | F | H |
| 110. | 4-cyclopropylnaphth-1-yl | SO₂NH₂ | F | benzyl |
| 111. | 4-cyclopropylnaphth-1-yl | F | F | H |
| 112. | 4-cyclopropylnaphth-1-yl | F | F | benzyl |
| 113. | o,o'-di-CH₃O-p-CN-phenyl | SO₂NH₂ | F | H |
| 114. | o,o'-di-CH₃O-p-CN-phenyl | SO₂NH₂ | F | benzyl |
| 115. | o,o'-di-CH₃O-p-CN-phenyl | F | F | H |
| 116. | o,o'-di-CH₃O-p-CN-phenyl | F | F | benzyl |
| 117. | o,o'-di-CH₃-p-CN-phenyl | SO₂NH₂ | F | H |
| 118. | o,o'-di-CH₃-p-CN-phenyl | SO₂NH₂ | F | benzyl |
| 119. | o,o'-di-CH₃-p-CN-phenyl | F | F | H |
| 120. | o,o'-di-CH₃-p-CN-phenyl | F | F | benzyl |
| 121. | 4-cyclopropyl phenyl | CN | CH₃ | H |
| 122. | 4-cyclopropyl phenyl | CN | CH₃ | benzyl |
| 123. | 4-cyclopropyl phenyl | CN | H | benzyl |
| 124. | 4-cyclopropyl phenyl | CN | H | H |
| 125. | 2,4,6-trimethyl phenyl | CH=CHCN | CH₃ | H |
| 126. | 2,4,6-trimethyl phenyl | CH=CHCN | CH₃ | benzyl |
| 127. | 2,4,6-trimethyl phenyl | CH=CHCN | H | benzyl |
| 128. | 2,4,6-trimethyl phenyl | CH=CHCN | H | H |
| 129. | 2,4,6-trimethyl phenyl | CN | F | H |
| 130. | 2,4,6-trimethyl phenyl | CN | F | benzyl |
| 131. | 2,4,6-trimethyl phenyl | CH=CHCN | F | H |
| 132. | 2,4,6-trimethyl phenyl | CH=CHCN | F | benzyl |
| 133. | 2,4,6-trimethyl phenyl | SO₂NH₂ | CH₃ | H |
| 134. | 2,4,6-trimethyl phenyl | SO₂NH₂ | CH₃ | benzyl |
| 135. | 2,4,6-trimethyl phenyl | SO₂NH₂ | H | benzyl |
| 136. | 2,4,6-trimethyl phenyl | SO₂NH₂ | H | H |
| 137. | 2,4,6-trimethyl phenyl | F | CH₃ | H |
| 138. | 2,4,6-trimethyl phenyl | F | CH₃ | benzyl |
| 139. | 2,4,6-trimethyl phenyl | F | H | benzyl |
| 140. | 4-cyclopropyl phenyl | F | H | H |
| 141. | 4-cyclopropyl phenyl | SO₂NH₂ | F | H |
| 142. | 4-cyclopropyl phenyl | SO₂NH₂ | F | benzyl |
| 143. | 4-cyclopropyl phenyl | F | F | H |
| 144. | 4-cyclopropyl phenyl | F | F | benzyl |
| 145. | o,o'-dimethyl-p-cyclopropyl phenyl | CN | CH₃ | H |
| 146. | o,o'-dimethyl-p-cyclopropyl phenyl | CN | CH₃ | benzyl |
| 147. | o,o'-dimethyl-p-cyclopropyl phenyl | CN | H | benzyl |
| 148. | o,o'-dimethyl-p-cyclopropyl phenyl | CN | H | H |
| 149. | o,o'-dimethyl-p-cyclopropyl phenyl | CH=CHCN | CH₃ | H |
| 150. | o,o'-dimethyl-p-cyclopropyl phenyl | CH=CHCN | CH₃ | benzyl |
| 151. | o,o'-dimethyl-p-cyclopropyl phenyl | CH=CHCN | H | benzyl |
| 152. | o,o'-dimethyl-p-cyclopropyl phenyl | CH=CHCN | H | H |
| 153. | o,o'-dimethyl-p-cyclopropyl phenyl | CN | F | H |
| 154. | o,o'-dimethyl-p-cyclopropyl phenyl | CN | F | benzyl |
| 155. | o,o'-dimethyl-p-cyclopropyl phenyl | CH=CHCN | F | H |
| 156. | o,o'-dimethyl-p-cyclopropyl phenyl | CH=CHCN | F | benzyl |
| 157. | o,o'-dimethyl-p-cyclopropyl phenyl | SO₂NH₂ | CH₃ | H |
| 158. | o,o'-dimethyl-p-cyclopropyl phenyl | SO₂NH₂ | CH₃ | benzyl |
| 159. | o,o'-dimethyl-p-cyclopropyl phenyl | SO₂NH₂ | H | benzyl |
| 160. | o,o'-dimethyl-p-cyclopropyl phenyl | SO₂NH₂ | H | H |
| 161. | o,o'-dimethyl-p-cyclopropyl phenyl | F | CH₃ | H |
| 162. | o,o'-dimethyl-p-cyclopropyl phenyl | F | CH₃ | benzyl |
| 163. | o,o'-dimethyl-p-cyclopropyl phenyl | F | H | benzyl |

TABLE 2-continued

Contemplated Compounds of Formula IA-2

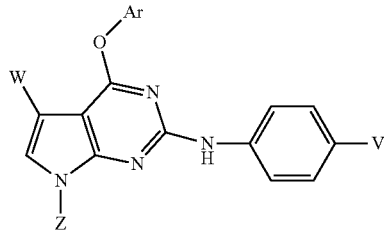

| | Ar | V | W | Z |
|---|---|---|---|---|
| 164. | o,o'-dimethyl-p-cyclopropyl phenyl | F | H | H |
| 165. | o,o'-dimethyl-p-cyclopropyl phenyl | $SO_2NH_2$ | F | H |
| 166. | o,o'-dimethyl-p-cyclopropyl phenyl | $SO_2NH_2$ | F | benzyl |
| 167. | 2-methyl-4-cyclopropyl phenyl | F | F | H |
| 168. | 2-methyl-4-cyclopropyl phenyl | F | F | benzyl |
| 169. | o,o'-diCH$_3$O-p-(CH=CHCN)-phenyl | CN | $CH_3$ | $CH_3$ |
| 170. | o,o'-diCH$_3$O-p-(CH=CHCN)-phenyl | CN | $CH_3$ | cyclopropyl |
| 171. | o,o'-diCH$_3$O-p-(CH=CHCN)-phenyl | CN | H | cyclopropyl |
| 172. | o,o'-diCH$_3$O-p-(CH=CHCN)-phenyl | CN | H | $CH_3$ |
| 173. | o,o'-diCH$_3$O-p-(CH=CHCN)-phenyl | CH=CHCN | $CH_3$ | $CH_3$ |
| 174. | o,o'-diCH$_3$O-p-(CH=CHCN)-phenyl | CH=CHCN | $CH_3$ | cyclopropyl |
| 175. | o,o'-diCH$_3$O-p-(CH=CHCN)-phenyl | CH=CHCN | H | cyclopropyl |
| 176. | o,o'-diCH$_3$O-p-(CH=CHCN)-phenyl | CH=CHCN | H | $CH_3$ |
| 177. | 4-cyclopropylnaphth-1-yl | CN | $CH_3$ | $CH_3$ |
| 178. | 4-cyclopropylnaphth-1-yl | CN | $CH_3$ | cyclopropyl |
| 179. | 4-cyclopropylnaphth-1-yl | CN | H | cyclopropyl |
| 180. | 4-cyclopropylnaphth-1-yl | CN | H | $CH_3$ |
| 181. | 4-cyclopropylnaphth-1-yl | CH=CHCN | $CH_3$ | $CH_3$ |
| 182. | 4-cyclopropylnaphth-1-yl | CH=CHCN | $CH_3$ | cyclopropyl |
| 183. | 4-cyclopropylnaphth-1-yl | CH=CHCN | H | cyclopropyl |
| 184. | 4-cyclopropylnaphth-1-yl | CH=CHCN | H | $CH_3$ |
| 185. | o,o'-di-CH$_3$O-p-CN-phenyl | CN | $CH_3$ | $CH_3$ |
| 186. | o,o'-di-CH$_3$O-p-CN-phenyl | CN | $CH_3$ | cyclopropyl |
| 187. | o,o'-di-CH$_3$O-p-CN-phenyl | CN | H | cyclopropyl |
| 188. | o,o'-di-CH$_3$O-p-CN-phenyl | CN | H | $CH_3$ |
| 189. | o,o'-di-CH$_3$O-p-CN-phenyl | CH=CHCN | $CH_3$ | $CH_3$ |
| 190. | o,o'-di-CH$_3$O-p-CN-phenyl | CH=CHCN | $CH_3$ | cyclopropyl |
| 191. | o,o'-di-CH$_3$O-p-CN-phenyl | CH=CHCN | H | cyclopropyl |
| 192. | o,o'-di-CH$_3$O-p-CN-phenyl | CH=CHCN | H | $CH_3$ |
| 193. | o,o'-di-CH$_3$-p-CN-phenyl | CN | $CH_3$ | $CH_3$ |
| 194. | o,o'-di-CH$_3$-p-CN-phenyl | CN | $CH_3$ | cyclopropyl |
| 195. | o,o'-di-CH$_3$-p-CN-phenyl | CN | H | cyclopropyl |
| 196. | o,o'-di-CH$_3$-p-CN-phenyl | CN | H | $CH_3$ |
| 197. | o,o'-di-CH$_3$-p-CN-phenyl | CH=CHCN | $CH_3$ | $CH_3$ |
| 198. | o,o'-di-CH$_3$-p-CN-phenyl | CH=CHCN | $CH_3$ | cyclopropyl |
| 199. | o,o'-di-CH$_3$-p-CN-phenyl | CH=CHCN | H | cyclopropyl |
| 200. | o,o'-di-CH$_3$-p-CN-phenyl | CH=CHCN | H | $CH_3$ |
| 201. | o,o'-diCH$_3$O-p-(CH=CHCN)-phenyl | CN | F | $CH_3$ |
| 202. | o,o'-diCH$_3$O-p-(CH=CHCN)-phenyl | CN | F | cyclopropyl |
| 203. | o,o'-diCH$_3$O-p-(CH=CHCN)-phenyl | CH=CHCN | F | cyclopropyl |
| 204. | o,o'-diCH$_3$O-p-(CH=CHCN)-phenyl | CH=CHCN | F | $CH_3$ |
| 205. | 4-cyclopropylnaphth-1-yl | CN | F | $CH_3$ |
| 206. | 4-cyclopropylnaphth-1-yl | CN | F | cyclopropyl |
| 207. | 4-cyclopropylnaphth-1-yl | CH=CHCN | F | $CH_3$ |
| 208. | 4-cyclopropylnaphth-1-yl | CH=CHCN | F | cyclopropyl |
| 209. | o,o'-di-CH$_3$O-p-CN-phenyl | CN | F | $CH_3$ |
| 210. | o,o'-di-CH$_3$O-p-CN-phenyl | CN | F | cyclopropyl |
| 211. | o,o'-di-CH$_3$O-p-CN-phenyl | CH=CHCN | F | $CH_3$ |
| 212. | o,o'-di-CH$_3$O-p-CN-phenyl | CH=CHCN | F | cyclopropyl |
| 213. | o,o'-di-CH$_3$-p-CN-phenyl | CN | F | $CH_3$ |
| 214. | o,o'-di-CH$_3$-p-CN-phenyl | CN | F | cyclopropyl |
| 215. | o,o'-di-CH$_3$-p-CN-phenyl | CH=CHCN | F | $CH_3$ |
| 216. | o,o'-di-CH$_3$-p-CN-phenyl | CH=CHCN | F | cyclopropyl |
| 217. | o,o'-diCH$_3$O-p-(CH=CHCN)-phenyl | $SO_2NH_2$ | $CH_3$ | $CH_3$ |
| 218. | o,o'-diCH$_3$O-p-(CH=CHCN)-phenyl | $SO_2NH_2$ | $CH_3$ | cyclopropyl |
| 219. | o,o'-diCH$_3$O-p-(CH=CHCN)-phenyl | $SO_2NH_2$ | H | cyclopropyl |
| 220. | o,o'-diCH$_3$O-p-(CH=CHCN)-phenyl | $SO_2NH_2$ | H | $CH_3$ |
| 221. | o,o'-diCH$_3$O-p-(CH=CHCN)-phenyl | $SO_2NH_2$ | $CH_3$ | $CH_3$ |
| 222. | o,o'-diCH$_3$O-p-(CH=CHCN)-phenyl | F | $CH_3$ | cyclopropyl |
| 223. | o,o'-diCH$_3$O-p-(CH=CHCN)-phenyl | F | H | cyclopropyl |
| 224. | o,o'-diCH$_3$O-p-(CH=CHCN)-phenyl | F | H | $CH_3$ |
| 225. | 4-cyclopropylnaphth-1-yl | $SO_2NH_2$ | $CH_3$ | $CH_3$ |
| 226. | 4-cyclopropylnaphth-1-yl | $SO_2NH_2$ | $CH_3$ | cyclopropyl |
| 227. | 4-cyclopropylnaphth-1-yl | $SO_2NH_2$ | H | cyclopropyl |

TABLE 2-continued

Contemplated Compounds of Formula IA-2

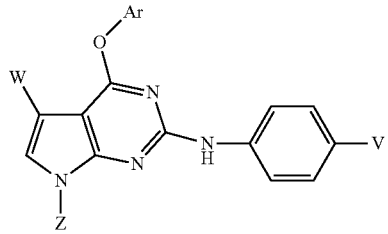

| | Ar | V | W | Z |
|---|---|---|---|---|
| 228. | 4-cyclopropylnaphth-1-yl | $SO_2NH_2$ | H | $CH_3$ |
| 229. | 4-cyclopropylnaphth-1-yl | F | $CH_3$ | $CH_3$ |
| 230. | 4-cyclopropylnaphth-1-yl | F | $CH_3$ | cyclopropyl |
| 231. | 4-cyclopropylnaphth-1-yl | F | H | cyclopropyl |
| 232. | 4-cyclopropylnaphth-1-yl | F | H | $CH_3$ |
| 233. | o,o'-di-$CH_3$O-p-CN-phenyl | $SO_2NH_2$ | $CH_3$ | $CH_3$ |
| 234. | o,o'-di-$CH_3$O-p-CN-phenyl | $SO_2NH_2$ | $CH_3$ | cyclopropyl |
| 235. | o,o'-di-$CH_3$O-p-CN-phenyl | $SO_2NH_2$ | H | cyclopropyl |
| 236. | o,o'-di-$CH_3$O-p-CN-phenyl | $SO_2NH_2$ | H | $CH_3$ |
| 237. | o,o'-di-$CH_3$O-p-CN-phenyl | F | $CH_3$ | $CH_3$ |
| 238. | o,o'-di-$CH_3$O-p-CN-phenyl | F | $CH_3$ | cyclopropyl |
| 239. | o,o'-di-$CH_3$O-p-CN-phenyl | F | H | cyclopropyl |
| 240. | o,o'-di-$CH_3$O-p-CN-phenyl | F | H | $CH_3$ |
| 241. | o,o'-di-$CH_3$-p-CN-phenyl | $SO_2NH_2$ | $CH_3$ | $CH_3$ |
| 242. | o,o'-di-$CH_3$-p-CN-phenyl | $SO_2NH_2$ | $CH_3$ | cyclopropyl |
| 243. | o,o'-di-$CH_3$-p-CN-phenyl | $SO_2NH_2$ | H | cyclopropyl |
| 244. | o,o'-di-$CH_3$-p-CN-phenyl | $SO_2NH_2$ | H | $CH_3$ |
| 245. | o,o'-di-$CH_3$-p-CN-phenyl | F | $CH_3$ | $CH_3$ |
| 246. | o,o'-di-$CH_3$-p-CN-phenyl | F | $CH_3$ | cyclopropyl |
| 247. | o,o'-di-$CH_3$-p-CN-phenyl | F | H | cyclopropyl |
| 248. | o,o'-di-$CH_3$-p-CN-phenyl | F | H | $CH_3$ |
| 249. | o,o'-di$CH_3$O-p-(CH=CHCN)-phenyl | $SO_2NH_2$ | F | $CH_3$ |
| 250. | o,o'-di$CH_3$O-p-(CH=CHCN)-phenyl | $SO_2NH_2$ | F | cyclopropyl |
| 251. | o,o'-di$CH_3$O-p-(CH=CHCN)-phenyl | F | F | cyclopropyl |
| 252. | o,o'-di$CH_3$O-p-(CH=CHCN)-phenyl | F | F | $CH_3$ |
| 253. | 4-cyclopropylnaphth-1-yl | $SO_2NH_2$ | F | $CH_3$ |
| 254. | 4-cyclopropylnaphth-1-yl | $SO_2NH_2$ | F | cyclopropyl |
| 255. | 4-cyclopropylnaphth-1-yl | F | F | $CH_3$ |
| 256. | 4-cyclopropylnaphth-1-yl | F | F | cyclopropyl |
| 257. | o,o'-di-$CH_3$O-p-CN-phenyl | $SO_2NH_2$ | F | $CH_3$ |
| 258. | o,o'-di-$CH_3$O-p-CN-phenyl | $SO_2NH_2$ | F | cyclopropyl |
| 259. | o,o'-di-$CH_3$O-p-CN-phenyl | F | F | $CH_3$ |
| 260. | o,o'-di-$CH_3$O-p-CN-phenyl | F | F | cyclopropyl |
| 261. | o,o'-di-$CH_3$-p-CN-phenyl | $SO_2NH_2$ | F | $CH_3$ |
| 262. | o,o'-di-$CH_3$-p-CN-phenyl | $SO_2NH_2$ | F | cyclopropyl |
| 263. | o,o'-di-$CH_3$-p-CN-phenyl | F | F | $CH_3$ |
| 264. | o,o'-di-$CH_3$-p-CN-phenyl | F | F | cyclopropyl |
| 265. | 4-cyclopropyl phenyl | CN | $CH_3$ | $CH_3$ |
| 266. | 2,4,6-trimethyl phenyl | CN | $CH_3$ | cyclopropyl |
| 267. | 2,4,6-trimethyl phenyl | CN | H | cyclopropyl |
| 268. | 2,4,6-trimethyl phenyl | CN | H | $CH_3$ |
| 269. | 2,4,6-trimethyl phenyl | CH=CHCN | $CH_3$ | $CH_3$ |
| 270. | 2,4,6-trimethyl phenyl | CH=CHCN | $CH_3$ | cyclopropyl |
| 271. | 2,4,6-trimethyl phenyl | CH=CHCN | H | cyclopropyl |
| 272. | 2,4,6-trimethyl phenyl | CH=CHCN | H | $CH_3$ |
| 273. | 2,4,6-trimethyl phenyl | CN | F | $CH_3$ |
| 274. | 2,4,6-trimethyl phenyl | CN | F | cyclopropyl |
| 275. | 2,4,6-trimethyl phenyl | CH=CHCN | F | $CH_3$ |
| 276. | 2,4,6-trimethyl phenyl | CH=CHCN | F | cyclopropyl |
| 277. | 2,4,6-trimethyl phenyl | $SO_2NH_2$ | $CH_3$ | $CH_3$ |
| 278. | 2,4,6-trimethyl phenyl | $SO_2NH_2$ | $CH_3$ | cyclopropyl |
| 279. | 2,4,6-trimethyl phenyl | $SO_2NH_2$ | H | cyclopropyl |
| 280. | 2,4,6-trimethyl phenyl | $SO_2NH_2$ | H | $CH_3$ |
| 281. | 2,4,6-trimethyl phenyl | F | $CH_3$ | $CH_3$ |
| 282. | 2,4,6-trimethyl phenyl | F | $CH_3$ | cyclopropyl |
| 283. | 2,4,6-trimethyl phenyl | F | H | cyclopropyl |
| 284. | 2,4,6-trimethyl phenyl | F | H | $CH_3$ |
| 285. | 2,4,6-trimethyl phenyl | $SO_2NH_2$ | F | $CH_3$ |
| 286. | 4-cyclopropyl phenyl | $SO_2NH_2$ | F | cyclopropyl |
| 287. | 4-cyclopropyl phenyl | F | F | $CH_3$ |
| 288. | 4-cyclopropyl phenyl | F | F | cyclopropyl |
| 289. | o,o'-dimethyl-p-cyclopropyl phenyl | CN | $CH_3$ | $CH_3$ |
| 290. | o,o'-dimethyl-p-cyclopropyl phenyl | CN | $CH_3$ | cyclopropyl |
| 291. | o,o'-dimethyl-p-cyclopropyl phenyl | CN | H | cyclopropyl |

TABLE 2-continued

Contemplated Compounds of Formula IA-2

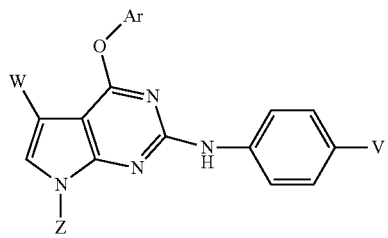

| | Ar | V | W | Z |
|---|---|---|---|---|
| 292. | o,o'-dimethyl-p-cyclopropyl phenyl | CN | H | CH$_3$ |
| 293. | o,o'-dimethyl-p-cyclopropyl phenyl | CH=CHCN | CH$_3$ | CH$_3$ |
| 294. | o,o'-dimethyl-p-cyclopropyl phenyl | CH=CHCN | CH$_3$ | cyclopropyl |
| 295. | o,o'-dimethyl-p-cyclopropyl phenyl | CH=CHCN | H | cyclopropyl |
| 296. | o,o'-dimethyl-p-cyclopropyl phenyl | CH=CHCN | H | CH$_3$ |
| 297. | o,o'-dimethyl-p-cyclopropyl phenyl | CN | F | CH$_3$ |
| 298. | o,o'-dimethyl-p-cyclopropyl phenyl | CN | F | cyclopropyl |
| 299. | o,o'-dimethyl-p-cyclopropyl phenyl | CH=CHCN | F | CH$_3$ |
| 300. | o,o'-dimethyl-p-cyclopropyl phenyl | CH=CHCN | F | cyclopropyl |
| 301. | o,o'-dimethyl-p-cyclopropyl phenyl | SO$_2$NH$_2$ | CH$_3$ | CH$_3$ |
| 302. | o,o'-dimethyl-p-cyclopropyl phenyl | SO$_2$NH$_2$ | CH$_3$ | cyclopropyl |
| 303. | o,o'-dimethyl-p-cyclopropyl phenyl | SO$_2$NH$_2$ | H | cyclopropyl |
| 304. | o,o'-dimethyl-p-cyclopropyl phenyl | SO$_2$NH$_2$ | H | CH$_3$ |
| 305. | o,o'-dimethyl-p-cyclopropyl phenyl | F | CH$_3$ | CH$_3$ |
| 306. | o,o'-dimethyl-p-cyclopropyl phenyl | F | CH$_3$ | cyclopropyl |
| 307. | o,o'-dimethyl-p-cyclopropyl phenyl | F | H | cyclopropyl |
| 308. | o,o'-dimethyl-p-cyclopropyl phenyl | F | H | CH$_3$ |
| 309. | o,o'-dimethyl-p-cyclopropyl phenyl | SO$_2$NH$_2$ | F | CH$_3$ |
| 310. | o,o'-dimethyl-p-cyclopropyl phenyl | SO$_2$NH$_2$ | F | cyclopropyl |
| 311. | o,o'-dimethyl-p-cyclopropyl phenyl | F | F | CH$_3$ |
| 312. | o,o'-dimethyl-p-cyclopropyl phenyl | F | F | cyclopropyl |
| 313. | o,o'-di-CH$_3$-p-acetyl-phenyl | CN | H | H |
| 314. | o,o'-di-CH$_3$-p-acetyl-phenyl | CN | CH$_3$ | H |
| 315. | o,o'-di-CH$_3$-p-acetyl-phenyl | CN | H | Cl |
| 316. | o,o'-di-CH$_3$-p-acetyl-phenyl | CN | CH$_3$ | Cl |

TABLE 3

Contemplated Compounds of Formula IA-3

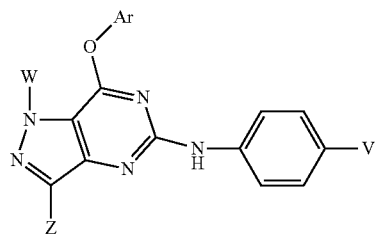

| | Ar | V | W | Z |
|---|---|---|---|---|
| 1. | o,o'-diCH$_3$O-p-(CH=CHCN)-phenyl | CN | benzyl | F |
| 2. | o,o'-diCH$_3$O-p-(CH=CHCN)-phenyl | CN | benzyl | Cl |
| 3. | o,o'-diCH$_3$O-p-(CH=CHCN)-phenyl | CN | allyl | F |
| 4. | o,o'-diCH$_3$O-p-(CH=CHCN)-phenyl | CN | allyl | Cl |
| 5. | o,o'-diCH$_3$O-p-(CH=CHCN)-phenyl | CH=CHCN | benzyl | CH$_3$ |
| 6. | o,o'-diCH$_3$O-p-(CH=CHCN)-phenyl | CH=CHCN | 3-MeO-benzyl | CH$_3$ |
| 7. | o,o'-diCH$_3$O-p-(CH=CHCN)-phenyl | CH=CHCN | 3-Me-benzyl | CH$_3$ |
| 8. | o,o'-diCH$_3$O-p-(CH=CHCN)-phenyl | CH=CHCN | allyl | CH$_3$ |
| 9. | 4-cyclopropylnaphth-1-yl | CN | CH$_2$CH$_3$ | H |
| 10. | 4-cyclopropylnaphth-1-yl | CN | isopropyl | H |

TABLE 3-continued

Contemplated Compounds of Formula IA-3

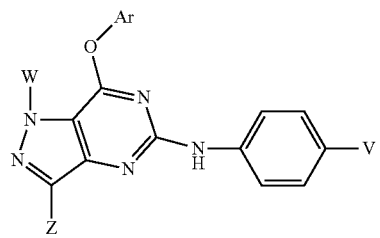

| | Ar | V | W | Z |
|---|---|---|---|---|
| 11. | 4-cyclopropylnaphth-1-yl | CN | CH$_2$CF$_3$ | Br |
| 12. | 4-cyclopropylnaphth-1-yl | CN | CH$_2$CF$_3$ | Cl |
| 13. | 4-cyclopropylnaphth-1-yl | CH=CHCN | CH$_2$CH$_3$ | H |
| 14. | 4-cyclopropylnaphth-1-yl | CH=CHCN | CH$_2$CH$_3$ | Br |
| 15. | 4-cyclopropylnaphth-1-yl | CH=CHCN | CH$_2$CF$_3$ | CH$_3$ |
| 16. | 4-cyclopropylnaphth-1-yl | CH=CHCN | CH$_2$CF$_3$ | H |
| 17. | o,o'-di-CH$_3$O-p-CN-phenyl | CN | benzyl | F |
| 18. | o,o'-di-CH$_3$O-p-CN-phenyl | CN | benzyl | Cl |
| 19. | o,o'-di-CH$_3$O-p-CN-phenyl | CN | allyl | F |
| 20. | o,o'-di-CH$_3$O-p-CN-phenyl | CN | allyl | Cl |
| 21. | o,o'-di-CH$_3$O-p-CN-phenyl | CH=CHCN | benzyl | CH$_3$ |
| 22. | o,o'-di-CH$_3$O-p-CN-phenyl | CH=CHCN | benzyl | Br |
| 23. | o,o'-di-CH$_3$O-p-CN-phenyl | CH=CHCN | allyl | CH$_3$ |
| 24. | o,o'-di-CH$_3$O-p-CN-phenyl | CH=CHCN | allyl | H |
| 25. | o,o'-diCH$_3$O-p-(CH=CHCN)-phenyl | CN | H | F |
| 26. | o,o'-diCH$_3$O-p-(CH=CHCN)-phenyl | CN | benzyl | Cl |

TABLE 3-continued

Contemplated Compounds of Formula IA-3

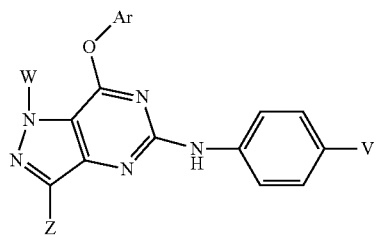

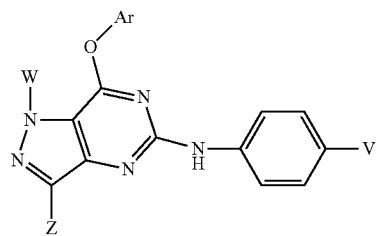

| | Ar | V | W | Z |
|---|---|---|---|---|
| 27. | o,o'-diCH₃O-p-(CH=CHCN)-phenyl | CN | benzyl | H |
| 28. | o,o'-diCH₃O-p-(CH=CHCN)-phenyl | CN | H | H |
| 29. | o,o'-diCH₃O-p-(CH=CHCN)-phenyl | CN | H | CH₃ |
| 30. | o,o'-diCH₃O-p-(CH=CHCN)-phenyl | CH=CHCN | benzyl | CH₃ |
| 31. | o,o'-diCH₃O-p-(CH=CHCN)-phenyl | CH=CHCN | benzyl | H |
| 32. | o,o'-diCH₃O-p-(CH=CHCN)-phenyl | CH=CHCN | H | H |
| 33. | 4-cyclopropylnaphth-1-yl | CN | H | CH₃ |
| 34. | 4-cyclopropylnaphth-1-yl | CN | benzyl | CH₃ |
| 35. | 4-cyclopropylnaphth-1-yl | CN | benzyl | H |
| 36. | 4-cyclopropylnaphth-1-yl | CN | H | H |
| 37. | 4-cyclopropylnaphth-1-yl | CH=CHCN | H | CH₃ |
| 38. | 4-cyclopropylnaphth-1-yl | CH=CHCN | benzyl | CH₃ |
| 39. | 4-cyclopropylnaphth-1-yl | CH=CHCN | benzyl | H |
| 40. | 4-cyclopropylnaphth-1-yl | CH=CHCN | H | H |
| 41. | o,o'-di-CH₃O-p-CN-phenyl | CN | H | CH₃ |
| 42. | o,o'-di-CH₃O-p-CN-phenyl | CN | benzyl | CH₃ |
| 43. | o,o'-di-CH₃O-p-CN-phenyl | CN | benzyl | H |
| 44. | o,o'-di-CH₃O-p-CN-phenyl | CN | H | H |
| 45. | o,o'-di-CH₃O-p-CN-phenyl | CH=CHCN | H | CH₃ |
| 46. | o,o'-di-CH₃O-p-CN-phenyl | CH=CHCN | benzyl | CH₃ |
| 47. | o,o'-di-CH₃O-p-CN-phenyl | CH=CHCN | benzyl | H |
| 48. | o,o'-di-CH₃O-p-CN-phenyl | CH=CHCN | H | H |
| 49. | o,o'-di-CH₃-p-CN-phenyl | CN | H | CH₃ |
| 50. | o,o'-di-CH₃-p-CN-phenyl | CN | benzyl | CH₃ |
| 51. | o,o'-di-CH₃-p-CN-phenyl | CN | benzyl | H |
| 52. | o,o'-di-CH₃-p-CN-phenyl | CN | H | H |
| 53. | o,o'-di-CH₃-p-CN-phenyl | CH=CHCN | H | CH₃ |
| 54. | o,o'-di-CH₃-p-CN-phenyl | CH=CHCN | benzyl | CH₃ |
| 55. | o,o'-di-CH₃-p-CN-phenyl | CH=CHCN | benzyl | H |
| 56. | o,o'-di-CH₃-p-CN-phenyl | CH=CHCN | H | H |
| 57. | o,o'-diCH₃O-p-(CH=CHCN)-phenyl | CN | H | F |
| 58. | o,o'-diCH₃O-p-(CH=CHCN)-phenyl | CN | benzyl | F |
| 59. | o,o'-diCH₃O-p-(CH=CHCN)-phenyl | CH=CHCN | benzyl | F |
| 60. | o,o'-diCH₃O-p-(CH=CHCN)-phenyl | CH=CHCN | H | F |
| 61. | 4-cyclopropylnaphth-1-yl | CN | H | F |
| 62. | 4-cyclopropylnaphth-1-yl | CN | benzyl | F |
| 63. | 4-cyclopropylnaphth-1-yl | CH=CHCN | H | F |
| 64. | 4-cyclopropylnaphth-1-yl | CH=CHCN | benzyl | F |
| 65. | o,o'-di-CH₃O-p-CN-phenyl | CN | H | F |
| 66. | o,o'-di-CH₃O-p-CN-phenyl | CN | benzyl | F |
| 67. | o,o'-di-CH₃O-p-CN-phenyl | CH=CHCN | H | F |
| 68. | o,o'-di-CH₃O-p-CN-phenyl | CH=CHCN | benzyl | F |
| 69. | o,o'-di-CH₃-p-CN-phenyl | CN | H | F |
| 70. | o,o'-di-CH₃-p-CN-phenyl | CN | benzyl | F |
| 71. | o,o'-di-CH₃-p-CN-phenyl | CH=CHCN | H | F |
| 72. | o,o'-di-CH₃-p-CN-phenyl | CH=CHCN | benzyl | F |
| 73. | o,o'-diCH₃O-p-(CH=CHCN)-phenyl | SO₂NH₂ | H | CH₃ |
| 74. | o,o'-diCH₃O-p-(CH=CHCN)-phenyl | SO₂NH₂ | benzyl | CH₃ |
| 75. | o,o'-diCH₃O-p-(CH=CHCN)-phenyl | SO₂NH₂ | benzyl | H |
| 76. | o,o'-diCH₃O-p-(CH=CHCN)-phenyl | SO₂NH₂ | H | H |
| 77. | o,o'-diCH₃O-p-(CH=CHCN)-phenyl | SO₂NH₂ | H | CH₃ |
| 78. | o,o'-diCH₃O-p-(CH=CHCN)-phenyl | F | benzyl | CH₃ |
| 79. | o,o'-diCH₃O-p-(CH=CHCN)-phenyl | F | benzyl | H |
| 80. | o,o'-diCH₃O-p-(CH=CHCN)-phenyl | F | H | H |
| 81. | 4-cyclopropylnaphth-1-yl | SO₂NH₂ | H | CH₃ |
| 82. | 4-cyclopropylnaphth-1-yl | SO₂NH₂ | benzyl | CH₃ |
| 83. | 4-cyclopropylnaphth-1-yl | SO₂NH₂ | benzyl | H |
| 84. | 4-cyclopropylnaphth-1-yl | SO₂NH₂ | H | H |
| 85. | 4-cyclopropylnaphth-1-yl | F | H | CH₃ |
| 86. | 4-cyclopropylnaphth-1-yl | F | benzyl | CH₃ |
| 87. | 4-cyclopropylnaphth-1-yl | F | benzyl | H |
| 88. | 4-cyclopropylnaphth-1-yl | F | H | H |
| 89. | o,o'-di-CH₃O-p-CN-phenyl | SO₂NH₂ | H | CH₃ |
| 90. | o,o'-di-CH₃O-p-CN-phenyl | SO₂NH₂ | benzyl | CH₃ |
| 91. | o,o'-di-CH₃O-p-CN-phenyl | SO₂NH₂ | benzyl | H |
| 92. | o,o'-di-CH₃O-p-CN-phenyl | SO₂NH₂ | H | H |
| 93. | o,o'-di-CH₃O-p-CN-phenyl | F | H | CH₃ |
| 94. | o,o'-di-CH₃O-p-CN-phenyl | F | benzyl | CH₃ |
| 95. | o,o'-di-CH₃O-p-CN-phenyl | F | benzyl | H |
| 96. | o,o'-di-CH₃O-p-CN-phenyl | F | H | H |
| 97. | o,o'-di-CH₃-p-CN-phenyl | SO₂NH₂ | H | CH₃ |
| 98. | o,o'-di-CH₃-p-CN-phenyl | SO₂NH₂ | benzyl | CH₃ |
| 99. | o,o'-di-CH₃-p-CN-phenyl | SO₂NH₂ | benzyl | H |
| 100. | o,o'-di-CH₃-p-CN-phenyl | SO₂NH₂ | H | H |
| 101. | o,o'-di-CH₃-p-CN-phenyl | F | H | CH₃ |
| 102. | o,o'-di-CH₃-p-CN-phenyl | F | benzyl | CH₃ |
| 103. | o,o'-di-CH₃-p-CN-phenyl | F | benzyl | H |
| 104. | o,o'-di-CH₃-p-CN-phenyl | F | H | H |
| 105. | o,o'-diCH₃O-p-(CH=CHCN)-phenyl | SO₂NH₂ | H | F |
| 106. | o,o'-diCH₃O-p-(CH=CHCN)-phenyl | SO₂NH₂ | benzyl | F |
| 107. | o,o'-diCH₃O-p-(CH=CHCN)-phenyl | F | benzyl | F |
| 108. | o,o'-diCH₃O-p-(CH=CHCN)-phenyl | F | H | F |
| 109. | 4-cyclopropylnaphth-1-yl | SO₂NH₂ | H | F |
| 110. | 4-cyclopropylnaphth-1-yl | SO₂NH₂ | benzyl | F |
| 111. | 4-cyclopropylnaphth-1-yl | F | H | F |
| 112. | 4-cyclopropylnaphth-1-yl | F | benzyl | F |
| 113. | o,o'-di-CH₃O-p-CN-phenyl | SO₂NH₂ | H | F |
| 114. | o,o'-di-CH₃O-p-CN-phenyl | SO₂NH₂ | benzyl | F |
| 115. | o,o'-di-CH₃O-p-CN-phenyl | F | H | F |
| 116. | o,o'-di-CH₃O-p-CN-phenyl | F | benzyl | F |
| 117. | o,o'-di-CH₃-p-CN-phenyl | SO₂NH₂ | H | F |
| 118. | o,o'-di-CH₃-p-CN-phenyl | SO₂NH₂ | benzyl | F |
| 119. | o,o'-di-CH₃-p-CN-phenyl | F | H | F |
| 120. | o,o'-di-CH₃-p-CN-phenyl | F | benzyl | F |
| 121. | 2,4,6-trimethyl phenyl | CN | H | CH₃ |
| 122. | 2,4,6-trimethyl phenyl | CN | benzyl | CH₃ |
| 123. | 2,4,6-trimethyl phenyl | CN | benzyl | H |
| 124. | 2,4,6-trimethyl phenyl | CN | H | H |
| 125. | 2,4,6-trimethyl phenyl | CH=CHCN | H | CH₃ |
| 126. | 2,4,6-trimethyl phenyl | CH=CHCN | benzyl | CH₃ |
| 127. | 4-cyclopropyl phenyl | CH=CHCN | benzyl | H |
| 128. | 4-cyclopropyl phenyl | CH=CHCN | H | H |
| 129. | 4-cyclopropyl phenyl | CN | H | F |
| 130. | 4-cyclopropyl phenyl | CN | benzyl | F |
| 131. | 4-cyclopropyl phenyl | CH=CHCN | H | F |
| 132. | 2,4,6-trimethyl phenyl | CH=CHCN | benzyl | F |

TABLE 3-continued

Contemplated Compounds of Formula IA-3

|  | Ar | V | W | Z |
|---|---|---|---|---|
| 133. | 2,4,6-trimethyl phenyl | SO$_2$NH$_2$ | H | CH$_3$ |
| 134. | 2,4,6-trimethyl phenyl | SO$_2$NH$_2$ | benzyl | CH$_3$ |
| 135. | 2,4,6-trimethyl phenyl | SO$_2$NH$_2$ | benzyl | H |
| 136. | 2,4,6-trimethyl phenyl | SO$_2$NH$_2$ | H | H |
| 137. | 2,4,6-trimethyl phenyl | F | H | CH$_3$ |
| 138. | 2,4,6-trimethyl phenyl | F | benzyl | CH$_3$ |
| 139. | 2,4,6-trimethyl phenyl | F | benzyl | H |
| 140. | 2,4,6-trimethyl phenyl | F | H | H |
| 141. | 2,4,6-trimethyl phenyl | SO$_2$NH$_2$ | H | F |
| 142. | 2,4,6-trimethyl phenyl | SO$_2$NH$_2$ | benzyl | F |
| 143. | 2,4,6-trimethyl phenyl | F | H | F |
| 144. | 2,4,6-trimethyl phenyl | F | benzyl | F |
| 145. | 2,4,6-trimethyl phenyl | CN | H | CH$_3$ |
| 146. | 2,4,6-trimethyl phenyl | CN | benzyl | CH$_3$ |
| 147. | 2,4,6-trimethyl phenyl | CN | benzyl | H |
| 148. | 2,4,6-trimethyl phenyl | CN | H | H |
| 149. | 2,4,6-trimethyl phenyl | CH=CHCN | H | CH$_3$ |
| 150. | 2,4,6-trimethyl phenyl | CH=CHCN | benzyl | CH$_3$ |
| 151. | 2,4,6-trimethyl phenyl | CH=CHCN | benzyl | H |
| 152. | 2,4,6-trimethyl phenyl | CH=CHCN | H | H |
| 153. | 2,4,6-trimethyl phenyl | CN | H | F |
| 154. | 2,4,6-trimethyl phenyl | CN | benzyl | F |
| 155. | 2,4,6-trimethyl phenyl | CH=CHCN | H | F |
| 156. | 2,4,6-trimethyl phenyl | CH=CHCN | benzyl | F |
| 157. | o,o'-dimethyl-p-cyclopropyl phenyl | SO$_2$NH$_2$ | H | CH$_3$ |
| 158. | o,o'-dimethyl-p-cyclopropyl phenyl | SO$_2$NH$_2$ | benzyl | CH$_3$ |
| 159. | o,o'-dimethyl-p-cyclopropyl phenyl | SO$_2$NH$_2$ | benzyl | H |
| 160. | o,o'-dimethyl-p-cyclopropyl phenyl | SO$_2$NH$_2$ | H | H |
| 161. | o,o'-dimethyl-p-cyclopropyl phenyl | F | H | CH$_3$ |
| 162. | o,o'-dimethyl-p-cyclopropyl phenyl | F | benzyl | CH$_3$ |
| 163. | o,o'-dimethyl-p-cyclopropyl phenyl | F | benzyl | H |
| 164. | o,o'-dimethyl-p-cyclopropyl phenyl | F | H | H |
| 165. | o,o'-dimethyl-p-cyclopropyl phenyl | SO$_2$NH$_2$ | H | F |
| 166. | o,o'-dimethyl-p-cyclopropyl phenyl | SO$_2$NH$_2$ | benzyl | F |
| 167. | o,o'-dimethyl-p-cyclopropyl phenyl | F | H | F |
| 168. | o,o'-dimethyl-p-cyclopropyl phenyl | F | benzyl | F |
| 169. | o,o'-diCH$_3$O-p-(CH=CHCN)-phenyl | CN | CH$_3$ | CH$_3$ |
| 170. | o,o'-diCH$_3$O-p-(CH=CHCN)-phenyl | CN | cyclopropyl | CH$_3$ |
| 171. | o,o'-diCH$_3$O-p-(CH=CHCN)-phenyl | CN | cyclopropyl | H |
| 172. | o,o'-diCH$_3$O-p-(CH=CHCN)-phenyl | CN | CH$_3$ | H |
| 173. | o,o'-diCH$_3$O-p-(CH=CHCN)-phenyl | CH=CHCN | CH$_3$ | CH$_3$ |
| 174. | o,o'-diCH$_3$O-p-(CH=CHCN)-phenyl | CH=CHCN | cyclopropyl | CH$_3$ |
| 175. | o,o'-diCH$_3$O-p-(CH=CHCN)-phenyl | CH=CHCN | cyclopropyl | H |
| 176. | o,o'-diCH$_3$O-p-(CH=CHCN)-phenyl | CH=CHCN | CH$_3$ | H |
| 177. | 4-cyclopropylnaphth-1-yl | CN | CH$_3$ | CH$_3$ |
| 178. | 4-cyclopropylnaphth-1-yl | CN | cyclopropyl | CH$_3$ |
| 179. | 4-cyclopropylnaphth-1-yl | CN | cyclopropyl | H |
| 180. | 4-cyclopropylnaphth-1-yl | CN | CH$_3$ | H |
| 181. | 4-cyclopropylnaphth-1-yl | CH=CHCN | CH$_3$ | CH$_3$ |
| 182. | 4-cyclopropylnaphth-1-yl | CH=CHCN | cyclopropyl | CH$_3$ |
| 183. | 4-cyclopropylnaphth-1-yl | CH=CHCN | cyclopropyl | H |
| 184. | 4-cyclopropylnaphth-1-yl | CH=CHCN | CH$_3$ | H |
| 185. | o,o'-di-CH$_3$O-p-CN-phenyl | CN | CH$_3$ | CH$_3$ |
| 186. | o,o'-di-CH$_3$O-p-CN-phenyl | CN | cyclopropyl | CH$_3$ |
| 187. | o,o'-di-CH$_3$O-p-CN-phenyl | CN | cyclopropyl | H |
| 188. | o,o'-di-CH$_3$O-p-CN-phenyl | CN | CH$_3$ | H |
| 189. | o,o'-di-CH$_3$O-p-CN-phenyl | CH=CHCN | CH$_3$ | CH$_3$ |
| 190. | o,o'-di-CH$_3$O-p-CN-phenyl | CH=CHCN | cyclopropyl | CH$_3$ |
| 191. | o,o'-di-CH$_3$O-p-CN-phenyl | CH=CHCN | cyclopropyl | H |
| 192. | o,o'-di-CH$_3$O-p-CN-phenyl | CH=CHCN | CH$_3$ | H |
| 193. | o,o'-di-CH$_3$-p-CN-phenyl | CN | CH$_3$ | CH$_3$ |
| 194. | o,o'-di-CH$_3$-p-CN-phenyl | CN | cyclopropyl | CH$_3$ |
| 195. | o,o'-di-CH$_3$-p-CN-phenyl | CN | cyclopropyl | H |
| 196. | o,o'-di-CH$_3$-p-CN-phenyl | CN | CH$_3$ | H |
| 197. | o,o'-di-CH$_3$-p-CN-phenyl | CH=CHCN | CH$_3$ | CH$_3$ |
| 198. | o,o'-di-CH$_3$-p-CN-phenyl | CH=CHCN | cyclopropyl | CH$_3$ |
| 199. | o,o'-di-CH$_3$-p-CN-phenyl | CH=CHCN | cyclopropyl | H |
| 200. | o,o'-di-CH$_3$-p-CN-phenyl | CH=CHCN | CH$_3$ | H |
| 201. | o,o'-diCH$_3$O-p-(CH=CHCN)-phenyl | CN | CH$_3$ | F |
| 202. | o,o'-diCH$_3$O-p-(CH=CHCN)-phenyl | CN | cyclopropyl | F |
| 203. | o,o'-diCH$_3$O-p-(CH=CHCN)-phenyl | CH=CHCN | cyclopropyl | F |
| 204. | o,o'-diCH$_3$O-p-(CH=CHCN)-phenyl | CH=CHCN | CH$_3$ | F |
| 205. | 4-cyclopropylnaphth-1-yl | CN | CH$_3$ | F |
| 206. | 4-cyclopropylnaphth-1-yl | CN | cyclopropyl | F |
| 207. | 4-cyclopropylnaphth-1-yl | CH=CHCN | CH$_3$ | F |
| 208. | 4-cyclopropylnaphth-1-yl | CH=CHCN | cyclopropyl | F |
| 209. | o,o'-di-CH$_3$O-p-CN-phenyl | CN | CH$_3$ | F |
| 210. | o,o'-di-CH$_3$O-p-CN-phenyl | CN | cyclopropyl | F |
| 211. | o,o'-di-CH$_3$O-p-CN-phenyl | CH=CHCN | CH$_3$ | F |
| 212. | o,o'-di-CH$_3$O-p-CN-phenyl | CH=CHCN | cyclopropyl | F |
| 213. | o,o'-di-CH$_3$-p-CN-phenyl | CN | CH$_3$ | F |
| 214. | o,o'-di-CH$_3$-p-CN-phenyl | CN | cyclopropyl | F |
| 215. | o,o'-di-CH$_3$-p-CN-phenyl | CH=CHCN | CH$_3$ | F |
| 216. | o,o'-di-CH$_3$-p-CN-phenyl | CH=CHCN | cyclopropyl | F |
| 217. | o,o'-diCH$_3$O-p-(CH=CHCN)-phenyl | SO$_2$NH$_2$ | CH$_3$ | CH$_3$ |
| 218. | o,o'-diCH$_3$O-p-(CH=CHCN)-phenyl | SO$_2$NH$_2$ | cyclopropyl | CH$_3$ |
| 219. | o,o'-diCH$_3$O-p-(CH=CHCN)-phenyl | SO$_2$NH$_2$ | cyclopropyl | H |
| 220. | o,o'-diCH$_3$O-p-(CH=CHCN)-phenyl | SO$_2$NH$_2$ | CH$_3$ | H |
| 221. | o,o'-diCH$_3$O-p-(CH=CHCN)-phenyl | SO$_2$NH$_2$ | CH$_3$ | CH$_3$ |
| 222. | o,o'-diCH$_3$O-p-(CH=CHCN)-phenyl | F | cyclopropyl | CH$_3$ |

TABLE 3-continued

Contemplated Compounds of Formula IA-3

| | Ar | V | W | Z |
|---|---|---|---|---|
| 223. | o,o'-diCH₃O-p-(CH=CHCN)-phenyl | F | cyclopropyl | H |
| 224. | o,o'-diCH₃O-p-(CH=CHCN)-phenyl | F | CH₃ | H |
| 225. | 4-cyclopropylnaphth-1-yl | SO₂NH₂ | CH₃ | CH₃ |
| 226. | 4-cyclopropylnaphth-1-yl | SO₂NH₂ | cyclopropyl | CH₃ |
| 227. | 4-cyclopropylnaphth-1-yl | SO₂NH₂ | cyclopropyl | H |
| 228. | 4-cyclopropylnaphth-1-yl | SO₂NH₂ | CH₃ | H |
| 229. | 4-cyclopropylnaphth-1-yl | F | CH₃ | CH₃ |
| 230. | 4-cyclopropylnaphth-1-yl | F | cyclopropyl | CH₃ |
| 231. | 4-cyclopropylnaphth-1-yl | F | cyclopropyl | H |
| 232. | 4-cyclopropylnaphth-1-yl | F | CH₃ | H |
| 233. | o,o'-di-CH₃O-p-CN-phenyl | SO₂NH₂ | CH₃ | CH₃ |
| 234. | o,o'-di-CH₃O-p-CN-phenyl | SO₂NH₂ | cyclopropyl | CH₃ |
| 235. | o,o'-di-CH₃O-p-CN-phenyl | SO₂NH₂ | cyclopropyl | H |
| 236. | o,o'-di-CH₃O-p-CN-phenyl | SO₂NH₂ | CH₃ | H |
| 237. | o,o'-di-CH₃O-p-CN-phenyl | F | CH₃ | CH₃ |
| 238. | o,o'-di-CH₃O-p-CN-phenyl | F | cyclopropyl | CH₃ |
| 239. | o,o'-di-CH₃O-p-CN-phenyl | F | cyclopropyl | H |
| 240. | o,o'-di-CH₃O-p-CN-phenyl | F | CH₃ | H |
| 241. | o,o'-di-CH₃-p-CN-phenyl | SO₂NH₂ | CH₃ | CH₃ |
| 242. | o,o'-di-CH₃-p-CN-phenyl | SO₂NH₂ | cyclopropyl | CH₃ |
| 243. | o,o'-di-CH₃-p-CN-phenyl | SO₂NH₂ | cyclopropyl | H |
| 244. | o,o'-di-CH₃-p-CN-phenyl | SO₂NH₂ | CH₃ | H |
| 245. | o,o'-di-CH₃-p-CN-phenyl | F | CH₃ | CH₃ |
| 246. | o,o'-di-CH₃-p-CN-phenyl | F | cyclopropyl | CH₃ |
| 247. | o,o'-di-CH₃-p-CN-phenyl | F | cyclopropyl | H |
| 248. | o,o'-di-CH₃-p-CN-phenyl | F | CH₃ | H |
| 249. | o,o'-diCH₃O-p-(CH=CHCN)-phenyl | SO₂NH₂ | CH₃ | F |
| 250. | o,o'-diCH₃O-p-(CH=CHCN)-phenyl | SO₂NH₂ | cyclopropyl | F |
| 251. | o,o'-diCH₃O-p-(CH=CHCN)-phenyl | F | cyclopropyl | F |
| 252. | o,o'-diCH₃O-p-(CH=CHCN)-phenyl | F | CH₃ | F |
| 253. | 4-cyclopropylnaphth-1-yl | SO₂NH₂ | CH₃ | F |
| 254. | 4-cyclopropylnaphth-1-yl | SO₂NH₂ | cyclopropyl | F |
| 255. | 4-cyclopropylnaphth-1-yl | F | CH₃ | F |
| 256. | 4-cyclopropylnaphth-1-yl | F | cyclopropyl | F |
| 257. | o,o'-di-CH₃O-p-CN-phenyl | SO₂NH₂ | CH₃ | F |
| 258. | o,o'-di-CH₃O-p-CN-phenyl | SO₂NH₂ | cyclopropyl | F |
| 259. | o,o'-di-CH₃O-p-CN-phenyl | F | CH₃ | F |
| 260. | o,o'-di-CH₃O-p-CN-phenyl | F | cyclopropyl | F |
| 261. | o,o'-di-CH₃-p-CN-phenyl | SO₂NH₂ | CH₃ | F |
| 262. | o,o'-di-CH₃-p-CN-phenyl | SO₂NH₂ | cyclopropyl | F |
| 263. | o,o'-di-CH₃-p-CN-phenyl | F | CH₃ | F |
| 264. | o,o'-di-CH₃-p-CN-phenyl | F | cyclopropyl | F |
| 265. | 4-cyclopropyl phenyl | CN | CH₃ | CH₃ |
| 266. | 4-cyclopropyl phenyl | CN | cyclopropyl | CH₃ |
| 267. | 2,4,6-trimethyl phenyl | CN | cyclopropyl | H |
| 268. | 2,4,6-trimethyl phenyl | CN | CH₃ | H |
| 269. | 2,4,6-trimethyl phenyl | CH=CHCN | CH₃ | CH₃ |
| 270. | 2,4,6-trimethyl phenyl | CH=CHCN | cyclopropyl | CH₃ |
| 271. | 2,4,6-trimethyl phenyl | CH=CHCN | cyclopropyl | H |
| 272. | 2,4,6-trimethyl phenyl | CH=CHCN | CH₃ | H |
| 273. | 2,4,6-trimethyl phenyl | CN | CH₃ | F |
| 274. | 2,4,6-trimethyl phenyl | CN | cyclopropyl | F |
| 275. | 2,4,6-trimethyl phenyl | CH=CHCN | CH₃ | F |
| 276. | 2,4,6-trimethyl phenyl | CH=CHCN | cyclopropyl | F |
| 277. | 2,4,6-trimethyl phenyl | SO₂NH₂ | CH₃ | CH₃ |
| 278. | 2,4,6-trimethyl phenyl | SO₂NH₂ | cyclopropyl | CH₃ |
| 279. | 2,4,6-trimethyl phenyl | SO₂NH₂ | cyclopropyl | H |
| 280. | 2,4,6-trimethyl phenyl | SO₂NH₂ | CH₃ | H |
| 281. | 2,4,6-trimethyl phenyl | F | CH₃ | CH₃ |
| 282. | 2,4,6-trimethyl phenyl | F | cyclopropyl | CH₃ |
| 283. | 2,4,6-trimethyl phenyl | F | cyclopropyl | H |
| 284. | 2,4,6-trimethyl phenyl | F | CH₃ | H |
| 285. | 4-cyclopropyl phenyl | SO₂NH₂ | CH₃ | F |
| 286. | 4-cyclopropyl phenyl | SO₂NH₂ | cyclopropyl | F |
| 287. | 4-cyclopropyl phenyl | F | CH₃ | F |
| 288. | 4-cyclopropyl phenyl | F | cyclopropyl | F |
| 289. | 2,4,6-trimethyl phenyl | CN | CH₃ | CH₃ |
| 290. | 2,4,6-trimethyl phenyl | CN | cyclopropyl | CH₃ |
| 291. | o,o'-dimethyl-p-cyclopropyl phenyl | CN | cyclopropyl | H |
| 292. | o,o'-dimethyl-p-cyclopropyl phenyl | CN | CH₃ | H |
| 293. | o,o'-dimethyl-p-cyclopropyl phenyl | CH=CHCN | CH₃ | CH₃ |
| 294. | o,o'-dimethyl-p-cyclopropyl phenyl | CH=CHCN | cyclopropyl | CH₃ |
| 295. | o,o'-dimethyl-p-cyclopropyl phenyl | CH=CHCN | cyclopropyl | H |
| 296. | o,o'-dimethyl-p-cyclopropyl phenyl | CH=CHCN | CH₃ | H |
| 297. | o,o'-dimethyl-p-cyclopropyl phenyl | CN | CH₃ | F |
| 298 | o,o'-dimethyl-p-cyclopropyl phenyl | CN | cyclopropyl | F |
| 299. | o,o'-dimethyl-p-cyclopropyl phenyl | CH=CHCN | CH₃ | F |
| 300. | o,o'-dimethyl-p-cyclopropyl phenyl | CH=CHCN | cyclopropyl | F |
| 301. | o,o'-dimethyl-p-cyclopropyl phenyl | SO₂NH₂ | CH₃ | CH₃ |
| 302. | o,o'-dimethyl-p-cyclopropyl phenyl | SO₂NH₂ | cyclopropyl | CH₃ |
| 303. | o,o'-dimethyl-p-cyclopropyl phenyl | SO₂NH₂ | cyclopropyl | H |
| 304. | o,o'-dimethyl-p-cyclopropyl phenyl | SO₂NH₂ | CH₃ | H |
| 305. | o,o'-dimethyl-p-cyclopropyl phenyl | F | CH₃ | CH₃ |

TABLE 3-continued

Contemplated Compounds of Formula IA-3

| | Ar | V | W | Z |
|---|---|---|---|---|
| 306. | o,o'-dimethyl-p-cyclopropyl phenyl | F | cyclopropyl | CH₃ |
| 307. | o,o'-dimethyl-p-cyclopropyl phenyl | F | cyclopropyl | H |
| 308. | o,o'-dimethyl-p-cyclopropyl phenyl | F | CH₃ | H |
| 309. | 2,4,6-trimethyl phenyl | SO₂NH₂ | CH₃ | F |
| 310. | 2,4,6-trimethyl phenyl | SO₂NH₂ | cyclopropyl | F |
| 311. | 2,4,6-trimethyl phenyl | F | CH₃ | F |
| 312. | 2,4,6-trimethyl phenyl | F | cyclopropyl | F |
| 313. | o,o'-di-CH₃-p-acetyl-phenyl | CN | H | H |
| 314. | o,o'-di-CH₃-p-acetyl-phenyl | CN | CH₃ | H |
| 315. | o,o'-di-CH₃-p-acetyl-phenyl | CN | H | Cl |
| 316. | o,o'-di-CH₃-p-acetyl-phenyl | CN | CH₃ | Cl |

TABLE 4

Contemplated Compounds of Formula IA-4

| | Ar | V | W | Z |
|---|---|---|---|---|
| 1. | o,o'-diCH₃O-p-(CH=CHCN)-phenyl | CN | H | H |
| 2. | o,o'-diCH₃O-p-(CH=CHCN)-phenyl | CN | CH₃ | H |
| 3. | o,o'-diCH₃O-p-(CH=CHCN)-phenyl | CN | F | CH₃ |
| 4. | o,o'-diCH₃O-p-(CH=CHCN)-phenyl | CN | Cl | CH₃ |
| 5. | o,o'-diCH₃O-p-(CH=CHCN)-phenyl | CN | F | H |
| 6. | o,o'-diCH₃O-p-(CH=CHCN)-phenyl | CH=CHCN | Cl | H |
| 7. | o,o'-diCH₃O-p-(CH=CHCN)-phenyl | CH=CHCN | Br | CH₃ |
| 8. | o,o'-diCH₃O-p-(CH=CHCN)-phenyl | CH=CHCN | H | CH₃ |
| 9. | 4-cyclopropylnaphth-1-yl | CN | H | H |
| 10. | 4-cyclopropylnaphth-1-yl | CN | CH₃ | H |
| 11. | 4-cyclopropylnaphth-1-yl | CN | F | CH₃ |
| 12. | 4-cyclopropylnaphth-1-yl | CN | Cl | CH₃ |
| 13. | 4-cyclopropylnaphth-1-yl | CH=CHCN | Cl | H |
| 14. | 4-cyclopropylnaphth-1-yl | CH=CHCN | CH₃ | H |
| 15. | 4-cyclopropylnaphth-1-yl | CH=CHCN | F | CH₃ |
| 16. | 4-cyclopropylnaphth-1-yl | CH=CHCN | Cl | CH₃ |
| 17. | o,o'-di-CH₃O-p-CN-phenyl | CN | Br | H |
| 18. | o,o'-di-CH₃O-p-CN-phenyl | CN | H | H |
| 19. | o,o'-di-CH₃O-p-CN-phenyl | CN | CH₃ | CH₃ |
| 20. | o,o'-di-CH₃O-p-CN-phenyl | CN | F | CH₃ |
| 21. | o,o'-di-CH₃O-p-CN-phenyl | CH=CHCN | H | H |
| 22. | o,o'-di-CH₃O-p-CN-phenyl | CH=CHCN | CH₃ | H |
| 23. | o,o'-di-CH₃O-p-CN-phenyl | CH=CHCN | F | CH₃ |
| 24. | o,o'-di-CH₃O-p-CN-phenyl | CH=CHCN | Cl | CH₃ |
| 25. | o,o'-diCH₃O-p-(CH=CHCN)-phenyl | CN | F | CH₃ |
| 26. | o,o'-diCH₃O-p-(CH=CHCN)-phenyl | CN | Cl | CH₃ |
| 27. | o,o'-diCH₃O-p-(CH=CHCN)-phenyl | CN | Cl | H |
| 28. | o,o'-diCH₃O-p-(CH=CHCN)-phenyl | CN | F | H |
| 29. | o,o'-diCH₃O-p-(CH=CHCN)-phenyl | CN | H | CH₃ |
| 30. | o,o'-diCH₃O-p-(CH=CHCN)-phenyl | CH=CHCN | CH₃ | CH₃ |
| 31. | o,o'-diCH₃O-p-(CH=CHCN)-phenyl | CH=CHCN | F | H |
| 32. | o,o'-diCH₃O-p-(CH=CHCN)-phenyl | CH=CHCN | Cl | H |
| 33. | 4-cyclopropylnaphth-1-yl | CN | H | ethyl |
| 34. | 4-cyclopropylnaphth-1-yl | CN | Cl | ethyl |
| 35. | 4-cyclopropylnaphth-1-yl | CN | F | H |
| 36. | 4-cyclopropylnaphth-1-yl | CN | Cl | H |
| 37. | 4-cyclopropylnaphth-1-yl | CH=CHCN | Br | ethyl |
| 38. | 4-cyclopropylnaphth-1-yl | CH=CHCN | H | ethyl |
| 39. | 4-cyclopropylnaphth-1-yl | CH=CHCN | H | H |
| 40. | 4-cyclopropylnaphth-1-yl | CH=CHCN | CH₃ | H |
| 41. | o,o'-di-CH₃O-p-CN-phenyl | CN | F | CH₃ |
| 42. | o,o'-di-CH₃O-p-CN-phenyl | CN | Cl | CH₃ |
| 43. | o,o'-di-CH₃O-p-CN-phenyl | CN | Cl | H |
| 44. | o,o'-di-CH₃O-p-CN-phenyl | CN | F | H |
| 45. | o,o'-di-CH₃O-p-CN-phenyl | C≡CCH₃ | Cl | CH₃ |
| 46. | o,o'-di-CH₃O-p-CN-phenyl | CH=CHCN | Br | CH₃ |
| 47. | o,o'-di-CH₃O-p-CN-phenyl | CH=CHCN | Br | H |
| 48. | o,o'-di-CH₃O-p-CN-phenyl | CH=CHCN | H | H |
| 49. | o,o'-diCH₃O-p-(CH=CHCN)-phenyl | CN | CH₃ | H |
| 50. | o,o'-diCH₃O-p-(CH=CHCN)-phenyl | CN | CH₃ | benzyl |
| 51. | o,o'-diCH₃O-p-(CH=CHCN)-phenyl | CN | H | benzyl |
| 52. | o,o'-diCH₃O-p-(CH=CHCN)-phenyl | CN | H | H |
| 53. | o,o'-diCH₃O-p-(CH=CHCN)-phenyl | CN | CH₃ | H |
| 54. | o,o'-diCH₃O-p-(CH=CHCN)-phenyl | CH=CHCN | CH₃ | benzyl |
| 55. | o,o'-diCH₃O-p-(CH=CHCN)-phenyl | CH=CHCN | H | benzyl |
| 56. | o,o'-diCH₃O-p-(CH=CHCN)-phenyl | CH=CHCN | H | H |
| 57. | 4-cyclopropylnaphth-1-yl | CN | CH₃ | H |
| 58. | 4-cyclopropylnaphth-1-yl | CN | CH₃ | benzyl |
| 59. | 4-cyclopropylnaphth-1-yl | CN | H | benzyl |
| 60. | 4-cyclopropylnaphth-1-yl | CN | H | H |
| 61. | 4-cyclopropylnaphth-1-yl | CH=CHCN | CH₃ | H |
| 62. | 4-cyclopropylnaphth-1-yl | CH=CHCN | CH₃ | benzyl |
| 63. | 4-cyclopropylnaphth-1-yl | CH=CHCN | H | benzyl |
| 64. | 4-cyclopropylnaphth-1-yl | CH=CHCN | H | H |
| 65. | o,o'-di-CH₃O-p-CN-phenyl | CN | CH₃ | H |
| 66. | o,o'-di-CH₃O-p-CN-phenyl | CN | CH₃ | benzyl |
| 67. | o,o'-di-CH₃O-p-CN-phenyl | CN | H | benzyl |
| 68. | o,o'-di-CH₃O-p-CN-phenyl | CN | H | H |

TABLE 4-continued

Contemplated Compounds of Formula IA-4

| # | Ar | V | W | Z |
|---|---|---|---|---|
| 69. | o,o'-di-CH$_3$O-p-CN-phenyl | CH=CHCN | CH$_3$ | H |
| 70. | o,o'-di-CH$_3$O-p-CN-phenyl | CH=CHCN | CH$_3$ | benzyl |
| 71. | o,o'-di-CH$_3$O-p-CN-phenyl | CH=CHCN | H | benzyl |
| 72. | o,o'-di-CH$_3$O-p-CN-phenyl | CH=CHCN | H | H |
| 73. | o,o'-di-CH$_3$-p-CN-phenyl | CN | CH$_3$ | H |
| 74. | o,o'-di-CH$_3$-p-CN-phenyl | CN | CH$_3$ | benzyl |
| 75. | o,o'-di-CH$_3$-p-CN-phenyl | CN | H | benzyl |
| 76. | o,o'-di-CH$_3$-p-CN-phenyl | CN | H | H |
| 77. | o,o'-di-CH$_3$-p-CN-phenyl | CH=CHCN | CH$_3$ | H |
| 78. | o,o'-di-CH$_3$-p-CN-phenyl | CH=CHCN | CH$_3$ | benzyl |
| 79. | o,o'-di-CH$_3$-p-CN-phenyl | CH=CHCN | H | benzyl |
| 80. | o,o'-di-CH$_3$-p-CN-phenyl | CH=CHCN | H | H |
| 81. | o,o'-diCH$_3$O-p-(CH=CHCN)-phenyl | CN | F | H |
| 82. | o,o'-diCH$_3$O-p-(CH=CHCN)-phenyl | CN | F | benzyl |
| 83. | o,o'-diCH$_3$O-p-(CH=CHCN)-phenyl | CH=CHCN | F | benzyl |
| 84. | o,o'-diCH$_3$O-p-(CH=CHCN)-phenyl | CH=CHCN | F | H |
| 85. | 4-cyclopropylnaphth-1-yl | CN | F | H |
| 86. | 4-cyclopropylnaphth-1-yl | CN | F | benzyl |
| 87. | 4-cyclopropylnaphth-1-yl | CH=CHCN | F | H |
| 88. | 4-cyclopropylnaphth-1-yl | CH=CHCN | F | benzyl |
| 89. | o,o'-di-CH$_3$O-p-CN-phenyl | CN | F | H |
| 90. | o,o'-di-CH$_3$O-p-CN-phenyl | CN | F | benzyl |
| 91. | o,o'-di-CH$_3$O-p-CN-phenyl | CH=CHCN | F | H |
| 92. | o,o'-di-CH$_3$O-p-CN-phenyl | CH=CHCN | F | benzyl |
| 93. | o,o'-di-CH$_3$-p-CN-phenyl | CN | F | H |
| 94. | o,o'-di-CH$_3$-p-CN-phenyl | CN | F | benzyl |
| 95. | o,o'-di-CH$_3$-p-CN-phenyl | CH=CHCN | F | H |
| 96. | o,o'-di-CH$_3$-p-CN-phenyl | CH=CHCN | F | benzyl |
| 97. | o,o'-diCH$_3$O-p-(CH=CHCN)-phenyl | SO$_2$NH$_2$ | CH$_3$ | H |
| 98. | o,o'-diCH$_3$O-p-(CH=CHCN)-phenyl | SO$_2$NH$_2$ | CH$_3$ | benzyl |
| 99. | o,o'-diCH$_3$O-p-(CH=CHCN)-phenyl | SO$_2$NH$_2$ | H | benzyl |
| 100. | o,o'-diCH$_3$O-p-(CH=CHCN)-phenyl | SO$_2$NH$_2$ | H | H |
| 101. | o,o'-diCH$_3$O-p-(CH=CHCN)-phenyl | SO$_2$NH$_2$ | CH$_3$ | H |
| 102. | o,o'-diCH$_3$O-p-(CH=CHCN)-phenyl | F | CH$_3$ | benzyl |
| 103. | o,o'-diCH$_3$O-p-(CH=CHCN)-phenyl | F | H | benzyl |
| 104. | o,o'-diCH$_3$O-p-(CH=CHCN)-phenyl | F | H | H |
| 105. | 4-cyclopropylnaphth-1-yl | SO$_2$NH$_2$ | CH$_3$ | H |
| 106. | 4-cyclopropylnaphth-1-yl | SO$_2$NH$_2$ | CH$_3$ | benzyl |
| 107. | 4-cyclopropylnaphth-1-yl | SO$_2$NH$_2$ | H | benzyl |
| 108. | 4-cyclopropylnaphth-1-yl | SO$_2$NH$_2$ | H | H |
| 109. | 4-cyclopropylnaphth-1-yl | F | CH$_3$ | H |
| 110. | 4-cyclopropylnaphth-1-yl | F | CH$_3$ | benzyl |
| 111. | 4-cyclopropylnaphth-1-yl | F | H | benzyl |
| 112. | 4-cyclopropylnaphth-1-yl | F | H | H |
| 113. | o,o'-di-CH$_3$O-p-CN-phenyl | SO$_2$NH$_2$ | CH$_3$ | H |
| 114. | o,o'-di-CH$_3$O-p-CN-phenyl | SO$_2$NH$_2$ | CH$_3$ | benzyl |
| 115. | o,o'-di-CH$_3$O-p-CN-phenyl | SO$_2$NH$_2$ | H | benzyl |
| 116. | o,o'-di-CH$_3$O-p-CN-phenyl | SO$_2$NH$_2$ | H | H |
| 117. | o,o'-di-CH$_3$O-p-CN-phenyl | F | CH$_3$ | H |
| 118. | o,o'-di-CH$_3$O-p-CN-phenyl | F | CH$_3$ | benzyl |
| 119. | o,o'-di-CH$_3$O-p-CN-phenyl | F | H | benzyl |
| 120. | o,o'-di-CH$_3$O-p-CN-phenyl | F | H | H |
| 121. | o,o'-di-CH$_3$-p-CN-phenyl | SO$_2$NH$_2$ | CH$_3$ | H |
| 122. | o,o'-di-CH$_3$-p-CN-phenyl | SO$_2$NH$_2$ | CH$_3$ | benzyl |
| 123. | o,o'-di-CH$_3$-p-CN-phenyl | SO$_2$NH$_2$ | H | benzyl |
| 124. | o,o'-di-CH$_3$-p-CN-phenyl | SO$_2$NH$_2$ | H | H |
| 125. | o,o'-di-CH$_3$-p-CN-phenyl | F | CH$_3$ | H |
| 126. | o,o'-di-CH$_3$-p-CN-phenyl | F | CH$_3$ | benzyl |
| 127. | o,o'-di-CH$_3$-p-CN-phenyl | F | H | benzyl |
| 128. | o,o'-di-CH$_3$-p-CN-phenyl | F | H | H |
| 129. | o,o'-diCH$_3$O-p-(CH=CHCN)-phenyl | SO$_2$NH$_2$ | F | H |
| 130. | o,o'-diCH$_3$O-p-(CH=CHCN)-phenyl | SO$_2$NH$_2$ | F | benzyl |
| 131. | o,o'-diCH$_3$O-p-(CH=CHCN)-phenyl | F | F | benzyl |
| 132. | o,o'-diCH$_3$O-p-(CH=CHCN)-phenyl | F | F | H |
| 133. | 4-cyclopropylnaphth-1-yl | SO$_2$NH$_2$ | F | H |
| 134. | 4-cyclopropylnaphth-1-yl | SO$_2$NH$_2$ | F | benzyl |
| 135. | 4-cyclopropylnaphth-1-yl | F | F | H |
| 136. | 4-cyclopropylnaphth-1-yl | F | F | benzyl |
| 137. | o,o'-di-CH$_3$O-p-CN-phenyl | SO$_2$NH$_2$ | F | H |
| 138. | o,o'-di-CH$_3$O-p-CN-phenyl | SO$_2$NH$_2$ | F | benzyl |
| 139. | o,o'-di-CH$_3$O-p-CN-phenyl | F | F | H |
| 140. | o,o'-di-CH$_3$O-p-CN-phenyl | F | F | benzyl |
| 141. | o,o'-di-CH$_3$-p-CN-phenyl | SO$_2$NH$_2$ | F | H |
| 142. | o,o'-di-CH$_3$-p-CN-phenyl | SO$_2$NH$_2$ | F | benzyl |
| 143. | o,o'-di-CH$_3$-p-CN-phenyl | F | F | H |
| 144. | o,o'-di-CH$_3$-p-CN-phenyl | F | F | benzyl |
| 145. | 4-cyclopropyl phenyl | CN | CH$_3$ | H |
| 146. | 4-cyclopropyl phenyl | CN | CH$_3$ | benzyl |
| 147. | 4-cyclopropyl phenyl | CN | H | benzyl |
| 148. | 2,4,6-trimethyl phenyl | CN | H | H |
| 149. | 2,4,6-trimethyl phenyl | CH=CHCN | CH$_3$ | H |
| 150. | 2,4,6-trimethyl phenyl | CH=CHCN | CH$_3$ | benzyl |
| 151. | 2,4,6-trimethyl phenyl | CH=CHCN | H | benzyl |
| 152. | 2,4,6-trimethyl phenyl | CH=CHCN | H | H |
| 153. | 2,4,6-trimethyl phenyl | CN | F | H |
| 154. | 2,4,6-trimethyl phenyl | CN | F | benzyl |
| 155. | 2,4,6-trimethyl phenyl | CH=CHCN | F | H |
| 156. | 2,4,6-trimethyl phenyl | CH=CHCN | F | benzyl |
| 157. | 2,4,6-trimethyl phenyl | SO$_2$NH$_2$ | CH$_3$ | H |
| 158. | 2,4,6-trimethyl phenyl | SO$_2$NH$_2$ | CH$_3$ | benzyl |
| 159. | 2,4,6-trimethyl phenyl | SO$_2$NH$_2$ | H | benzyl |
| 160. | 2,4,6-trimethyl phenyl | SO$_2$NH$_2$ | H | H |
| 161. | 2,4,6-trimethyl phenyl | F | CH$_3$ | H |
| 162. | 2,4,6-trimethyl phenyl | F | CH$_3$ | benzyl |
| 163. | 2,4,6-trimethyl phenyl | F | H | benzyl |
| 164. | 2,4,6-trimethyl phenyl | F | H | H |
| 165. | 2,4,6-trimethyl phenyl | SO$_2$NH$_2$ | F | H |
| 166. | 2,4,6-trimethyl phenyl | SO$_2$NH$_2$ | F | benzyl |
| 167. | 4-cyclopropyl phenyl | F | F | H |
| 168. | 4-cyclopropyl phenyl | F | F | benzyl |
| 169. | 2,4,6-trimethyl phenyl | CN | CH$_3$ | H |
| 170. | 2,4,6-trimethyl phenyl | CN | CH$_3$ | benzyl |
| 171. | 2,4,6-trimethyl phenyl | CN | H | benzyl |
| 172. | o,o'-dimethyl-p-cyclopropyl phenyl | CN | H | H |
| 173. | o,o'-dimethyl-p-cyclopropyl phenyl | CH=CHCN | CH$_3$ | H |
| 174. | o,o'-dimethyl-p-cyclopropyl phenyl | CH=CHCN | CH$_3$ | benzyl |
| 175. | o,o'-dimethyl-p-cyclopropyl phenyl | CH=CHCN | H | benzyl |
| 176. | o,o'-dimethyl-p-cyclopropyl phenyl | CH=CHCN | H | H |
| 177. | o,o'-dimethyl-p-cyclopropyl phenyl | CN | F | H |
| 178. | o,o'-dimethyl-p-cyclopropyl phenyl | CN | F | benzyl |
| 179. | o,o'-dimethyl-p-cyclopropyl phenyl | CH=CHCN | F | H |
| 180. | o,o'-dimethyl-p-cyclopropyl phenyl | CH=CHCN | F | benzyl |

TABLE 4-continued

Contemplated Compounds of Formula IA-4

| # | Ar | V | W | Z |
|---|---|---|---|---|
| 181. | o,o'-dimethyl-p-cyclopropyl phenyl | SO$_2$NH$_2$ | CH$_3$ | H |
| 182. | o,o'-dimethyl-p-cyclopropyl phenyl | SO$_2$NH$_2$ | CH$_3$ | benzyl |
| 183. | o,o'-dimethyl-p-cyclopropyl phenyl | SO$_2$NH$_2$ | H | benzyl |
| 184. | o,o'-dimethyl-p-cyclopropyl phenyl | SO$_2$NH$_2$ | H | H |
| 185. | o,o'-dimethyl-p-cyclopropyl phenyl | F | CH$_3$ | H |
| 186. | o,o'-dimethyl-p-cyclopropyl phenyl | F | CH$_3$ | benzyl |
| 187. | o,o'-dimethyl-p-cyclopropyl phenyl | F | H | benzyl |
| 188. | o,o'-dimethyl-p-cyclopropyl phenyl | F | H | H |
| 189. | o,o'-dimethyl-p-cyclopropyl phenyl | SO$_2$NH$_2$ | F | H |
| 190. | o,o'-dimethyl-p-cyclopropyl phenyl | SO$_2$NH$_2$ | F | benzyl |
| 191. | 2,4,6-trimethyl phenyl | F | F | H |
| 192. | 2,4,6-trimethyl phenyl | F | F | benzyl |
| 193. | o,o'-diCH$_3$O-p-(CH=CHCN)-phenyl | CN | CH$_3$ | CH$_3$ |
| 194. | o,o'-diCH$_3$O-p-(CH=CHCN)-phenyl | CN | CH$_3$ | cyclopropyl |
| 195. | o,o'-diCH$_3$O-p-(CH=CHCN)-phenyl | CN | H | cyclopropyl |
| 196. | o,o'-diCH$_3$O-p-(CH=CHCN)-phenyl | CN | H | CH$_3$ |
| 197. | o,o'-diCH$_3$O-p-(CH=CHCN)-phenyl | CN | CH$_3$ | CH$_3$ |
| 198. | o,o'-diCH$_3$O-p-(CH=CHCN)-phenyl | CH=CHCN | CH$_3$ | cyclopropyl |
| 199. | o,o'-diCH$_3$O-p-(CH=CHCN)-phenyl | CH=CHCN | H | cyclopropyl |
| 200. | o,o'-diCH$_3$O-p-(CH=CHCN)-phenyl | CH=CHCN | H | CH$_3$ |
| 201. | 4-cyclopropylnaphth-1-yl | CN | CH$_3$ | CH$_3$ |
| 202. | 4-cyclopropylnaphth-1-yl | CN | CH$_3$ | cyclopropyl |
| 203. | 4-cyclopropylnaphth-1-yl | CN | H | cyclopropyl |
| 204. | 4-cyclopropylnaphth-1-yl | CN | H | CH$_3$ |
| 205. | 4-cyclopropylnaphth-1-yl | CH=CHCN | CH$_3$ | CH$_3$ |
| 206. | 4-cyclopropylnaphth-1-yl | CH=CHCN | CH$_3$ | cyclopropyl |
| 207. | 4-cyclopropylnaphth-1-yl | CH=CHCN | H | cyclopropyl |
| 208. | 4-cyclopropylnaphth-1-yl | CH=CHCN | H | CH$_3$ |
| 209. | o,o'-di-CH$_3$O-p-CN-phenyl | CN | CH$_3$ | CH$_3$ |
| 210. | o,o'-di-CH$_3$O-p-CN-phenyl | CN | CH$_3$ | cyclopropyl |
| 211. | o,o'-di-CH$_3$O-p-CN-phenyl | CN | H | cyclopropyl |
| 212. | o,o'-di-CH$_3$O-p-CN-phenyl | CN | H | CH$_3$ |
| 213. | o,o'-di-CH$_3$O-p-CN-phenyl | CH=CHCN | CH$_3$ | CH$_3$ |
| 214. | o,o'-di-CH$_3$O-p-CN-phenyl | CH=CHCN | CH$_3$ | cyclopropyl |
| 215. | o,o'-di-CH$_3$O-p-CN-phenyl | CH=CHCN | H | cyclopropyl |
| 216. | o,o'-di-CH$_3$O-p-CN-phenyl | CH=CHCN | H | CH$_3$ |
| 217. | o,o'-di-CH$_3$-p-CN-phenyl | CN | CH$_3$ | CH$_3$ |
| 218. | o,o'-di-CH$_3$-p-CN-phenyl | CN | CH$_3$ | cyclopropyl |
| 219. | o,o'-di-CH$_3$-p-CN-phenyl | CN | H | cyclopropyl |
| 220. | o,o'-di-CH$_3$-p-CN-phenyl | CN | H | CH$_3$ |
| 221. | o,o'-di-CH$_3$-p-CN-phenyl | CH=CHCN | CH$_3$ | CH$_3$ |
| 222. | o,o'-di-CH$_3$-p-CN-phenyl | CH=CHCN | CH$_3$ | cyclopropyl |
| 223. | o,o'-di-CH$_3$-p-CN-phenyl | CH=CHCN | H | cyclopropyl |
| 224. | o,o'-di-CH$_3$-p-CN-phenyl | CH=CHCN | H | CH$_3$ |
| 225. | o,o'-diCH$_3$O-p-(CH=CHCN)-phenyl | CN | F | CH$_3$ |
| 226. | o,o'-diCH$_3$O-p-(CH=CHCN)-phenyl | CN | F | cyclopropyl |
| 227. | o,o'-diCH$_3$O-p-(CH=CHCN)-phenyl | CH=CHCN | F | cyclopropyl |
| 228. | o,o'-diCH$_3$O-p-(CH=CHCN)-phenyl | CH=CHCN | F | CH$_3$ |
| 229. | 4-cyclopropylnaphth-1-yl | CN | F | CH$_3$ |
| 230. | 4-cyclopropylnaphth-1-yl | CN | F | cyclopropyl |
| 231. | 4-cyclopropylnaphth-1-yl | CH=CHCN | F | CH$_3$ |
| 232. | 4-cyclopropylnaphth-1-yl | CH=CHCN | F | cyclopropyl |
| 233. | o,o'-di-CH$_3$O-p-CN-phenyl | CN | F | CH$_3$ |
| 234. | o,o'-di-CH$_3$O-p-CN-phenyl | CN | F | cyclopropyl |
| 235. | o,o'-di-CH$_3$O-p-CN-phenyl | CH=CHCN | F | CH$_3$ |
| 236. | o,o'-di-CH$_3$O-p-CN-phenyl | CH=CHCN | F | cyclopropyl |
| 237. | o,o'-di-CH$_3$-p-CN-phenyl | CN | F | CH$_3$ |
| 238. | o,o'-di-CH$_3$-p-CN-phenyl | CN | F | cyclopropyl |
| 239. | o,o'-di-CH$_3$-p-CN-phenyl | CH=CHCN | F | CH$_3$ |
| 240. | o,o'-di-CH$_3$-p-CN-phenyl | CH=CHCN | F | cyclopropyl |
| 241. | o,o'-diCH$_3$O-p-(CH=CHCN)-phenyl | SO$_2$NH$_2$ | CH$_3$ | CH$_3$ |
| 242. | o,o'-diCH$_3$O-p-(CH=CHCN)-phenyl | SO$_2$NH$_2$ | CH$_3$ | cyclopropyl |
| 243. | o,o'-diCH$_3$O-p-(CH=CHCN)-phenyl | SO$_2$NH$_2$ | H | cyclopropyl |
| 244. | o,o'-diCH$_3$O-p-(CH=CHCN)-phenyl | SO$_2$NH$_2$ | H | CH$_3$ |
| 245. | o,o'-diCH$_3$O-p-(CH=CHCN)-phenyl | SO$_2$NH$_2$ | CH$_3$ | CH$_3$ |
| 246. | o,o'-diCH$_3$O-p-(CH=CHCN)-phenyl | F | CH$_3$ | cyclopropyl |
| 247. | o,o'-diCH$_3$O-p-(CH=CHCN)-phenyl | F | H | cyclopropyl |
| 248. | o,o'-diCH$_3$O-p-(CH=CHCN)-phenyl | F | H | CH$_3$ |
| 249. | 4-cyclopropylnaphth-1-yl | SO$_2$NH$_2$ | CH$_3$ | CH$_3$ |
| 250. | 4-cyclopropylnaphth-1-yl | SO$_2$NH$_2$ | CH$_3$ | cyclopropyl |
| 251. | 4-cyclopropylnaphth-1-yl | SO$_2$NH$_2$ | H | cyclopropyl |
| 252. | 4-cyclopropylnaphth-1-yl | SO$_2$NH$_2$ | H | CH$_3$ |
| 253. | 4-cyclopropylnaphth-1-yl | F | CH$_3$ | CH$_3$ |
| 254. | 4-cyclopropylnaphth-1-yl | F | CH$_3$ | cyclopropyl |
| 255. | 4-cyclopropylnaphth-1-yl | F | H | cyclopropyl |
| 256. | 4-cyclopropylnaphth-1-yl | F | H | CH$_3$ |
| 257. | o,o'-di-CH$_3$O-p-CN-phenyl | SO$_2$NH$_2$ | CH$_3$ | CH$_3$ |
| 258. | o,o'-di-CH$_3$O-p-CN-phenyl | SO$_2$NH$_2$ | CH$_3$ | cyclopropyl |
| 259. | o,o'-di-CH$_3$O-p-CN-phenyl | SO$_2$NH$_2$ | H | cyclopropyl |
| 260. | o,o'-di-CH$_3$O-p-CN-phenyl | SO$_2$NH$_2$ | H | CH$_3$ |
| 261. | o,o'-di-CH$_3$O-p-CN-phenyl | F | CH$_3$ | CH$_3$ |
| 262. | o,o'-di-CH$_3$O-p-CN-phenyl | F | CH$_3$ | cyclopropyl |

TABLE 4-continued

Contemplated Compounds of Formula IA-4

| | Ar | V | W | Z |
|---|---|---|---|---|
| 263. | o,o'-di-CH$_3$O-p-CN-phenyl | F | H | cyclopropyl |
| 264. | o,o'-di-CH$_3$O-p-CN-phenyl | F | H | CH$_3$ |
| 265. | o,o'-di-CH$_3$-p-CN-phenyl | SO$_2$NH$_2$ | CH$_3$ | CH$_3$ |
| 266. | o,o'-di-CH$_3$-p-CN-phenyl | SO$_2$NH$_2$ | CH$_3$ | cyclopropyl |
| 267. | o,o'-di-CH$_3$-p-CN-phenyl | SO$_2$NH$_2$ | H | cyclopropyl |
| 268. | o,o'-di-CH$_3$-p-CN-phenyl | SO$_2$NH$_2$ | H | CH$_3$ |
| 269. | o,o'-di-CH$_3$-p-CN-phenyl | F | CH$_3$ | CH$_3$ |
| 270. | o,o'-di-CH$_3$-p-CN-phenyl | F | CH$_3$ | cyclopropyl |
| 271. | o,o'-di-CH$_3$-p-CN-phenyl | F | H | cyclopropyl |
| 272. | o,o'-di-CH$_3$-p-CN-phenyl | F | H | CH$_3$ |
| 273. | o,o'-diCH$_3$O-p-(CH=CHCN)-phenyl | SO$_2$NH$_2$ | F | CH$_3$ |
| 274. | o,o'-diCH$_3$O-p-(CH=CHCN)-phenyl | SO$_2$NH$_2$ | F | cyclopropyl |
| 275. | o,o'-diCH$_3$O-p-(CH=CHCN)-phenyl | F | F | cyclopropyl |
| 276. | o,o'-diCH$_3$O-p-(CH=CHCN)-phenyl | F | F | CH$_3$ |
| 277. | 4-cyclopropylnaphth-1-yl | SO$_2$NH$_2$ | F | CH$_3$ |
| 278. | 4-cyclopropylnaphth-1-yl | SO$_2$NH$_2$ | F | cyclopropyl |
| 279. | 4-cyclopropylnaphth-1-yl | F | F | CH$_3$ |
| 280. | 4-cyclopropylnaphth-1-yl | F | F | cyclopropyl |
| 281. | o,o'-di-CH$_3$O-p-CN-phenyl | SO$_2$NH$_2$ | F | CH$_3$ |
| 282. | o,o'-di-CH$_3$O-p-CN-phenyl | SO$_2$NH$_2$ | F | cyclopropyl |
| 283. | o,o'-di-CH$_3$O-p-CN-phenyl | F | F | CH$_3$ |
| 284. | o,o'-di-CH$_3$O-p-CN-phenyl | F | F | cyclopropyl |
| 285. | o,o'-di-CH$_3$-p-CN-phenyl | SO$_2$NH$_2$ | F | CH$_3$ |
| 286. | o,o'-di-CH$_3$-p-CN-phenyl | SO$_2$NH$_2$ | F | cyclopropyl |
| 287. | o,o'-di-CH$_3$-p-CN-phenyl | F | F | CH$_3$ |
| 288. | o,o'-di-CH$_3$-p-CN-phenyl | F | F | cyclopropyl |
| 289. | 2,4,6-trimethyl phenyl | CN | CH$_3$ | CH$_3$ |
| 290. | 2,4,6-trimethyl phenyl | CN | CH$_3$ | cyclopropyl |
| 291. | 2,4,6-trimethyl phenyl | CN | H | cyclopropyl |
| 292. | 2,4,6-trimethyl phenyl | CN | H | CH$_3$ |
| 293. | 2,4,6-trimethyl phenyl | CH=CHCN | CH$_3$ | CH$_3$ |
| 294. | 2,4,6-trimethyl phenyl | CH=CHCN | CH$_3$ | cyclopropyl |
| 295. | 2,4,6-trimethyl phenyl | CH=CHCN | H | cyclopropyl |
| 296. | 2,4,6-trimethyl phenyl | CH=CHCN | H | CH$_3$ |
| 297. | 2,4,6-trimethyl phenyl | CN | F | CH$_3$ |
| 298. | 2,4,6-trimethyl phenyl | CN | F | cyclopropyl |
| 299. | 2,4,6-trimethyl phenyl | CH=CHCN | F | CH$_3$ |
| 300. | 2,4,6-trimethyl phenyl | CH=CHCN | F | cyclopropyl |
| 301. | 2,4,6-trimethyl phenyl | SO$_2$NH$_2$ | CH$_3$ | CH$_3$ |
| 302. | 2,4,6-trimethyl phenyl | SO$_2$NH$_2$ | CH$_3$ | cyclopropyl |
| 303. | 2,4,6-trimethyl phenyl | SO$_2$NH$_2$ | H | cyclopropyl |
| 304. | 2,4,6-trimethyl phenyl | SO$_2$NH$_2$ | H | CH$_3$ |
| 305. | 2,4,6-trimethyl phenyl | F | CH$_3$ | CH$_3$ |
| 306. | 2,4,6-trimethyl phenyl | F | CH$_3$ | cyclopropyl |
| 307. | 2,4,6-trimethyl phenyl | F | H | cyclopropyl |
| 308. | 2,4,6-trimethyl phenyl | F | H | CH$_3$ |
| 309. | 4-cyclopropyl phenyl | SO$_2$NH$_2$ | F | CH$_3$ |
| 310. | 4-cyclopropyl phenyl | SO$_2$NH$_2$ | F | cyclopropyl |
| 311. | 4-cyclopropyl phenyl | F | F | CH$_3$ |
| 312. | 4-cyclopropyl phenyl | F | F | cyclopropyl |
| 313. | o,o'-dimethyl-p-cyclopropyl phenyl | CN | CH$_3$ | CH$_3$ |
| 314. | o,o'-dimethyl-p-cyclopropyl phenyl | CN | CH$_3$ | cyclopropyl |
| 315. | o,o'-dimethyl-p-cyclopropyl phenyl | CN | H | cyclopropyl |
| 316. | o,o'-dimethyl-p-cyclopropyl phenyl | CN | H | CH$_3$ |
| 317. | o,o'-dimethyl-p-cyclopropyl phenyl | CH=CHCN | CH$_3$ | CH$_3$ |
| 318. | o,o'-dimethyl-p-cyclopropyl phenyl | CH=CHCN | CH$_3$ | cyclopropyl |
| 319. | o,o'-dimethyl-p-cyclopropyl phenyl | CH=CHCN | H | cyclopropyl |
| 320. | o,o'-dimethyl-p-cyclopropyl phenyl | CH=CHCN | H | CH$_3$ |
| 321. | o,o'-dimethyl-p-cyclopropyl phenyl | CN | F | CH$_3$ |
| 322. | o,o'-dimethyl-p-cyclopropyl phenyl | CN | F | cyclopropyl |
| 323. | o,o'-dimethyl-p-cyclopropyl phenyl | CH=CHCN | F | CH$_3$ |
| 324. | o,o'-dimethyl-p-cyclopropyl phenyl | CH=CHCN | F | cyclopropyl |
| 325. | o,o'-dimethyl-p-cyclopropyl phenyl | SO$_2$NH$_2$ | CH$_3$ | CH$_3$ |
| 326. | o,o'-dimethyl-p-cyclopropyl phenyl | SO$_2$NH$_2$ | CH$_3$ | cyclopropyl |
| 327. | o,o'-dimethyl-p-cyclopropyl phenyl | SO$_2$NH$_2$ | H | cyclopropyl |
| 328. | o,o'-dimethyl-p-cyclopropyl phenyl | SO$_2$NH$_2$ | H | CH$_3$ |
| 329. | o,o'-dimethyl-p-cyclopropyl phenyl | F | CH$_3$ | CH$_3$ |
| 330. | o,o'-dimethyl-p-cyclopropyl phenyl | F | CH$_3$ | cyclopropyl |
| 331. | o,o'-dimethyl-p-cyclopropyl phenyl | F | H | cyclopropyl |
| 332. | o,o'-dimethyl-p-cyclopropyl phenyl | F | H | CH$_3$ |
| 333. | 2,4,6-trimethyl phenyl | SO$_2$NH$_2$ | F | CH$_3$ |
| 334. | 2,4,6-trimethyl phenyl | SO$_2$NH$_2$ | F | cyclopropyl |
| 335. | 2,4,6-trimethyl phenyl | F | F | CH$_3$ |
| 336. | 2,4,6-trimethyl phenyl | F | F | cyclopropyl |
| 337. | o,o'-di-CH$_3$-p-acetyl-phenyl | CN | H | H |
| 338. | o,o'-di-CH$_3$-p-acetyl-phenyl | CN | CH$_3$ | H |
| 339. | o,o'-di-CH$_3$-p-acetyl-phenyl | CN | H | Cl |
| 340. | o,o'-di-CH$_3$-p-acetyl-phenyl | CN | CH$_3$ | Cl |

Additional contemplated and prophetic examples, which are not exhaustive but merely representative of this invention, are shown below:

147
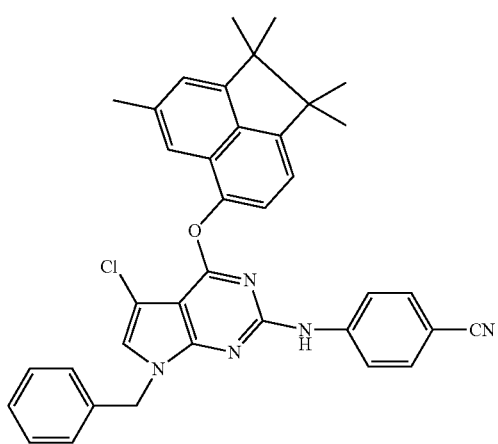
148
-continued
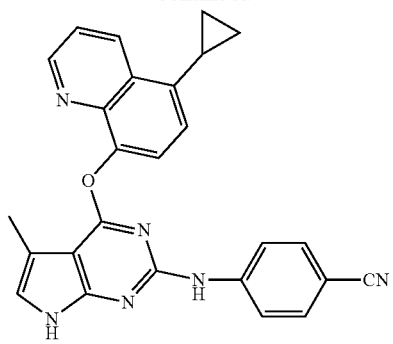
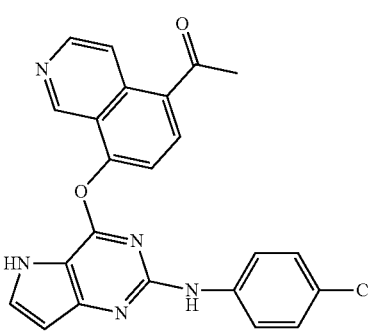
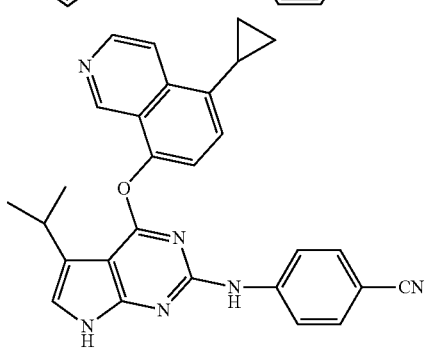
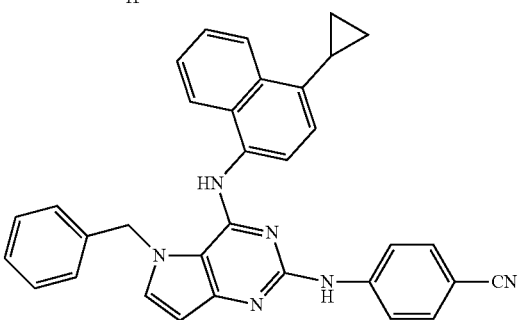
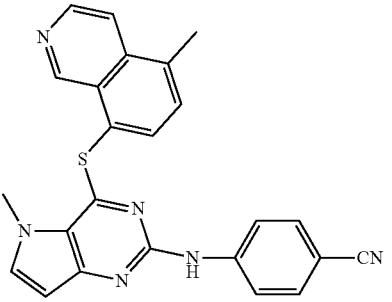

-continued

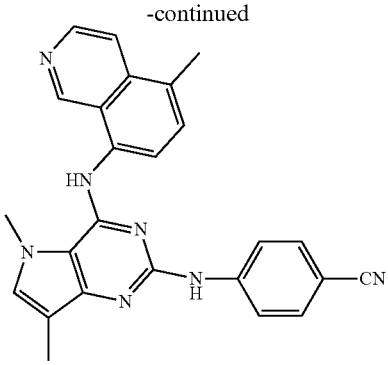

What is claimed is:
1. A compound of formula

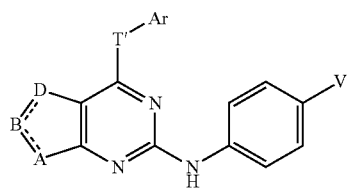

IA where
the dashed line represents a double bond between either A and B or B and D,
T' is O or S;
A is NZ;
B is =CH;
D is =CW;
Z is H, Br, CH$_3$, CH$_2$CH$_3$, cyclopropyl, or benzyl, the phenyl moiety of said benzyl optionally substituted with one or two groups selected independently from methyl and methoxy;
W is H, F, Cl, Br, methyl, ethyl, cyclopropyl, allyl, CH$_2$CF$_3$, cyanomethyl, CH$_2$CH$_2$CN, CH=CHCN, or benzyl, the phenyl moiety of said benzyl optionally substituted with one or two groups selected independently from methyl and methoxy,
V is F, Cl, CN, SO$_2$CH$_3$, SO$_2$NH$_2$, SO$_2$NHCH$_3$, C≡CCH$_3$, or CH=CHCN;
Ar is (a), (b), (c), or (d) below

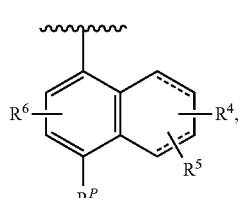

(a)

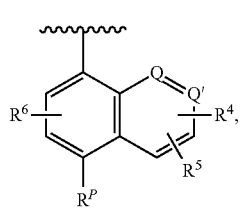

(b)

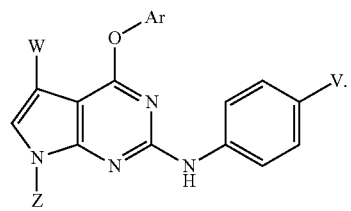

where
the dashed lines in (a) represent optional double bonds;
R$^P$ is Cl, Br, I, CN, methyl, ethyl, n-propyl, isopropyl, cyclopropylmethyl, C$_3$-C$_6$ cycloalkyl, CH=CHCN, acetyl, or NH—C$_1$-C$_6$ alkyl, said alkyl and cycloalkyl groups optionally substituted with methyl, methoxy, halogen, or cyano;
R$^4$, R$^5$, and R$^6$ are, independently, H, F, Cl, Br, CH$_3$, CH$_2$F, CHF$_2$, CF$_3$, isopropyl, cyclopropyl, OCH$_3$, OH, OCF$_3$, NH$_2$ and NHCH$_3$,
or R$^6$ and R$^P$ on adjacent ring atoms, together with the ring atoms to which they are attached, form an additional fused five-membered ring;
Q and Q' are, independently, N or CH;
R$^7$ is Cl, Br, I, CH$_3$, CF$_3$, OCH$_3$, isopropyl, cyclopropyl, t-butyl, or cyclobutyl; and
R$^8$, R$^9$, R$^{10}$ and R$^{11}$ are each, independently, H or CH$_3$.

2. The compound of claim 1, wherein Ar is (a) or (c).

3. The compound of claim 2, where R$^6$ either is H or is in the 2-position.

4. The compound of claim 1, which is a compound of formula IA-2

IA-2

5. The compound of claim 4, where Ar is 4-cyclopropyl-, 4-acetyl-, 4-methyl-, 4-bromo-, or 4-cyano-2,6-di-substituted phenyl.

6. The compound of claim 1, where
V is CN, and where
W is, H, methyl, F, Cl, Br, or benzyl,
Z is, H, methyl, Br, or benzyl.

7. The compound of claim 3 which is a compound of formula IA-2a:

IA-2a

8. The compound of claim 7, where
V is CN or CH=CHCN,
$R^6$ is methyl, methoxy, or chloro and
$R^7$ is 6-methyl, or 6-methoxy.
9. The compound of claim 8, where $R^P$ is CN, cyclopropyl, methyl, Br, Cl, CH=CHCN, or acetyl.
10. The compound of claim 9 where
V is CN,
W is H, chloro, bromo, methyl, or ethyl and
Z is H, methyl, ethyl, or benzyl.
11. A compound of formula IB

IB where
the dashed line represents a double bond between either A and B or B and D, and where
A is NZ;
B is =CH;
D is =CW;
Z is H, Br, $CH_3$, $CH_2CH_3$, cyclopropyl, or benzyl, the phenyl moiety of said benzyl optionally substituted with methyl or methoxy;
W is H, F, Cl, Br, methyl, ethyl, cyclopropyl, allyl, $CH_2CF_3$, cyanomethyl, $CH_2CH_2CN$, CH=CHCN, or benzyl, the phenyl moiety of said benzyl optionally substituted with methyl or methoxy;
V is F, Cl, CN, $SO_2CH_3$, $SO_2NH_2$, $SO_2NHCH_3$, C≡$CCH_3$, or CH=CHCN,
Ar is (a), (b), or (d) below:

(a)

-continued (b)

(d)

where
$R^P$ is Cl, Br, I, CN, methyl, ethyl, n-propyl, isopropyl, cyclopropylmethyl, $C_3$-$C_6$ cycloalkyl, CH=CHCN, acetyl, or NH—$C_1$-$C_6$ alkyl, said alkyl and cycloalkyl groups optionally substituted with methyl, methoxy, halogen, or cyano;
$R^4$, $R^5$, and $R^6$ are, independently, H, F, Cl, Br, $CH_3$, $CH_2F$, $CHF_2$, $CF_3$, isopropyl, cyclopropyl, $OCH_3$, OH, $OCF_3$, $NH_2$ and $NHCH_3$;
Q and Q' are, independently, N or CH; and
$R^8$, $R^9$, $R^{10}$ and $R^{11}$ are each, independently, H or $CH_3$.
12. A compound of formula IB-1

IB-1 where
the dashed line represents a double bond between either A and B or B and D;
A is NZ;
B is =CH;
D is =CW;
Z is H, Br, $CH_3$, $CH_2CH_3$, cyclopropyl, or benzyl, the phenyl moiety of said benzyl optionally substituted with methyl or methoxy,
W is H, F, Cl, Br, methyl, ethyl, cyclopropyl, allyl, $CH_2CF_3$, $CH_2CN$, $CH_2CH_2CN$, CH=CHCN, or benzyl, the phenyl moiety of said benzyl optionally substituted with methyl or methoxy,
V is F, Cl, CN, $SO_2CH_3$, $SO_2NH_2$, $SO_2NHCH_3$, C≡$CCH_3$, or CH=CHCN;

$R^P$ is Cl, Br, I, CN, CH=CHCN, methyl, ethyl, n-propyl, isopropyl, cyclopropylmethyl, $C_3$-$C_6$ cycloalkyl, acetyl, and NH—$C_3$-$C_6$ alkyl;

$R^6$ is H, F, Cl, Br, $CH_3$, $CH_2F$, $CHF_2$, $CF_3$, isopropyl, cyclopropyl, $OCH_3$, OH, $OCF_3$, $NH_2$ and $NHCH_3$; and $R^7$ is Cl, Br, I, $CH_3$, $CF_3$, $OCH_3$, isopropyl, cyclopropyl, t-butyl, or cyclobutyl.

13. The compound of claim 12, where
V is CN or CH=CHCN,
$R^6$ is 2-methyl, 2-methoxy, or 2-chloro and
$R^7$ is 6-methyl, or 6-methoxy.

14. The compound of claim 13, where $R^P$ is CN, cyclopropyl, methyl, Br, Cl, CH=CHCN, or acetyl.

* * * * *